United States Patent
Schulz et al.

(10) Patent No.: US 9,458,426 B2
(45) Date of Patent: Oct. 4, 2016

(54) SMALL MOLECULES SUPPORTING PLURIPOTENT CELL GROWTH AND METHODS THEREOF

(71) Applicant: ViaCyte, Inc., San Diego, CA (US)

(72) Inventors: Thomas C Schulz, Athens, GA (US); Allan J Robins, Athens, GA (US)

(73) Assignee: VIACYTE, INC., San Diego, CA (US)

( * ) Notice: Subject to any disclaimer, the term of this patent is extended or adjusted under 35 U.S.C. 154(b) by 84 days.

(21) Appl. No.: 14/161,656

(22) Filed: Jan. 22, 2014

(65) Prior Publication Data

US 2014/0186948 A1    Jul. 3, 2014

Related U.S. Application Data

(63) Continuation of application No. 13/259,151, filed as application No. PCT/US2010/032601 on Apr. 27, 2010, now Pat. No. 8,685,726.

(60) Provisional application No. 61/172,998, filed on Apr. 27, 2009.

(51) Int. Cl.
| | |
|---|---|
| C12N 5/00 | (2006.01) |
| C12N 5/074 | (2010.01) |
| C07K 14/475 | (2006.01) |
| C12N 5/0735 | (2010.01) |

(52) U.S. Cl.
CPC ........... *C12N 5/0607* (2013.01); *C07K 14/475* (2013.01); *C12N 5/0606* (2013.01); *C12N 2501/105* (2013.01); *C12N 2501/115* (2013.01); *C12N 2501/16* (2013.01); *C12N 2501/195* (2013.01); *C12N 2501/80* (2013.01); *C12N 2501/805* (2013.01); *C12N 2501/825* (2013.01); *C12N 2501/845* (2013.01)

(58) Field of Classification Search
CPC .... C12N 5/00; C12N 5/0606; C12N 5/0607; C12N 2501/80
USPC ................ 435/325, 366, 377, 383, 384, 405
See application file for complete search history.

(56) References Cited

U.S. PATENT DOCUMENTS

| 2004/0121464 A1 | 6/2004 | Rathjen et al. |
| 2012/0021513 A1 | 1/2012 | Schulz et al. |

FOREIGN PATENT DOCUMENTS

| WO | 2007148332 | 12/2007 |
| WO | 2010129294 A2 | 11/2010 |
| WO | 2010129294 A3 | 11/2010 |

OTHER PUBLICATIONS

Ludwig et al, Nature Biotechnology 24(2): 185-187, including Supplementary documents, 7 pgs, 2006.*
Amit et al, Biology of Reproduction 70:837-845, 2004.*
Corning, Surface Areas, Recommended Medium Volumes for Cell Culture Vessels, 4 pgs, Sep. 2008.*
Levenstein et al, Stem Cells 24:568-574, 2006.*
Thermo Scientific Plate Guide, Nunc, www.thermoscientific.com/plateguide; 7 pgs, 2011.*
Watanabe et al, Nature Biotechnology 25(6):681-686, 2007.*
Eiges et al, Current Biology 11(7): 514-518, 2001.*
Forsyth et al, Cloning and Stem Cells 8(10:16-23, 2006.*
Andang,et al., "Histone H2AX-dependent GABAA receptor regulation of stem cell proliferation", Nature 451:460-65 (2008).
Schulz, et al., "A Scalable System for Production of Functional Pancreatic Progenitors from Human Embryonic Stem Cells", PLOS 7, e37004:1-17 (2012).
Yu, et al., "Human Induced Pluripotent Stem Cells Free of Vector and Transgene Sequences", Science 324:797-801 (2009).
Takahashi, et al., "Induction of Pluripotent Stem Cells from Adult Human Fibroblasts by Defined Factors", Cell 131:861-872 (2007).
Heo, et al., "ATP Stimulates Mouse Embryonic Stem Cell Proliferation via", Stem Cells 24: 2637-48 (2006).
Katayama, et al., "Signals from the Sympathetic Nervous System Regulate Hematopoietic Stem Cell Egress from Bone Marrow", Cell 124:407-21 (2006).
Ma, et al., "Acetylcholine stimulates cortical precursor cell proliferation in vitro via muscarinic receptor activation and MAP kinase phosphorylation", Eur J Neurosc 12:1227-40 (2000).
Ikehara, "Pluripotent Hematopoeitic Stem Cells in Mice and Humans", Proc. Soc. Exp. Biol. Med. 223:149-155 (2000).
Laharrague,et al., "High expression of leptin by human bone marrow adipocytes in primary culture.", FASEB J. 12:747-752 (1998).
Canoll, et al., "GGF/Neuregulin is a Neuronal Signal that Promotes the Proliferation and Survival and Inhibits the Differentiation of Oligodendrocyte Progenitors", Neuron 17:229-243 (1996).
Berdel, et al., "Various human hematopoietic growth factors (interleukin-3, GM-CSF, G-CSF) stimulate clonal growth of nonhematopoietic tumor cells", Blood 73: 80-83 (1989).
R&D Systems, "Recombinant Human NRG1/HRG1, CF from R&D Systems", (http://www.biocompare.com/10204-Biomolecule/987458-Recombinant-Human-NRG1HR.; last accessed Jan. 23, 2013.
Kim, et al., "Epinephrine Increases DNA Synthesis via ERK1/2s Through cAMP, Ca2+/PKC, and PI3K/Akt Signaling Pathways in Mouse Embryonic Stem Cells", J. Cell. Biochem 104, 2008, 1407-1420.
Pyle, et al., "Neurotrophins mediate human embryonic stem cell survival", Nat Biotechnol 24, 2006, 344-50.

* cited by examiner

*Primary Examiner* — Kevin Hill
(74) *Attorney, Agent, or Firm* — The Law Office of Jane K. Babin, Professional Corporation; Jane K. Babin

(57) ABSTRACT

The present invention relates to compositions and methods for maintaining undifferentiated pluripotent stem cell cultures.

23 Claims, 17 Drawing Sheets

Figure 1

Legend: No effect ( - ); Primary 10 uM (+++)

| Compound | Primary 10 uM | 50 | 25 | 10 | 5 | 1 | 0.1 | Target Receptors | Action |
|---|---|---|---|---|---|---|---|---|---|
| 7-Chloro-4-hydroxy-2-phenyl-1,8-naphthyridine | - | - | - | - | - | +++ | +++ | Adenosine | Antagonist |
| Domperidone | +/- | +/- | + | ++ | +++ | +++ | +++ | Dopamine | Antagonist |
| Ivermectin | - | - | - | - | - | +++ | +++ | Cholinergic | Modulator |
| MG 624 | - | - | - | - | - | +/- | ++ | Cholinergic | Antagonist |
| Pentamidine isethionate | - | - | - | + | - | - | +++ | Glutamate | Antagonist |
| SB 224289 hydrochloride | - | - | - | + | +++ | +++ | +++ | Serotonin | Antagonist |
| Terfenadine | - | - | - | - | ++ | +++ | +++ | Histamine | Antagonist |

Secondary/Dosing (uM)

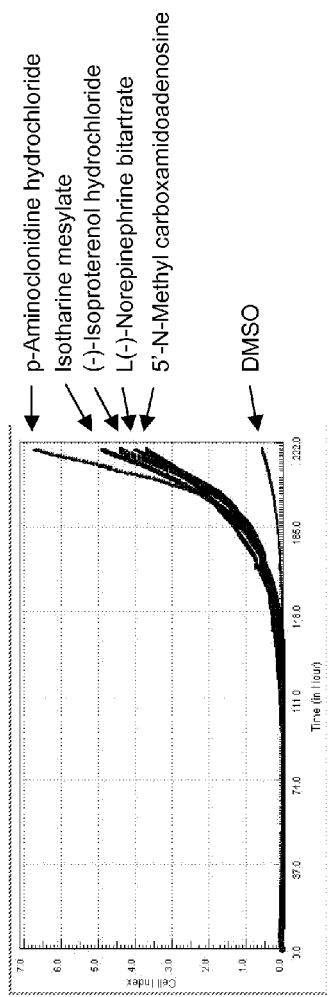
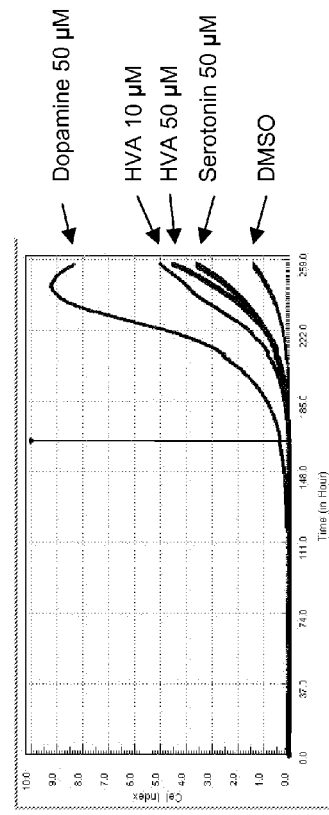
Figure 6

1=HI drug
2=H drug
3=HAI drug
4=I drug
5=HI

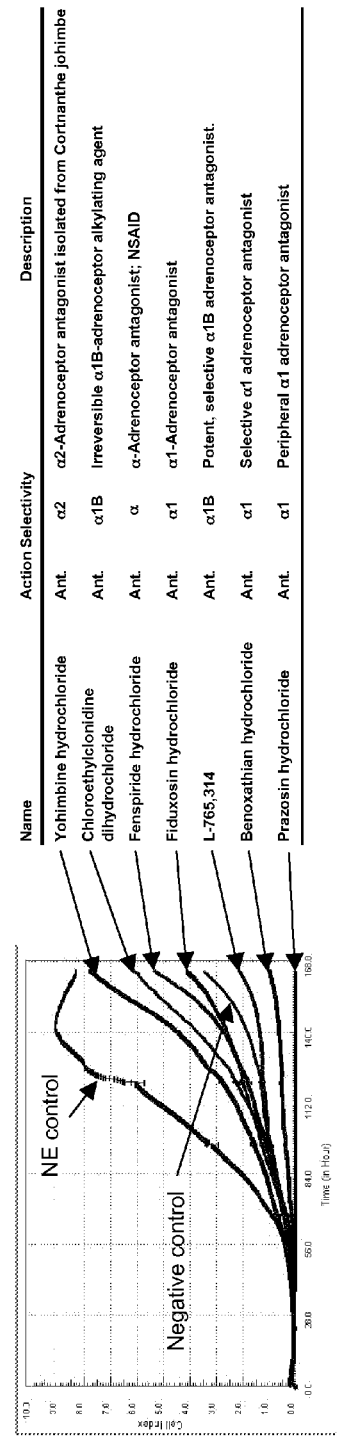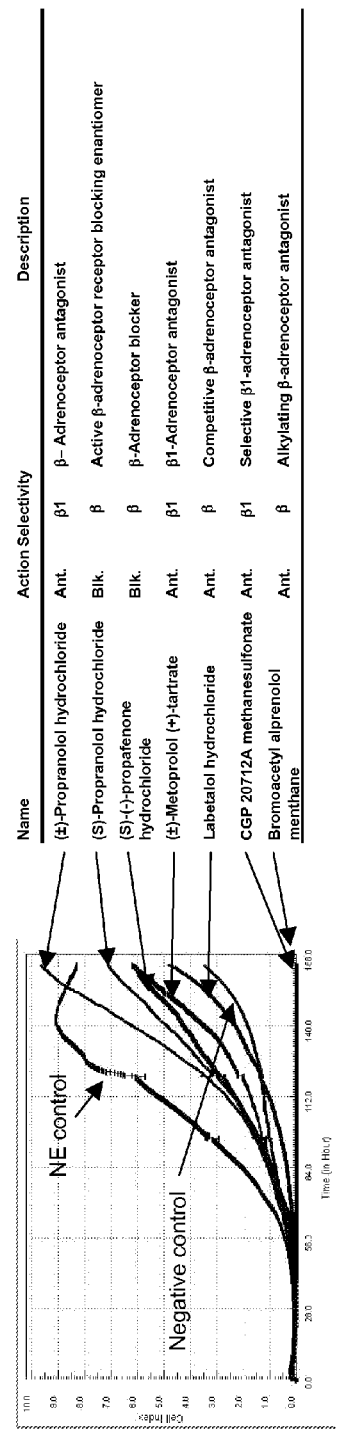
Figure 17

_US 9,458,426 B2_

SEQUENCE LISTING

```
<160> NUMBER OF SEQ ID NOS: 46

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 1
aagaggccat caagcagatc a                                           21

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 2
caggaggcgc atccaca                                                17

<210> SEQ ID NO 3
```

```
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 3
ctggcctgta cccctcatca                                              20

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 4
cttcccgtct tgtccaaca a                                             21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 5
aagtctacca aagctcacgc g                                            21

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 6
gtaggcgccg cctgc                                                   15

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 7
gctcatcgct ctctattctt ttgc                                         24

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 8
ggttgaggcg tcatcctttc t                                            21

<210> SEQ ID NO 9
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 9
```
gggagcggtg aagatgga                                                  18

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 10
tcatgttgct cacggaggag ta                                             22

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 11
aagcatttac tttgtggctg gatt                                           24

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 12
tgatctggat ttctcctctg tgtct                                          25

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 13
cgctccgctc agcagcat                                                  18

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 14
gtgttgcctc tatccttccc at                                             22

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 15
gaagaaggaa gccgtccaga                                                20

<210> SEQ ID NO 16
<211> LENGTH: 20
<212> TYPE: DNA

```
<213> ORGANISM: Artificial Sequence
<220> FEATURE:
<223> OTHER INFORMATION: Oligonucleotide Primer

<400> SEQUENCE: 16
gaccttcgag tgctgatccg                                               20

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 17
ggcgcagcag aatccaga                                                 18

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(20)
<223> OTHER INFORMATION: n is a, c, g, or t

<400> SEQUENCE: 18
nnnnnnnnnn nnnnnnnnnn                                               20

<210> SEQ ID NO 19
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 19
caccgcgggc atgatc                                                   16

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 20
acttccccag gaggttcga                                                19

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 21
ggccttcagt actccctgca                                               20

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide Primer
```

```
<400> SEQUENCE: 22
gggacttgga gcttgagtcc t                                          21

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 23
gaaggtcatc atctgccatc g                                          21

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 24
ggccataatc agggtcgct                                             19

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 25
ccccagactc cgtcagtttc                                            20

<210> SEQ ID NO 26
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 26
tccgtctggt tgggttcag                                             19

<210> SEQ ID NO 27
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 27
ccagaaagga tgcctcataa agg                                        23

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 28
tctgcgcgcc cctagtta                                              18

<210> SEQ ID NO 29
```

```
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 29
tgggctcgag aaggatgtg                                              19

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 30
gcatagtcgc tgcttgatcg                                             20

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 31
ccgagtccag gatccaggta                                             20

<210> SEQ ID NO 32
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 32
ctctgacgcc gagacttgg                                              19

<210> SEQ ID NO 33
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 33
cctcttgcaa tgcggaaag                                              19

<210> SEQ ID NO 34
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 34
cgggaggaag gctctcact                                              19

<210> SEQ ID NO 35
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 35
```
gaggagaaag tggaggtctg gcc                                             23

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 36
ctctgatgag gaccgcttct g                                               21

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 37
acagtgccct tcagccagac t                                               21

<210> SEQ ID NO 38
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 38
acaactactt tttcacagcc ttcgt                                           25

<210> SEQ ID NO 39
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 39
gagaaaccca ctggagatga aca                                             23

<210> SEQ ID NO 40
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 40
ctcatggcaa agttcttcca gaa                                             23

<210> SEQ ID NO 41
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 41
atgcaccgct acgacatgg                                                  19

<210> SEQ ID NO 42
<211> LENGTH: 21
<212> TYPE: DNA

```
<213> ORGANISM: Artificial Sequence
<220> FEATURE:
<223> OTHER INFORMATION: Oligonucleotide Primer

<400> SEQUENCE: 42
ctcatgtagc cctgcgagtt g                                            21

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 43
ctggctgtgg caaggtcttc                                              20

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 44
cagccctcaa actcgcactt                                              20

<210> SEQ ID NO 45
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 45
atcgaggagc gccacaac                                                18

<210> SEQ ID NO 46
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 46
tgctggatgg tgtcctggt                                               19
```

SMALL MOLECULES SUPPORTING PLURIPOTENT CELL GROWTH AND METHODS THEREOF

RELATED APPLICATIONS

This application is a continuation under 35 USC §120 of U.S. patent application Ser. No. 13/259,151, filed Sep. 23, 2011 (allowed); which is the National Phase under 35 USC §371 of PCT International Application No. PCT/US10/32601, filed Apr. 27, 2010; which in turn claims the benefit of priority under 35 USC §119 of U.S. Provisional Application Ser. No. 61/172,998, filed Apr. 27, 2009. The entire disclosure of each of these prior applications is incorporated herein by reference.

FIELD OF THE INVENTION

The present invention relates to a pluripotent stem cell medium containing at least in part small molecule neurotransmitters. In particular, the invention relates to defined pluripotent stem cell media that are essentially serum and feeder-free, include at least one of norepinephrine, acetylcholine or dopamine and support suspension cell aggregate culture of pluripotent human stem cells.

BACKGROUND OF THE INVENTION

The eventual application of pluripotent based cell replacement therapies will require the development of methods that enable large scale culture and differentiation conditions that are compliant with regulatory guidelines.

In the United States, the Food and Drug Administration (FDA) has issued guidance in the form of Draft Guidance for Reviewers: Instructions and Template for Chemistry, Manufacturing, and Control (CMC) Reviewers of Human Somatic Cell Therapy Investigational New Drug Applications (INDs); and in the 21 CFR §1270 and §1271 regulations. In Europe, the requirement for cell therapy products is outlined in several directives and guidelines that are pertinent to human embryonic stem (hES) cells. See Directive 2004/23/EC, Commission Directives 2006/17/EC and 2006/86/E, EU Regulation 1394/2007, guideline EMEA/CHMP/410869, which are herein incorporated by reference in their entireties. Each country has certain regulatory standards for quality and safety including donation, procurement, testing, processing, preservation, storage and distribution of human tissues and cells. Regulations establish guidelines for development, manufacturing and quality control as well as nonclinical and clinical development of cell-based medicinal products. See also C. Unger et al. (2008), Human Molecular Genetics 17(R1):R48-R53.

Regulatory guidelines present many hurdles for manufacturing-scale production of stem cells and products thereof. For example, to maintain pluripotent cells in an undifferentiated state in vitro, research studies still employ animal products such as mouse embryonic fibroblast (MEF) feeders and fetal bovine serum (FBS). Still other cell culture conditions for maintaining pluripotentcy contain serum replacers, such as KnockOut™ Serum Replacer (KSR; Invitrogen), which although more defined, still contains a complex crude mixture containing unknown compounds as well as bovine serum albumin (BSA) or lipid-rich albumin fraction of bovine serum (AlbuMAX). Further, serum batches vary in their activity and therefore their capability of maintaining pluripotent undifferentiated cell cultures. Hence, the replacement of bovine serum with non-animal derived ("xeno-free") defined components is preferred for GMP production of pluripotent cells.

Applicants previously determined that activation of the IGF1, Insulin, ERBB2 and ERBB3 receptors was a hallmark of proliferating hES cells. IGF1R/IR activation could be attributed to IGF1 in serum or microgram/ml concentrations of insulin, for example, in serum replacer or N2/B27 cell culture supplements in a range of growth conditions. These activities provide a strong PI3 kinase/AKT signal, and equivalent activation could be achieved with lower concentrations of LR3-IGF1, an IGF1 analog. See McLean et al., 2007 Stem Cells 25, 29-38. Phosphorylation of ERBB2/3 was consistent with the activity of an EGF family member, heregulin/neuregulin, in MEF-CM. See Wang et al., 2007 Blood 110, 4111-9 Inhibition of IGF1R and ERBB2 impacted self-renewal of hES cell, as did small molecule inhibitors of Activin and FGF signaling. See Robins and Schulz, 2009, "Novel methods of Stem Cell Culture and Maintenance: Media and extra cellular matrix requirements for large scale ESC growth." In _Emerging Technology Platforms for Stem Cells_ (eds. U. Lakshmipathy J. D. Chesnut and B. Thyagarajan, pp. 251-247) Hoboken. John Wiley & Sons Inc.; and Vallier et al., 2005 J Cell Sci 118, 4495-509). This defined medium was developed and termed DC-HAIF, which consisted of DMEM/F12, non essential amino acids, trace elements, ascorbic acid, β-mercaptoethanol, Penicillin/Streptomycin (optional), with the only proteins being caprylic acid extracted fatty acid-free BSA, transferrin, and recombinant Heregulin-1β (H), Activin A (A), LR3-IGF1 (I), and FGF2 (F). DC-HAIF supported long term maintenance of pluripotent hES cells, as well as single cell passaging and scaled expansion of hES cell using ACCUTASE™. See Robins and Schulz (2009) supra; Wang et al., supra. A batch-tested commercial formulation of DC-HAIF is available from under license to Life Technologies and sold under the trade name StemPro® hES cell SFM.

Still there remains a need to identify alternative and/or additional signaling pathways with critical functions in pluripotent stem cells, e.g. hES and iPS cells, and that are able to be used for therapeutic purposes, wherein the culture compositions are defined and/or produced to GMP standard.

SUMMARY OF THE INVENTION

The invention relates to compositions comprising a basal salt nutrient solution for pluripotent cell growth comprising at least norepinephrine and/or dopamine, the composition being essentially free of serum.

BRIEF DESCRIPTION OF THE DRAWINGS

FIG. 1. Representation of antagonists/modulators of neurotransmitter/hormone receptors identified by compound screening in hES cells. Alkaline phosphatase (AP) staining of the primary library screen demonstrated no effect (+++, confluent growth), moderate effect (++), or severe (+) impact on cells; only rare cells (+/−), or no cells (−) are also indicated. Receptor antagonists identified in the primary screen are shown (left column) The screen was performed using compounds at 10 μM. The secondary dose titration assay is shown (50-0.1 μM columns), and receptor class targeted by each compound and action is indicated.

FIG. 6. Additional neurotransmitters and related compounds that support low-density survival of hES cells. 1000 hES cells/well were plated in StemPro® hESC SFM containing Heregulin, IGF1 and Activin (HIA) and the indicated small molecules. (A) Identification of additional Adenosine and Adrenoceptor agonists that support low-density survival. Compounds were tested at 10 µM. The DMSO trace is an average of 8 wells. (B) Tabulated information on the identified compounds. (C) Dopamine, homovanillioc acid (HVA) and serotonin support low-density survival of hES cell. Compounds were tested at the indicated concentrations. The spike in impedance at hr ~160 is an artifact and an error.

FIG. 17. Inhibition of adrenoceptors impacts survival and expansion of hES cell at low density. A low density culture of 2000 BG02 cells/well was plated in StemPro® hESC SFM containing heregulin, activin, LR3-IGF1 and 50 µM NE in the impedance reader and monitored for 7 days. Eight wells of each control were included, and contained either DMSO (negative control), or DMSO/50 µM NE (NE control). 40 different inhibitors of alpha- or beta-adrenoceptors were tested in duplicate for overriding negative effects upon NE mediated survival/expansion of hES cells at low density. Seven α-adrenoceptor antagonists (Ant.), 5β-adrenoceptor antagonists, and 2β-adrenoceptor blockers were identified that impacted hES cell. The names, action, known selectivity and description of each active compound are indicated.

DETAILED DESCRIPTION OF THE INVENTION

Figure 2:
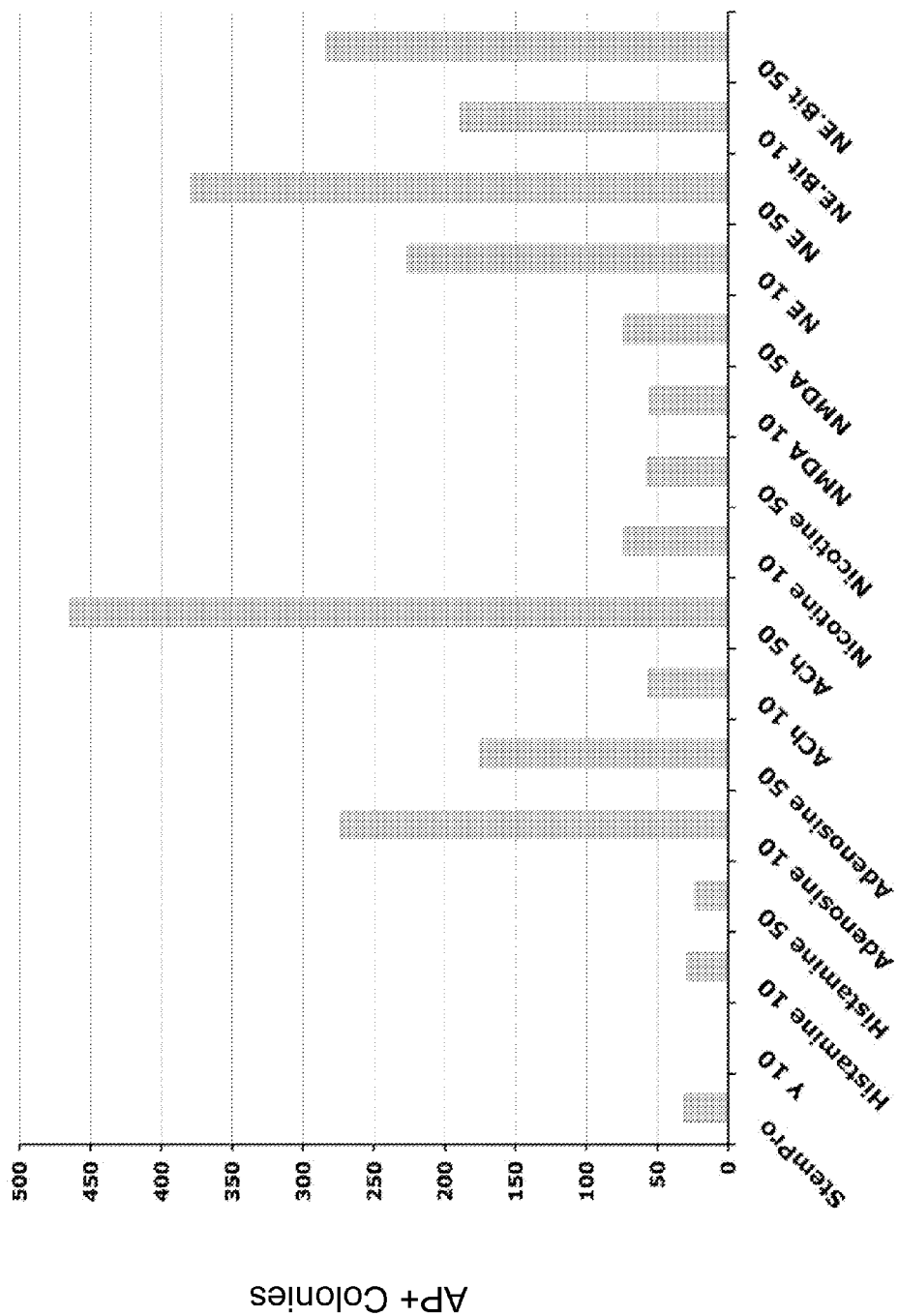
FIG. 2. Low density plating assay of hES cells (e.g., BGO2 cells). 10000 cells/well were plated in 6-well trays in StemPro® hESC SFM (Life Technologies) medium and stained with alkaline phosphatase (AP+) after 7 days. Y (Y27632), ACh (acetylcholine), NMDA (N-methyl-D-aspartic acid), NE ((−)-Norepinephrine), NE.Bit ((±)-Norepinephrine (+)-bitartrate). Compounds were added at 10 or 50 µM as indicated.

In order to highlight additional signaling pathways with critical functions in hES cells at low density, a small molecule library of compounds with known bioactivities was screened to identify those that negatively impact culture expansion and/or pluripotency. Inhibition of key pathways would be expected to result in slowed proliferation, cytotoxicity, apoptosis or differentiation in such an assay. Importantly, this screen was performed against the background of a simple defined medium, reducing inconsistencies typically introduced by undefined or variable components such as serum or semi-fractionated albumin. A simple alkaline phosphatase staining assay was used to determine ~50 compounds that impacted hES cell growth. Of these, numerous inhibitors of cell surface neurotransmitter receptors were identified, suggesting a signaling role for these receptors in self-renewal. Using naturally occurring ligands or pharmacologically related derivatives, several classes of small molecule neurotransmitters, which may also act as hormones or modulators, were found to support survival and/or expansion of hES cells grown at low density. Such activities could be crucial for developing advanced technologies for commercial and clinical application of hES cells, such as reliable single cell cloning, efficient derivation of new hES cell lines under fully defined and GMP-compliant conditions, growth of hES cells in suspension and enhanced viability upon passaging.

Definitions

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell, two cells, or a plurality of cells.

Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

"About" as used herein means that a number referred to as "about" comprises the recited number plus or minus 1-10% of that recited number. For example, about 50 nucleotides can mean 45-55 nucleotides or as few as 49-51 nucleotides depending on the situation. Whenever it appears herein, a numerical range, such as "45-55", refers to each integer in the given range; e.g., "45-55%" means that the percentage can be 45%, 46%, etc., up to and including 55%. Where a range described herein includes decimal values, such as "1.2% to 10.5%", the range refers to each decimal value of the smallest increment indicated in the given range; e.g. "1.2% to 10.5%" means that the percentage can be 1.2%, 1.3%, 1.4%, 1.5%, etc. up to and including 10.5%; while "1.20% to 10.50%" means that the percentage can be 1.20%, 1.21%, 1.22%, 1.23%, etc. up to and including 10.50%.

Manufacturing-scale suspension culture typically utilizes continuous perfusion of media as a method for maintaining cell viability while maximizing cell density. In this context, media exchange contributes fluid shear to the culture affecting adherent cells and suspended aggregates differently. Immobile adherent cells are subject to fluid shear stress as the media flows tangentially across the cell surface. In contrast, suspended aggregates experience significantly less shear stress across the aggregate surface, as aggregates are free to tumble in response to applied shear force. It is expected that prolonged shear stress will be detrimental to adherent ES cells and that a suspended aggregate format is preferred for optimal survival and function. Thus, based on a need for an efficient manufacturing process for production of pluripotent stem cells and/or multipotent progenitor cells derived from pluripotent stem cells in light of the above observed mechanics relating to shear rate and shear stress, the present invention provides, for the first time, methods of manufacturing for production of pluripotent stem cells and/or multipotent progenitor cells derived from pluripotent stem cells in a suspension format, and more particularly, in a cell aggregate suspension format.

As used herein, "single cell suspension" or equivalents expressions, refers to a mixture of a fluid and a cell, or more typically a plurality of cells, that are separated from each other (i.e. not aggregated), which can be prepared by any available mechanical, biological or chemical means. Single cell suspensions described herein are typically preparations of viable hES cells or hES-derived cells suspended in a physiological solution, such as a basal salt solution, saline, cell culture media, or the like. Several methods exist for dissociating cell clusters to form single cell suspensions from primary tissues, adherent cells in culture, and cell aggregates, including but not limited to, method that dissociate cells by physical forces (mechanical dissociation such as cell scraper, trituration through a narrow bore pipette, fine needle aspiration, vortex disaggregation and forced filtration through a fine nylon or stainless steel mesh), enzymes (enzymatic dissociation such as trypsin, collagenase, Accutase™ and the like), or combinations thereof. Further, methods and culture media conditions capable of supporting growth and viability of single-cell suspensions of hES cells are useful for expansion, cell sorting, and defined seeding for multi-well plate assays and enable automatization of culture procedures and clonal expansion. Thus, one embodiment of the invention provides methods for generating a stable single-cell enzymatic dissociation hES cell or hES-derived cell culture system capable of supporting long-term maintenance and efficient expansion of undifferentiated, pluripotent hES cell or differentiated hES cells.

As used herein, the term "contacting" (i.e., contacting a cell e.g., a differentiable cell, with a compound) is intended to include incubating the compound and the cell together in vitro (e.g., adding the compound to cells in culture). The term "contacting" is not intended to include the in vivo exposure of cells to a defined cell medium comprising components, compounds, growth factors and the like (e.g. a neurotransmitter, an ErbB3 ligand, a member of the TGF-β family, etc.), as they occur naturally in a subject (i.e., exposure that may occur as a result of a natural physiological process). For example, the step of contacting a cell with a defined cell medium that contains a neurotransmitter, an ErbB3 ligand, and a member of the TGF-β family, can be conducted in any suitable manner, but will be understood to expose the cell to contact with the aforementioned components. For example, the cells may be contacted by incubating (culturing) the cells with the component(s) in adherent culture or in suspension culture. It is understood that the cells contacted with the components in defined medium can be further treated with a cell differentiation environment to stabilize the cells, or to differentiate the cells.

"Support" as used herein in the context of cell culture, refers to media compositions and specific components thereof, that are sufficient for the desired growth, viability, pluripotency and/or other characteristics of the cell culture. Thus, a defined medium that supports undifferentiated expansion of hES cells is one in which the cells will grow without differentiation when the hES cells are cultured therein without additional factors, compounds, additives or the like. A compound or factor that supports the expansion of hES cells is one that, when added to the media conditions described, will allow the hES cells to grow.

As used herein, "defined cell culture media," "defined culture media," and "defined media" are used interchangeably to refer to aqueous compositions containing specific proportions, amounts or activities of inorganic and organic components (including biological and bioactive components) that can faithfully be reproduced with substantially similar properties. Defined media may contain proteins, preferably recombinant proteins, provided they can be prepared or purified without significant lot-to-lot or batch-to-batch variability. Animal sera are inherently undefined and variable, and therefore defined media does not include serum. However, individual, highly purified serum or other proteins, factors and the like may be included in defined media in an amount or proportion based on mass, molar equivalents or activity (e.g. measurable biological activity).

As used herein, the term "differentiate" refers to the production of a cell type that is more specialized than the cell type from which it is derived. The term therefore encompasses cell types that are partially and terminally differentiated. Differentiated cells derived from hES cells are generally referred to as "hES-derived cells," "hES-derived cell aggregate cultures," "hES-derived single cell suspensions," "hES-derived cell adherent cultures" and the like.

As used herein, the term "substantially" refers to a great extent or degree. For example, "substantially similar" in context can be used to describe a method which is to a great extent or degree similar to another method. However, as used herein, by the term "substantially free", (e.g., "substantially free" or "substantially free from contaminants," or "substantially free of serum" or "substantially free of insulin or insulin like growth factor" or equivalent expressions), it is meant that the solution, media, supplement, excipient or the like, is at least 80%, at least 85%, at least 90%, at least 95%, at least 99% or at least about 100% free of serum, contaminants or equivalent thereof. In one embodiment of the invention, there is provided a defined culture medium with no serum, or is 100% serum-free, or is substantially free of serum. In contrast, a "substantially similar" composition, process, method, solution, media, supplement, excipient or the like, is at least 80%, at least 85%, at least 90%, at least 95%, or at least 99% similar to the reference composition, process, method, solution, media, supplement, excipient previously described herein, or in a previously described process or method incorporated herein by reference in its entirety.

In certain embodiments of the present invention, the term "enriched" refers to a cell culture that contains more than approximately 50%, 55%, 60%, 65%, 70%, 75%, 80%, 85%, 90%, or 95% of a desired cell lineage.

As used herein, the term "effective amount" or equivalents expressions, of a compound refers to that amount of the compound that is sufficient in the presence of the remaining components to effect the desired result, such as stabilization of a pluripotent cell culture for greater than one month, two months, three months, four months, five months and/or six or greater months in the absence of a feeder cell and in the absence of serum or serum replacement. In other aspects of the invention, an "effective amount" or equivalents expressions of a compound can refer to that concentration of the compound that is sufficient in the presence of the remaining components to effect the stabilization of a pluripotent cell culture for greater than for greater than 5, 10, 15, 20, 25, 30 or 40 passages, in the absence of a feeder cell and in the absence of serum or serum replacement. Similarly, this concentration is readily determined by one of ordinary skill in the art.

As used herein, the term "express" refers to the transcription of a polynucleotide and/or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include without limitation, Northern blotting, RT-PCR, in situ hybridization, Western blotting, and immunostaining.

As used herein when referring to a cell, cell line, cell culture or population of cells, the term "isolated" refers to being substantially separated from the natural source of the cells such that the cell, cell line, cell culture, or population of cells are capable of being cultured in vitro. In addition, the term "isolating" is used to refer to the physical separation of one or more cells out of a group of two or more cells, where the cells are selected based on a desired characteristic, such as cell morphology and/or the expression of a marker.

The present invention may be understood more readily by reference to the following detailed description of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. See Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Lastly, abbreviations and nomenclature, where employed, are deemed standard in the field and commonly used in professional journals such as those cited herein.

The present invention is based on the Applicants' previous observations that defined culture media compositions (e.g. medium DC-HAIF) containing highly purified growth factors can be used to support the expansion of pluripotent stem cells in the absence of differentiation. The present invention provides defined culture media that includes small molecule organic compound(s) affecting signal transduction pathways important for viability, growth, pluripotency and self-renewal. Various pathways have been identified as important in this regard, by screening a library of pharmaceutically active compounds for those that reduce viability, growth or potency of hES cells. These compounds were categorized according to known action. The pathways identified included a large percentage mediated by neurotransmitter receptors. Specifically, many of the compounds identified as having a negative effect on pluripotent stem cell growth, were known antagonists of neurotransmitter receptors.

As used herein, "neurotransmitter" or "endogenous neurotransmitter" refers to any of a group of substances that are released upon excitation from the axon terminus of a presynaptic neuron and travel across the synaptic cleft to either excite or inhibit a target cell (e.g. a postsynaptic neuron, dendritic terminus). Neurotransmitters include small molecule compounds (i.e. ≤800 Daltons), such as monoamines and amino acids, as well as larger species, such as peptides. Common small molecule neurotransmitters include:

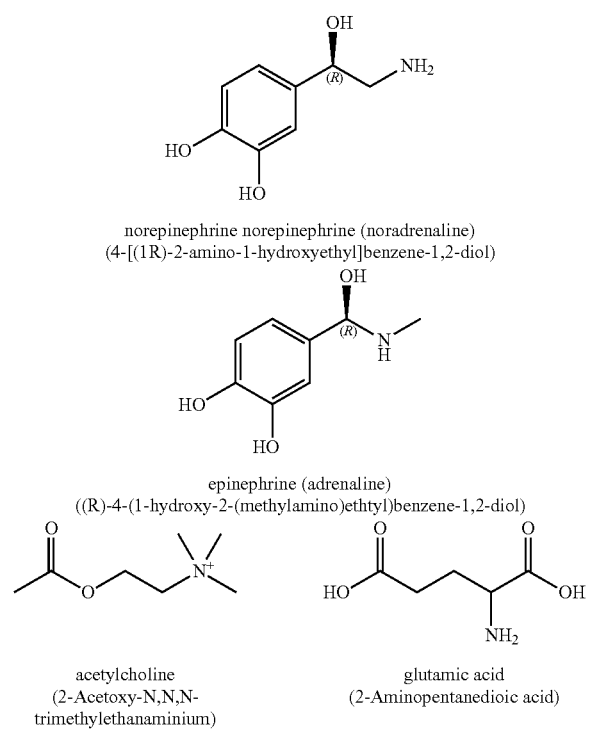

norepinephrine norepinephrine (noradrenaline)
(4-[(1R)-2-amino-1-hydroxyethyl]benzene-1,2-diol)

epinephrine (adrenaline)
((R)-4-(1-hydroxy-2-(methylamino)ethtyl)benzene-1,2-diol)

acetylcholine
(2-Acetoxy-N,N,N-trimethylethanaminium)

glutamic acid
(2-Aminopentanedioic acid)

-continued

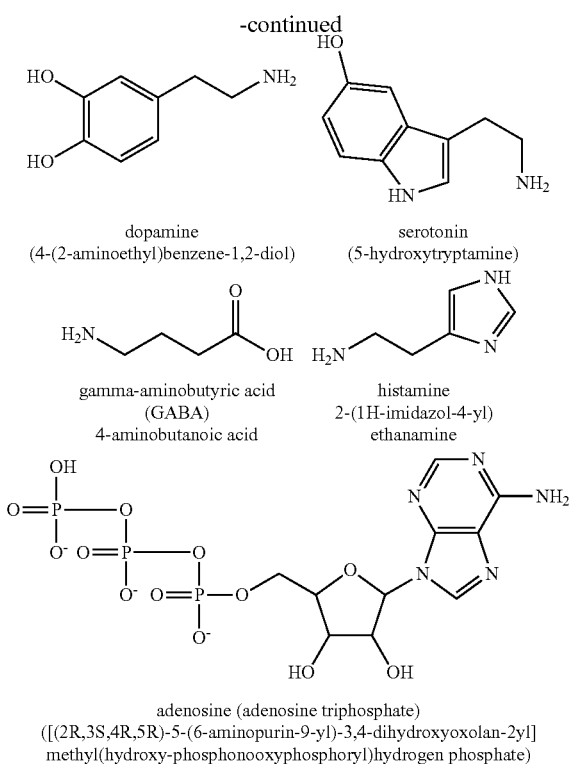

Neurotransmitters bind receptors on the target cell (i.e. "neurotransmitter receptors") that are typically 7-transmembrane G-protein-coupled receptors. Exemplary neurotransmitter receptors include: adrenergic, dopaminergic, glycinergic, glutaminergic, GABAergic, histaminergic, cholinergic, and serotonergic neurotransmitter receptors. Certain neurotransmitters may diffuse away from a synapse and influence multiple neurons in a process known as "neuromodulation," or behave as "hormones" on other cells or receptors. A large number of pharmaceutically active drugs are small molecule neurotransmitter receptor ligands, including agonists, antagonists, modulators and the like.

As used herein, "ligand" refers to a chemical that binds to a biological molecule, such as a receptor. As used herein, "agonist" refers to a ligand that binds to a receptor of a cell and triggers a response by the cell, while "antagonist" refers to a ligand that binds to a receptor and inhibits a response of a cell by blocking agonist binding.

To identify compounds having a positive effect on pluripotent stem cell growth, particularly at low cell density, a subset of a small molecule pharmaceutical compound library was screened for compounds having the ability to support hES growth at low cell density in the defined medium DC-HAIF. It was reasoned that if a neurotransmitter antagonist negatively impacted hES cell growth, then an agonist or endogenous ligand of the same receptor may positively impact the hES cells. As described below in Examples 2 and 3, a variety of compounds were identified that supported hES cell growth at low cell density. Specifically, the neurotransmitters norepinepherine, acetylcholine, dopamine, serotonin and adenosine were identified as candidates for supporting low density survival and expansion of pluripotent stem cells when added to a defined medium.

Thus, the present invention provides defined culture media including a basal salt nutrient solution, growth factors, and one or more neurotransmitters selected from norepinepherine, acetylcholine, dopamine, serotonin, and adenosine. Also encompassed by the invention are defined media including naturally occurring and synthetic small molecule agonists, antagonists, ligands and modulators of neurotransmitter receptors, including neurotransmitter derivatives, variants, metabolites, structural analogs, salts and the like. In one aspect of the invention, the medium is DC-HAIF and the neurotransmitter is norepinephrine. In other embodiments, the medium contains combination of two or more neurotransmitter. For example, under certain conditions, the combination of norepinephrine and acetylcholine was found to act synergistically to stimulate hES cell growth.

In certain embodiments of the invention, defined culture media compositions containing norepinepherine with simplified growth factor components are provided. Surprisingly, different growth factors could be replaced by norepinepherine and/or other small organic compounds, when hES cells were cultured therein at low cell density as compared to higher (standard) cell density. Specifically, Activin, previously found to be required at standard cell densities, was dispensable at low cell density and could be replaced with norepinepherine at higher cell density.

A used herein, "standard cell density" refers to a concentration range of pluripotent stem cells typically known to be viable and capable of expansion in culture. For example, hES cells are typically plated at a density of about $1 \times 10^5$ to about $5 \times 10^5$ cells per ml and are divided or passaged when they reach a density of about $2.5 \times 10^6$ to about $5 \times 10^7$ cells per ml. In contrast, "low cell density" refers to pluripotent stem cells plated at a cell density that is significantly less than the standard cell density. It is well known in the art that cells plated below a certain threshold density may experience a lag in cell division or may fail to survive passaging. Cultures of hES cells plated at about $5 \times 10^4$ or fewer cells per ml considered to be of low cell density.

In certain embodiments, pluripotent cells are cultured in the defined media described herein in the absence and/or presence of extracellular matrix proteins (ECM), e.g., MATRIGEL™. Pluripotent cells cultured in the absence of ECM contain about 0.5 to 10% human serum (hS) or hS retentate fractions from a 300K and/or 100K MW cut-off spin column (Microcon®, Millipore, Billerica, Mass.). The hES cell aggregate suspensions can be produced by directly incubating the hES cells into the media containing hS or hS retentate fractions; or after incubating the culture vessels with the hS or hS retentate fractions for about 30 min., 1 hour, 2 hours, 3 hours, 4, hours, 5 hours, 6 hours, 12 hours, or 24 hours at 37° C. The plating efficiency for the pluripotent cells in the hS or hS retentate fraction containing media was comparable to that observed in hES cells cultured in DC-HAIF as described in PCT/US2007/062755, or cultured in DC-HAIF media using MATRIGEL™ as an ECM, or other similar matrices. Methods for culturing hES cells in a defined media substantially free of serum are described in U.S. Patent Publication No. 2009/0104696, Apr. 23, 2009, entitled METHODS AND COMPOSITIONS FOR FEEDER-FREE PLURIPOTENT STEM CELL MEDIA CONTAINING HUMAN SERUM, which is herein incorporated in its entirety by reference.

Still in other embodiments, pluripotent cells, either as a monolayer or as an aggregate suspension, are cultured in a medium substantially free of serum and further in the absence of exogenously added fibroblast growth factor (FGF). Such methods are is distinguishable from U.S. Pat. No. 7,005,252 to Thomson, J., which requires culturing hES cells in a media without serum but containing exogenously added growth factors, including FGF.

As used herein, the term "differentiable cell" is used to describe a cell or population of cells that can differentiate into at least partially mature cells, or that can participate in the differentiation of cells, e.g., fuse with other cells, that can differentiate into at least partially mature cells. As used herein, "at least partially mature cells", includes progenitor cells, precursor cells, multipotent cells, immature cells, as well as those that are terminally differentiated. At least partially mature cells include e.g., definitive endoderm cells, PDX1-negative foregut endoderm cells, PDX1-positive pancreatic endoderm cells which further include PDX1-positive pre-pancreatic endoderm cells and PDX1-positive pancreatic endoderm tip cells, or PDX1/NKX6.1 co-positive or PDX1/PTF1A co-positive pancreatic endoderm cells, NGN3/NKX2.2 co-positive cells positive and multi- or singly-hormonal secreting pancreatic cells. All are cells that exhibit at least one characteristic of the phenotype, such as morphology or protein expression, of a mature cell from the same organ or tissue even though some can further differentiate into at least one other cell type.

Still other methods describe making embryoid bodies (EBs). As used herein, the term "embryoid bodies", "aggregate bodies" or equivalents expressions, refer to aggregates of differentiated and undifferentiated cells that appear when ES cells overgrow in monolayer cultures, or are maintained in suspension cultures in undefined media or are differentiated via non-directed protocols towards multiple germ layer tissues. That is, EBs are not formed from a single cell suspension of pluripotent stem cells as described herein; nor are EBs formed from adherent cultures of hES-derived multipotent cells. These features alone make the present invention clearly distinguished from an embryoid body.

Embryoid bodies are a mixture of different cell types, typically from several germ layers, distinguishable by morphological criteria. The determination of when embryoid bodies have formed in a culture of embryonic stem cells is routinely made by persons of skill in the art by, for example, visual inspection of the morphology. Floating masses of about 20 cells or more depending on the culture conditions are considered to be EBs. See, e.g., Schmitt et al. (1991) Genes Dev. 5, 728-740; Doetschman et al. (1985) J. Embryol. Exp. Morph. 87, 27-45. The term also refers to equivalent structures derived from primordial germ cells, which are primitive cells extracted from embryonic gonadal regions; see, e.g., Shamblott, et al. (1998) Proc. Natl. Acad. Sci. USA 95, 13726. Primordial germ cells, sometimes also referred to in the art as EG cells or embryonic germ cells, when treated with appropriate factors form pluripotent ES cells from which embryoid bodies can be derived; see, e.g., U.S. Pat. No. 5,670,372; and Shamblott, et al., supra.

Various methods for making EBs exist, e.g. spin embryoid bodies as described by Ng et a. (2008) Nature Protocols 3(5): 468-776 and EBs made from single cell suspensions which were plated onto micro-patterned extracellular matrix islands as described in Bauwens et al (2008) supra. However, these methods are cost-prohibitive and less efficient for large scaled production (manufacturing) of hES cells and hES-derived cells because they require too many steps before scale-up production can actually commence. For example, Bauwens et al., first have to seed hES cells on a growth factor reduced MATRIGEL™ before the cells can be selected to start a suspension culture. The time and cost of this method makes it cumbersome because customized micro-patterned tissue culture plates are required. Additionally, the method employed by Ng et al. is also not cost-efficient for large scale-up manufacturing of hES cells and hES-derived cells because of the use of centrifuges in order to create a more uniform EB. Lastly, in all these methodologies, the cell aggregates are not made from single cell suspensions of pluripotent stem cells as the present invention.

Embryoid bodies are cell aggregates that are made up of numerous cell types from the three germ layers and are typically created by exposing aggregates of undifferentiated ES cells to non-directed differentiation signals, such as 20% fetal bovine serum. This is in contrast to the suspension cell aggregates described in this invention, The result of this non-directed methodology is a mixture of cell types that is intended to mimic normal embryo development in vitro. While this approach is useful at the basic research level for examining embryo development, it is not amenable to any large-scale cell therapy manufacturing process where cell yield, population identity, population purity, batch consistency, safety, cell function and cost of goods are primary concerns. Moreover, regardless of any enrichment strategies employed to purify a given cell type from an embryoid body, the differentiation protocol does not provide a directed approach that will generate a large population of a single cell types. Subsequently, contaminant populations will always predominate and will hamper any attempt to purify a specific population.

All previously reported work on creating and differentiating aggregates of pluripotent cells has one or more of the following components in their methodology: 1) use of mouse rather than human ES cells; 2) forced aggregation protocols that rely on centrifugation to aggregate cells rather than normal cell adhesion processes; 3) aggregation of cell chunks under static conditions; 4) non-single cell dissociation or scraping of cells off surfaces to create aggregates; 5) Non-direct differentiation of cell aggregates using 15-20% fetal calf serum, resulting in the formation of an embryoid body and cell types of all germ layers. To applicants' knowledge, the only reported study in which 15-20% FCS is not used to differentiate embryoid bodies, involves a protocol where cell aggregates are formed by forced aggregation and then the formed aggregates are immediately differentiated using media appropriate for mesoderm (Ng et al., Blood. 2005 106(5):1601). However, in this report, the researchers transferred the embryoid bodies to non-aggregate adherent culture after 10-12 days in static aggregate culture, making comparisons to the current application irrelevant.

In contrast, the current application presents an approach for producing single cell aggregates that 1) dissociates human ES cells to single cells then creates aggregates by rotational culture at shear rates optimized for improved control of aggregate diameter and cell survival, and then allows 2) direct differentiation of the ES cell aggregates, for example, to definitive endoderm, followed by foregut endoderm, then pre-pancreatic foregut endoderm, then pancreatic endoderm and finally pancreatic endocrine cells. This differentiation protocol generates definitive endoderm and pancreatic lineage populations with high efficiency and minimal contaminant populations. Moreover, this approach to pluripotent cell aggregation and differentiation does not create embryoid bodies, in direct contrast to all other published research.

In one particular embodiment, the undifferentiated as well as the differentiable cells are expanded in a suspension culture, using the cell culture media of the present invention. In another particular embodiment, the differentiable cells can be maintained and expanded in suspension, i.e., they remain undifferentiated or are prevented from further differentiating. The terms "expand," "expanded" and "expansion" in the context of cell culture are used as they are in the art, and refer to cellular proliferation and increase in the number of cells, preferably increase in number of viable cells. In a specific embodiment, the cells are expanded in a culture suspension by culturing for more than about one day, i.e., about 24 hours. In a more specific embodiment, the cells are expanded in a suspension culture by culturing for at least 1, 2, 3, 4, 5, 6, 7 days or more, or at least 2, 3, 4, 5, 6, 7, 8 weeks or more.

The invention contemplates compositions and methods useful for differentiable cells, regardless of their source or of their plasticity. The "plasticity" of a cell is used herein roughly as it is in the art. Namely, the plasticity of a cell refers to a cell's ability to differentiate into a particular cell type found in tissues or organs from an embryo, fetus or developed organism. The "more plastic" a cell, the more tissues into which the cell may be able to differentiate.

In some embodiments, a "pluripotent cell" is used as the starting material for differentiation to endoderm-lineage, or more particularly, to pancreatic endoderm type cells. As used herein, "pluripotent," "pluripotency," "pluripotent cells" and equivalents expressions refer to cells that are capable of both proliferation and self-renewal in cell culture and differentiation towards a variety of cell populations that include those that exhibit multipotent properties, for example, pluripotent ES cell can give rise to each of the three embryonic cell lineages. Pluripotent cells, however, cannot give rise to extra-embryonic tissues such as the amnion, chorion, and other components of the placenta, and may not be capable of producing an entire organism, i.e. pluripotent cells are not "totipotent". Pluripotency can be demonstrated by providing evidence of stable developmental potential, to form derivatives of all three embryonic germ layers from the progeny of a single cell and to generate a teratoma after injection into an immunosuppressed mouse. Other indications of pluripotency include expression of genes known to be expressed in pluripotent cells and, characteristic morphology. The pluripotent cells of the present invention can be derived using any method known to those of skill in the art.

"Totipotent" as used herein, refers to the ability of a cell to develop into all types of cells, including extraembryonic tissues (e.g. placenta) and to give rise to an entire organism (e.g. a mouse or human).

"Self-renewal" refers to the ability of a stem cell to divide and form more stem cells with properties identical to the parent stem cell, thereby allowing the population of stem cells to be replenished indefinitely.

In certain embodiments, the pluripotent cells used as starting material are stem cells, including hES cells, hEG cells, iPS cells, even parthenogenic cells and the like. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. Still in another embodiment, pluripotent cells are not derived or are not immediately derived from embryos, for example, iPS cells are derived from a non-pluripotent cell, e.g., a multipotent cell or terminally differentiated cell, through a process known as "dedifferentiation" or "reprogramming." As used herein, "dedifferentiation" or "reprogramming" refers to refers to the process by which a differentiated cell reverts to a less specialized precursor, progenitor or stem cell state.

As used herein, "multipotency" or "multipotent cell" or equivalents thereof refers to a cell type that can give rise to a limited number of other particular cell types. That is, multipotent cells are committed to one or more embryonic cell fates, and thus, in contrast to pluripotent cells, cannot give rise to each of the three embryonic cell lineages as well as to extraembryonic cells. Multipotent somatic cells are more differentiated relative to pluripotent cells, but are not terminally differentiated. Pluripotent cells therefore have a higher potency than multipotent cells. Potency-determining factors that can reprogram somatic cells or be used to generate iPS cells include, but are not limited to, factors such as Oct-4, Sox2, FoxD3, UTF1, Stella, Rex1, ZNF206, Sox15, Myb12, Lin28, Nanog, DPPA2, ESG1, Otx2 or combinations thereof.

One aspect of the present invention includes populations of pluripotent or precursor cells that are capable of selectively, and in some aspects selectively reversibly, developing into different cellular lineages when cultured under appropriate conditions. As used herein, the term "population" refers to cell culture of more than one cell having the same identifying characteristics. The term "cell lineage" refers to all of the stages of the development of a cell type, from the earliest precursor cell to a completely mature cell (i.e. a specialized cell). A "precursor cell" or "progenitor cell" can be any cell in a cell differentiation pathway that is capable of differentiating into a more mature cell. As such, a precursor cell can be a pluripotent cell, or it can be a partially differentiated multipotent cell, or reversibly differentiated cell. The term "precursor cell population" refers to a group of cells capable of developing into a more mature or differentiated cell type. A precursor cell population can comprise cells that are pluripotent, cells that are stem cell lineage restricted (i.e. cells capable of developing into less than all ectodermal lineages, or into, for example, only cells of neuronal lineage), and cells that are reversibly stem cell lineage restricted. Therefore, the term "progenitor cell" or "precursor cell" may be a "pluripotent cell" or "multipotent cell."

As used herein, the terms "develop", "differentiate", "mature" or "produced from pluripotent cells", "derived from pluripotent cells", "differentiated from pluripotent cells" and equivalent expressions refer to the production of a differentiated or more specialized cell type e.g. from pluripotent cells in vitro or in vivo, or in the case of endocrine cells matured from transplanted PDX1 pancreatic endoderm cells in vivo as described in International Application PCT/US2007/015536, titled METHODS OF PRODUCING PANCREATIC HORMONES, which is herein incorporated by reference in its entirety. All refer to the progression of a cell from the stage of having the potential to differentiate into at least two different cellular lineages through specialization and eventually terminally differentiation. Such terms can be used interchangeably for the purposes of the present application. The invention contemplates culture conditions that permit such differentiation to be reversible, such that pluripotency or at least the ability to differentiate into more than one cellular lineage can be selectively regained.

The invention also contemplates differentiable cells from any source within an animal, provided the cells are differentiable as defined herein. For example, differentiable cells may be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In specific embodiments, the differentiable cells are embryonic stem cells. In other specific embodiments, the differentiable cells are adult stem cells. In still other specific embodiments, the stem cells are placental- or chorionic-derived stem cells.

Of course, the invention contemplates using differentiable cells from any animal capable of generating differentiable cells. The animals from which the differentiable cells are harvested may be vertebrate or invertebrate, mammalian or non-mammalian, human or non-human. Examples of animal sources include, but are not limited to, primates, rodents, canines, felines, equines, bovines and porcines.

In certain embodiment, when pluripotent cells are utilized, the pluripotent cells have a normal karyotype, e.g., greater than 50%, 55%, 60%, 65%, 70%, 75%, 80%, 85%, 90% or greater than 95% of the pluripotent cell culture of metaphases examined will display a normal karyotype.

The compositions and methods comprise a basal salt nutrient solution. As used herein, basal salt nutrient solution refers to an aqueous solution of salts that provide cells with water and certain bulk inorganic ions essential for normal cell metabolism and maintain intra- and extra-cellular osmotic balance; carbohydrate as an energy source; and a buffering system to maintain the medium within the physiological pH range. Examples of basal salt nutrient solutions include, but are not limited to, Dulbecco's Modified Eagle's Medium (DMEM), Minimal Essential Medium (MEM), Basal Medium Eagle (BME), RPM1 1640, Ham's F-10, Ham's F-12, α-Minimal Essential Medium (aMEM), Glasgow's Minimal Essential Medium (G-MEM), Iscove's Modified Dulbecco's Medium, or a general purpose media modified for use with pluripotent cells, such as X-VIVO (Lonza) hematopoeitic base media and mixtures thereof. In one particular embodiment, the basal salt nutrient solution is an approximately 50:50 mixture of DMEM and Ham's F12.

Although a basal salt nutrient solution as described herein is employed to maintain cell growth and viability of pluripotent cells, in other embodiments of the invention, alternative pluripotent stem cell culture media to maintain pluripotency or for differentiation of the pluripotent cells, work in substantially similar means, including but not limited to KSR (Invitrogen), or xeno-free KSR (Invitrogen), StemPro® hESC SFM (Life Technologies), mTeSR™ 1 (StemCell Technologies) and HES cellGRO (Millipore), DMEM and X Vivo (Lonza) based media, and the like.

It is contemplated that the composition can further comprise trace elements. Trace elements can be purchased commercially, for example, from Mediatech. Non-limiting examples of trace elements include but are not limited to compounds comprising, aluminum, chlorine, sulfate, iron, cadmium, cobalt, chromium, germanium, sodium, potassium, calcium, phosphate and magnesium. Specific example of compounds containing trace elements include but are not limited to, $AlCl_3$, $AgNO_3$, $Ba(C_2H_3O_2)_2$, $CdCl_2$, $CdSO_4$, $CoCl_2$, $CrCl_3$, $Cr_2(SO_4)_3$, $CuSO_4$, ferric citrate, $GeO_2$, KI, KBr, LI, molybdic acid, $MnSO_4$, $MnCl_2$, NaF, $Na_2SiO_3$, $NaVO_3$, $NH_4VO_3$, $(NH_4)_6Mo_7O_{24}$, $NiSO_4$, RbCl, selenium, $Na_2SeO_3$, $H_2SeO_3$, selenite.2Na, selenomethionone, $SnCl_2$, $ZnSO_4$, $ZrOCl_2$, and mixtures and salts thereof. If selenium, selenite or selenomethionone is present, it is at a concentration of approximately 0.002 to approximately 0.02 mg/L. In addition, hydroxylapatite may also be present.

It is contemplated that amino acids can be added to the defined media. Non-limiting examples of such amino acids are Glycine, L-Alanine, L-Alanyl-L-Glutamine, L-Glutamine/Glutamax, L-Arginine hydrochloride, L-Asparagine-$H_2O$, L-Aspartic acid, L-Cysteine hydrochloride-$H_2O$, L-Cystine 2HCl, L-Glutamic Acid, L-Histidine hydrochloride-$H_2O$, L-Isoleucine, L-Leucine, L-Lysine hydrochloride, L-Methionine, L-Phenylalanine, L-Proline, L-Hydroxyproline, L-Serine, L-Threonine, L-Tryptophan, L-Tyrosine disodium salt dihydrate, and L-Valine. In certain embodiments, the amino acid is L-Isoleucine, L-Phenylalanine, L-Proline, L-Hydroxyproline, L-Valine, and mixtures thereof.

It is also contemplated that the defined medium can comprise ascorbic acid. Preferably ascorbic acid is present at an initial concentration of approximately 1 mg/L to approximately 1000 mg/L, or from approximately 2 mg/L to approximately 500 mg/L, or from approximately 5 mg/L to approximately 100 mg/L, or from approximately 10 mg/L to approximately 100 mg/L or approximately at 50 mg/L.

In addition, the compositions and methods may also comprise other components such as serum albumin, transferrin, L-glutamine, lipids, antibiotics, β-Mercaptoethanol, vitamins, minerals, ATP and similar components may be present. Examples of vitamins that may be present include, but are not limited to vitamins A, $B_1$, $B_2$, $B_3$, $B_5$, $B_6$, $B_7$, $B_9$, $B_{12}$, C, $D_1$, $D_2$, $D_3$, $D_4$, $D_5$, E, tocotrienols, $K_1$ and $K_2$. One of skill in the art can determine the optimal concentration of minerals, vitamins, ATP, lipids, essential fatty acids, etc., for use in a given culture. The concentration of supplements may, for example, be from about 0.001 µM to about 1 mM or more. Specific examples of concentrations at which the supplements may be provided include, but are not limited to about 0.005 µM, 0.01 µM, 0.05 µM, 0.1 µM, 0.5 µM, 1.0 µM, 2.0 µM, 2.5 µM, 3.0 µM 4.0 µM, 5.0 µM, 10 µM, 20 µM, 100 µM, etc. In one specific embodiment, the compositions and methods comprise vitamin $B_6$ and glutamine. In another specific embodiment, the compositions and methods comprise vitamin C and an iron supplement. In another specific embodiment, the compositions and methods comprise vitamin $K_1$ and vitamin A. In another specific embodiment, the compositions and methods comprise vitamin $D_3$ and ATP. In another specific embodiment, the compositions and methods comprise vitamin $B_{12}$ and transferrin. In another specific embodiment, the compositions and methods comprise tocotrienols and β-Mercaptoethanol. In another specific embodiment, the compositions and methods comprise glutamine and ATP. In another specific embodiment, the compositions and methods comprise an omega-3 fatty acid and glutamine. In another specific embodiment, the compositions and methods comprise an omega-6 fatty acid and vitamin $B_1$. In another specific embodiment, the compositions and methods comprise α-linolenic acid and $B_2$.

The compositions of the present invention are essentially serum free. As used herein, "essentially" refers to compositions, formulations, methods and the like that are fundamentally or in effect the same as the quantity or quality stated, allowing for minor contaminants and/or insignificant changes. In general, essentially refers to at least about 95%, at least about 96%, at least about 97%, at least about 98%, at least about 99%, at least about 99.5%, or 100% the same. Thus, "essentially serum free" refers to the absence of serum, or fundamentally or in effect the absence of serum in the solutions of the present invention. Serum is not an essential ingredient to the compositions and methods of the present invention. Thus, the presence of serum in any of the compositions should only be attributable to impurities, e.g., from the starting materials or residual serum from the primary cell culture. For example, essentially serum free medium or environment can contain less than 5, 4, 3, 2, 1 or 0.5% serum wherein the presently improved bioactive maintenance capacity of the medium or environment is still observed. In a specific embodiment of the present invention, the essentially serum free composition does not contain serum or serum replacement, or only contains trace amounts of serum or serum replacement from the isolation of components of the serum or serum replacement that are added to the defined media.

As used herein, a "functional fragment" is a fragment or splice variant of a full length polypeptide that exerts a similar physiological or cellular effect as the full length polypeptide. The biological effect of the functional fragment need not be identical in scope or strength as the full-length polypeptide, so long as a similar physiological or cellular effect is seen. For example, a functional fragment of the ErbB2 ligand, HRG-β can detectably stimulate ErbB2-directed tyrosine kinase.

As used herein, the term "variant" includes chimeric or fusion polypeptides, homologs, analogs, orthologs, and paralogs, e.g., variants of norepinephrine, dopamine and acetylcholine, particularly structural analogs, are within the scope of the present invention. In addition, a variant of a reference protein or polypeptide is a protein or polypeptide whose amino acid sequence is at least about 80% identical to the reference protein or polypeptide. In specific embodiments, the variant is at least about 85%, 90%, 95%, 95%, 97%, 98%, 99% or even 100% identical to the reference protein or polypeptide.

As used herein in the context of small molecule compounds, such as naturally-occurring neurotransmitters and synthetic ligands of neurotransmitter receptors, the term "analog" refers to compounds that share structural and/or functional similarity. Analogs include "structural analogs", which possess structural similarities; and "functional analogs" which are chemically different compounds displaying similar pharmacological properties.

As used herein, the terms "correspond(s) to" and "corresponding to," as they relate to sequence alignment, are intended to mean enumerated positions within the reference protein or polypeptide, e.g., wild-type human or mouse neuregulin-1, and those positions in the modified protein or polypeptide that align with the positions on the reference protein or polypeptide. Thus, when the amino acid sequence of a subject protein or polypeptide is aligned with the amino acid sequence of a reference protein or polypeptide, the sequence that "corresponds to" certain enumerated positions of the reference protein or polypeptide sequence are those that align with these positions of the reference sequence, but are not necessarily in these exact numerical positions of the reference sequence. Methods for aligning sequences for determining corresponding amino acids between sequences are described below.

A polypeptide having an amino acid sequence at least, for example, about 95% "identical" to a reference an amino acid sequence encoding, for example TGF-β, is understood to mean that the amino acid sequence of the polypeptide is identical to the reference sequence except that the amino acid sequence may include up to about five modifications per each 100 amino acids of the reference amino acid sequence encoding the reference TGF-β, or aforementioned small molecule neurotransmitters such as nor-epinephrine, dopamine or acetylcholine. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exists several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at the 5' or 3' ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/ aligned with the query. In this case the percent identity calculated by FASTDB is not manually corrected.

The invention also provides chimeric or fusion polypeptides. As used herein, a "chimeric polypeptide" or "fusion polypeptide" comprises at least a portion of a member of the reference polypeptide operatively linked to a second, different polypeptide. The second polypeptide has an amino acid sequence corresponding to a polypeptide which is not substantially identical to the reference polypeptide, and which is derived from the same or a different organism. With respect to the fusion polypeptide, the term "operatively linked" is intended to indicate that the reference polypeptide and the second polypeptide are fused to each other so that both sequences fulfill the proposed function attributed to the sequence used. The second polypeptide can be fused to the N-terminus or C-terminus of the reference polypeptide. For example, in one embodiment, the fusion polypeptide is a GST-IGF-1 fusion polypeptide in which an IGF-1 sequence is fused to the C-terminus of the GST sequences. Such fusion polypeptides can facilitate the purification of recombinant polypeptides. In another embodiment, the fusion polypeptide can contain a heterologous signal sequence at its N-terminus. In certain host cells (e.g., mammalian host cells), expression and/or secretion of a polypeptide can be increased through use of a heterologous signal sequence.

In addition to fragments and fusion polypeptides, the present invention includes homologs and analogs of naturally occurring polypeptides. "Homologs" are defined herein as two nucleic acids or polypeptides that have similar, or "identical," nucleotide or amino acid sequences, respectively. Homologs include allelic variants, orthologs, paralogs, agonists, and antagonists as defined hereafter. The term "homolog" further encompasses nucleic acid molecules that differ from a reference nucleotide sequence due to degeneracy of the genetic code and thus encode the same polypeptide as that encoded by the reference nucleotide sequence. As used herein, "naturally occurring" refers to a nucleic or amino acid sequence or other molecular species that occurs in nature.

An agonist of a polypeptide can retain substantially the same, or a subset, of the biological activities of the polypeptide. An antagonist of a polypeptide can inhibit one or more of the activities of the naturally occurring form of the polypeptide.

Certain compositions and methods of the present invention comprise a means for stimulating ErbB2 tyrosine kinase activity within differentiable cells. In one specific embodiment, the compositions and methods of the present invention comprise the presence of at least one ErbB3 ligand. Typically, an ErbB3 ligand will bind the ErbB3 receptor and dimerize with the ErbB2 receptor. The ErbB2 receptor is, in turn, generally responsible for intracellular tyrosine kinase activity within the differentiable cell.

As used herein, "ErbB3 ligand" refers to a ligand that binds to ErbB3, which in turn dimerizes to ErbB2, thus activating the tyrosine kinase activity of the ErbB2 portion of the ErbB2/ErbB3 heterodimeric receptor. Non-limiting examples of ErbB3 ligands include Neuregulin-1; splice variants and isoforms of Neuregulin-1, including but not limited to Heregulin-β (HRG-β), Heregulin-α (HRG-α), Neu differentiation factor (NDF), acetylcholine receptor-inducing activity (ARIA), glial growth factor 2 (GGF2), sensory and motor neuron-derived factor (SMDF); Neuregulin-2; splice variants and isoforms of Neuregulin-2, including but not limited to NRG2-β; Epiregulin; and Biregulin.

In certain embodiments, the means for stimulating ErbB2-directed tyrosine kinase activity includes at least one ErbB3 ligand that is selected from the group consisting of Neuregulin-1, Heregulinβ (HRG-β), Heregulin-α (HRG-α), Neu differentiation factor (NDF), acetylcholine receptor-inducing activity (ARIA), glial growth factor 2 (GGF2), sensory and motor-neuron derived factor (SMDF), Neuregulin-2, Neuregulin-2β (NRG2-β), Epiregulin, Biregulin and variants and functional fragments thereof. In another specific embodiment, the compositions and methods of the present invention comprise more than one means for stimulating ErbB2-directed tyrosine kinase activity, such as, but not limited to, using more than one ErbB3 ligand.

In a more specific embodiment of the compositions and methods of the present invention, the ErbB3 ligand is HRG-β or a variant or functional fragment thereof. In one embodiment, the species from which the culture additive protein, polypeptide or variant or functional fragment thereof derives is the same as the species of cells that are cultured. For example, if mouse ES cells are cultured, an HRG-β with an amino acid sequence that is identical to the mus musculus HRG-β sequence can be used as an additive in culture and is considered to be "of the same species." In other embodiments, the species from which the biological additive derives is different from the cells being cultures. For example, if mouse ES cells are cultured, an HRG-β with an amino acid sequence that is identical to the human HRG-β sequence from can be used as an additive in culture and is considered to be "of different species" or "xenographic."

In one embodiment of the present invention, the compositions and methods are free of exogenous insulin and insulin substitutes. The phrase "exogenous insulin or insulin substitutes" is used herein to indicate insulin or insulin substitutes that is/are not intentionally added to the compositions or methods of the present invention. Thus, in certain embodiments of the present invention, the methods and compositions are free of insulin or insulin substitutes that are intentionally supplied. The compositions or methods may, however, not necessarily be free of endogenous insulin. As used herein, "endogenous insulin" indicates that the cultured cells may be producing insulin of their own accord when cultured according to the methods of the present invention. Endogenous insulin also may be used to indicate residual impurities from the primary cell culture or impurities from the starting materials. In specific examples, the compositions and methods of the present contain less than 50, 45, 40, 35, 30, 25, 20, 15, 10, 9, 8, 7, 6, 5, 4, 3, 2, or 1 µg/ml of insulin.

As used herein, the term "insulin" refers to the protein, or variant or fragment thereof that binds to the insulin receptor in normal physiological concentrations and can induce signaling through the insulin receptor. The term "insulin" encompasses a protein having the polypeptide sequence of native human insulin, or of other mammalian insulin, or of any homologs or variants to these sequences. Additionally, the term insulin encompasses polypeptide fragments that are capable of binding to the insulin receptor to induce signaling through the insulin receptor. The term "insulin substitute" refers to any zinc containing compound that may be used in place of insulin to give substantially similar results as insulin. Examples of insulin substitutes include, but are not limited to zinc chloride, zinc nitrate, zinc bromide, and zinc sulfate.

To be clear, insulin-like growth factors are not insulin substitutes or homologs of insulin, as contemplated in the present invention. Accordingly, in another specific embodiment, the compositions and methods of the present invention comprise the use of at least one insulin-like growth factor (IGF) or a variant or a functional fragment thereof. In another embodiment, the compositions and methods of the present invention are free of any exogenous insulin-like growth factors (IGFs). In specific embodiments, the compositions and methods of the present invention contain less than 200, 150, 100, 75, 50, 25, 20, 15, 10, 9, 8, 7, 6, 5, 4, 3, 2, or 1 ng/ml of IGF-1.

As used herein, the term "activator of IGF-1R" refers to mitogens that play a pivotal role in regulating cell proliferation, differentiation, and apoptosis. The effects of an activator of IGF-1R are typically mediated through IGF-1R, although they can be mediated through other receptors. The IGF-1R is also involved in cell transformation induced by tumor virus proteins and oncogene products, and the interaction is regulated by a group of specific binding proteins (IGFBPs). In addition, a large group of IGFBP proteases hydrolyze IGFBPs, resulting in the release of bound IGFs that then resume their ability to interact with IGF-IR. For the purpose of this invention, the ligands, the receptors, the binding proteins, and the proteases are all considered to be activators of IGF-1R. In one embodiment, the activator of IGF-1R is IGF-1, or IGF-2. In a further embodiment, the activator of IGF-1R is an IGF-1 analog. Non-limiting examples of IGF-1 analogs include LongR3-IGF1, Des(1-3)IGF-1, [Arg$^3$]IGF-1, [Ala$^{31}$]IFG-1, Des(2,3)[Ala$^{31}$]IGF-1, [Leu$^{24}$]IGF1, Des(2,3)[Leu$^{24}$]IGF-1, [Leu$^{60}$]IGF-1, [Ala$^{31}$][Leu$^{60}$]IGF-1, [Leu$^{24}$][Ala$^{31}$]IGF-1, and combinations thereof. In a further embodiment, the IFG-1 analog is LongR3-IGF1, which is a recombinant analog of human insulin growth factor-1. It is contemplated that LongR3-IGF1 is initially present at a concentration of approximately 1 ng/ml to approximately 1000 ng/ml, more preferably approximately 5 ng/ml to approximately 500 ng/ml, more preferably approximately 50 ng/ml to approximately 500 ng/ml, more preferably approximately 100 ng/ml to approximately 300 ng/ml, or at a concentration of approximately 100 ng/ml.

In certain embodiments, the compositions and methods of the present invention include transforming growth factor beta (TGF-β) or a TGF-β family member or variants or functional fragments thereof. As used herein, the term "member of the TGF-β family" or the like refers to growth factors that are generally characterized by one of skill in the art as belonging to the TGF-β family, either due to homology with known members of the TGF-β family, or due to similarity in function with known members of the TGF-β family. In particular embodiments of the invention, if the member of the TGF-β family is present, the TGF-β family member of variant or functional fragment thereof activates SMAD 2 or 3. In certain embodiments, the member of the TGF-β family is selected from the group consisting of Nodal, Activin A, Activin B, TGF-β, bone morphogenic protein-2 (BMP2), GDF-8, GDF-11 and bone morphogenic protein-4 (BMP4) to name a few. In one embodiment, the member of the TGF-β family is Activin A, Activin B, Nodal, GDF-8 and GDF.

It is contemplated that if Nodal is present, it is initially present at a concentration of approximately 0.1 ng/ml to approximately 2000 ng/ml, more preferably approximately 1 ng/ml to approximately 1000 ng/ml, more preferably approximately 10 ng/ml to approximately 750 ng/ml, or more preferably approximately 25 ng/ml to approximately 500 ng/ml. It is contemplated that if used, Activin A is initially present at a concentration of approximately 0.01 ng/ml to approximately 1000 ng/ml, more preferably approximately 0.1 ng/ml to approximately 100 ng/ml, more preferably approximately 0.1 ng/ml to approximately 25 ng/ml, or most preferably at a concentration of approximately 10 ng/ml. It is contemplated that if present, TGF-β is initially present at a concentration of approximately 0.01 ng/ml to approximately 100 ng/ml, more preferably approximately 0.1 ng/ml to approximately 50 ng/ml, or more preferably approximately 0.1 ng/ml to approximately 20 ng/ml.

In additional embodiments of the present invention, the compositions and methods of the present invention are free of activators of FGF receptors. As used herein, the term "activator of an FGF receptor" refers to growth factors that are generally characterized by one of skill in the art as belonging to the FGF family, either due to homology with known members of the FGF family, or due to similarity in function with known members of the FGF family. In certain embodiments, the activator of an FGF receptor is an FGF, such as, but not limited to α-FGF and FGF2. In particular embodiments, the compositions and methods are free of exogenous FGF2. The phrase "exogenous FGF2" is used herein to indicate fibroblast growth factor 2, i.e., basic FGF that is not intentionally added to the compositions or methods of the present invention. Thus, in certain embodiments of the present invention, the methods and compositions are free of intentionally supplied FGF2. The compositions or methods may, however, not necessarily be free of endogenous FGF2. As used herein, "endogenous FGF2" indicates that the cultured cells may be producing FGF2 of their own accord when cultured according to the methods of the present invention. "Endogenous FGF2" also may be used to indicate residual impurities from the primary cell culture or impurities from the starting materials. In specific examples, the compositions and methods of the present invention contain less than 10, 9, 8, 7, 6, 5, 4, 3, 2, or 1 ng/ml of FGF2.

It is contemplated, however, that the compositions and methods of the invention can include at least one activator of an FGF receptor, including any of the FGF polypeptides, functional fragments thereof or variants thereof. It is contemplated that if FGF2 is present, it is initially present at a concentration of approximately 0.1 ng/ml to approximately 100 ng/ml, more preferably approximately 0.5 ng/ml to approximately 50 ng/ml, more preferably approximately 1 ng/ml to approximately 25 ng/ml, more preferably approximately 1 ng/ml to approximately 12 ng/ml, or most preferably at a concentration of approximately 8 ng/ml. In another specific embodiment, the compositions and methods of the invention can include at least one activator of an FGF receptor, other than FGF2. For example, the compositions and methods of the present invention may comprise at least one of FGF-7, FGF-10 or FGF-22 or variants or functional fragments thereof. In specific embodiments, a combination of at least two of FGF-7, FGF-10 and FGF-22, or variants or functional fragments thereof, are present. In another embodiment, all three of FGF-7, FGF-10 and FGF-22, or variants or functional fragments thereof, are present. It is contemplated that if any of FGF-7, FGF-10 or FGF-22 or variants or functional fragments are present, each is initially present at a concentration of approximately 0.1 ng/ml to approximately 100 ng/ml, more specifically from approximately 0.5 ng/ml to approximately 50 ng/ml, more specifically from approximately 1 ng/ml to approximately 25 ng/ml, more specifically from approximately 1 ng/ml to approximately 12 ng/ml, or most specifically at a concentration of approximately 8 ng/ml.

In certain additional embodiments, the compositions and methods of the present invention include serum albumin (SA). In specific embodiments, the SA is either bovine SA (BSA) or preferably human SA (HAS). In still more specific embodiments, the concentration of the SA is more than about 0.2%, volume to volume (v/v), but less than about 10% v/v. In even more specific embodiments, the concentration of SA is more than about 0.3%, 0.4%, 0.5%, 0.6%, 0.7%, 0.8%, 0.9%, 1.0%, 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 4.2%, 4.4%, 4.6%, 4.8%, 5.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6% and 9.8% (v/v).

Accordingly, the cell culture environments and methods of the present invention comprise plating the cells in an adherent culture. As used herein, the terms "plated" and "plating" refer to any process that allows a cell to be grown in adherent culture. As used herein, the term "adherent culture" refers to a cell culture system whereby cells are cultured on a solid surface, which may in turn be coated with an insoluble substrate that may in turn be coated with another surface coat of a substrate, such as those listed below, or any other chemical or biological material that allows the cells to proliferate or be stabilized in culture. The cells may or may not tightly adhere to the solid surface or to the substrate. The substrate for the adherent culture may comprise any one or a combination of polyornithine, laminin, poly-lysine, purified collagen, gelatin, fibronectin, tenascin, vitronectin, entactin, heparin sulfate proteoglycans, poly glycolytic acid (PGA), poly lactic acid (PLA), and poly lactic-glycolic acid (PLGA). Furthermore, the substrate for the adherent culture may comprise the matrix laid down by a feeder layer, or laid down by the pluripotent human cell or cell culture. As used herein, the term "extracellular matrix" encompasses solid substrates such as but not limited to those described above, as well as the matrix laid down by a feeder cell layer or by the pluripotent human cell or cell culture. In one embodiment, the cells are plated on MATRIGEL™-coated plates. In another embodiment, the cells are plated on fibronectin-coated plates. In certain embodiments, if the cells are plated on fibronectin, the plates are prepared by coating with 10 µg/ml human plasma fibronectin (Invitrogen, #33016-015), diluted in tissue grade water, for 2-3 hours at room temperature. In another embodiment, serum can be placed in the medium for up to 24 hours to allow cells to plate to the plastic. If using serum to promote the attachment of the cells, the media is then removed and the compositions, which are essentially serum-free, are added to the plated cells.

The compositions and methods of the present invention contemplate that the differentiable cells are cultured in conditions that are essentially free of a feeder cell or feeder layer. As used herein, a "feeder cell" is a cell that grows in vitro, that is co-cultured with a target cell. When present, feeder cells may fulfill essential cell density requirements of a target cell, provide a substrate or cell-cell interactions for the target cell, condition the cell culture medium, and/or stabilize the target cell in its current state of differentiation. As used herein, a "feeder cell layer" can be used interchangeably with the term "feeder cell." As used herein, the term "essentially free of a feeder cell" refers to tissue culture conditions that do not contain feeder cells, or that contain a de minimus number of feeder cells. By "de minimus", it is meant that the number of feeder cells that are carried over to the instant culture conditions from previous culture conditions where the differentiable cells may have been cultured on feeder cells. In one embodiment of the above method, conditioned medium is obtained from a feeder cell that stabilizes the target cell in its current state of differentiation. In another embodiment, the defined medium is a non-conditioned medium, which is a medium that is not obtained from a feeder cell.

As used herein, the term "stabilize," when used in reference to the differentiation state of a cell or culture of cells, indicates that the cells will continue to proliferate over multiple passages in culture, and preferably indefinitely in culture, where most, if not all, of the cells in the culture are of the same differentiation state. In addition, when the stabilized cells divide, the division typically yields cells of the same cell type or yields cells of the same differentiation state. A stabilized cell or cell population in general, does not further differentiate or de-differentiate if the cell culture conditions are not altered, and the cells continue to be passaged and are not overgrown. In one embodiment, the cell that is stabilized is capable of proliferation in the stable state indefinitely, or for at least more than 2 passages. In a more specific embodiment, the cells are stable for more than 3 passages, 4 passages, 5 passages, 6 passages, 7 passages, 8 passages, 9 passages, more than 10 passages, more than 15 passages, more than 20 passages, more than 25 passages, or more than 30 passages. In one embodiment, the cell is stable for greater than approximately 1 month, 2 months, 3 months, 4 months, 5 months, 6 months, 7 months, 8 months, 9 months, 10 months, or 11 months of continuous passaging. In another embodiment, the cell is stable for greater than approximately 1 year of continuous passaging. In one embodiment, stem cells are maintained in culture in a pluripotent state by routine passage in the defined medium until it is desired that they be differentiated. As used herein, the term "proliferate" refers to an increase in the number cells in a cell culture.

In certain embodiments, the compositions and methods comprise an inactivator of BMP signaling. As used herein, an "inactivator of BMP signaling" refers to an agent that antagonizes the activity of one or more BMP proteins or any of their upstream or downstream signaling components through any of its possible signaling pathways. The compound(s) used to inactivate BMP signaling can be any compound known in the art, or later discovered. Non-limiting examples of inactivators of BMP signaling include dominant-negative, truncated BMP receptor, soluble BMP receptors, BMP receptor-Fc chimeras, noggin, follistatin, chordin, gremlin, cerberus/DAN family proteins, ventropin, high dose activin, and amnionless.

In certain embodiments, the compositions and methods of the inventioncan comprise at least one hormone, cytokine, adipokine, growth hormone or variant or functional fragment thereof. It is currently contemplated that in certain embodiments, the growth hormone present in the defined medium will be of the same species as the differentiable cells that are cultured with the defined media. Thus, for example, if a human cell is cultured, the growth hormone is human growth hormone. The use of growth hormone that is from a species different than the cultured cells is also contemplated. Preferably the hormone, cytokine, adipokine and/or growth hormone is present at an initial concentration of approximately 0.001 ng/ml to approximately 1000 ng/ml, more preferably approximately 0.001 ng/ml to approximately 250 ng/ml, or more preferably approximately 0.01 ng/ml to approximately 150 ng/ml.

Examples of cytokines and adipokines that may be included in the compositions and methods of the present invention include, but are not limited to, the four α-helix bundle family of cytokines, the interleukin-1 (IL-1) family of cytokines, the IL-17 family of cytokines and the chemokine family of cytokines. Of course, the invention contemplates members and subclasses of each of these families of cytokines, such as, but not limited to, the CC chemokines, the CXC chemokines, the C chemokines and the $CX_3C$ chemokines, interferons, interleukins, lymphotoxins, c-kit ligand, granulocyte-macrophage colony-stimulating factor (GM-CSF), monocyte-macrophage colony-stimulating factor (M-CSF), granulocyte colony-stimulating factor (G-CSF), leptin, adiponectin, resistin, plasminogen activator inhibitor-1 (PAI-1), tumor necrosis factor-alpha (TNFα), tumor necrosis factor-beta (TNFβ), leukemia inhibitory factor, visfatin, retinol binding protein 4 (RBP4), erythropoietin (EPO), thrombopoietin (THPO). Of course, one of skill in the art will understand that the invention contemplates variants or functional fragments of the above-listed factors.

The present invention relates to methods of culturing differentiable cells, with the methods comprising plating differentiable cells on a cell culture surface, providing a basal salt nutrient solution to the cells and providing a means for stimulating ErbB2-directed tyrosine kinase activity in the cells.

In one embodiment, differentiable cells are contacted with at least one of the compositions of the invention in the absence of serum or serum replacement, and in the absence of a feeder cell layer, such that the cells are maintained in an undifferentiated state for at least one month. Pluripotency can be determined through characterization of the cells with respect to surface markers, transcriptional markers, karyotype, and ability to differentiate to cells of the three germ layers. These characteristics are well known to those of ordinary skill in the art.

The term "suspension" as used in the context of cell culturing is used as it is in the art. Namely, cell culture suspensions are cell culture environments where the cells or cell aggregates do not adhere to a surface. One of skill in the art will be familiar with suspension culture techniques, including, but not limited to, the use of equipment such as flow hoods, incubators and/or equipment used to keep the cells in constant motion, e.g., rotator platforms, shakers, etc, if necessary. As used herein, cells are "in motion" if they are moving, or if their immediate environment is moving relative to the cells. If the cells are kept "in motion", the motion will, in one embodiment, be a "gentle motion" or "gentle agitation" that is designed to avoid or prevent exposing the cells to shear stress.

A variety of methods of making cell aggregates are known in the art such as, for example, the "hanging drop" method wherein cells in an inverted drop of tissue culture medium sink to the bottom of the drop where they aggregate; shaking cell suspensions in a laboratory flask; and various modifications of these techniques. See, e.g., N. E. Timmins, et al. (2004) Angiogenesis 7, 97-103; W. Dai, et al., (1996) Biotechnology and Bioengineering 50, 349-356; R. A. Foty, et al. (1996) Development 122, 1611-1620; G. Forgacs, et al. (2001) J. Biophys. 74, 2227-2234 (1998); K. S. Furukawa, et al., Cell Transplantation 10, 441-445; R. Glicklis, et al. (2004) Biotechnology and Bioengineering 86, 672-680; Carpenedo et al., (2007) Stem Cells 25, 2224-2234; and T. Korff, et al., (2001) FASEB J. 15, 447-457, which are herein incorporated in their entirety be reference. More recently, cell aggregates have been formed by scraping micropatterned colonies into suspension, centrifuging colonies out of microtiter plates and into suspension or using pipets to dislodge and suspend colonies grown in patterned microwells (Ungrin et al., (2008) PLoS ONE 3(2), 1-12; Bauwens et al (2008) Stem Cells Published online Jun. 26, 2008). Although such methods can be used to produce cell aggregates described herein, the cell aggregates produced herein are optimized for synchronous directed-differentiation as described in d'Amour et al. Nat Biotechnol 24:1392-401, 2006. Also, unlike these other methods, the methods for producing the cell aggregates in suspension described herein are amenable to large scale manufacturing.

In general, the cell medium compositions of the present invention are refreshed at least once every day, but the medium can be changed more often or less often, depending of the specific needs and circumstances of the suspension culture. In vitro, cells are usually grown in culture media in a batch mode and exposed to various media conditions. As described herein, the cells exist in a dish-culture as either adherent cultures or as cell aggregates in suspension, and maintained in contact with a surrounding culture medium; and the waste media being replaced periodically. In general, the culture medium may be refreshed about every 1, 2, 3, 4, 5, 6, 7, 8, 9, 10, 11, 12, 13, 14, 15, 16, 17, 18, 19, 20, 21, 22, 23 or 24 hours, or any fraction thereof. In additional examples, the medium may be refreshed less often such as, but not limited to, every 1.1, 1.2, 1.3, 1.4, 1.5, 1.6, 1.7, 1.8, 1.9 or every 2 or more days, or any time frame in between.

Yet, in another embodiment of the invention, perfusion methods are employed to prevent degradation of growth factors and other agents which have to be replaced frequently; or perfusion is used as a means to deplete waste products from the culture media over a period of time. For example, U.S. Pat. No. 5,320,963 describes a bioreactor for perfusion culture of suspension cells. U.S. Pat. No. 5,605,822 describes a bioreactor system, employing stromal cells to provide growth factors, for growth of HSC cells in culture by perfusion. U.S. Pat. No. 5,646,043 describes growth of HSC cells by continuous and periodic perfusion including media compositions for growth of HSC cells. U.S. Pat. No.

5,155,035 describes a bioreactor for suspension culture of cells by fluid media rotation. These references are all incorporated herein in their entireties.

In general, the cells that are cultured in suspension in the medium compositions of the present invention are "split" or "passaged" every week or so, but the cells can be split more often or less often, depending on the specific needs and circumstances of the suspension culture. For example, the cells may be split every 1, 2, 3, 4, 5, 6, 7, 8, 9, 10, 11, 12, 13, 14 or more days, or any time frame in between. As used herein, the term "split" or "passaged" in the context of cell culture is used as it is in the art. Namely, cell culture splitting, or passaging, is the collection of cells from a previous culture and subsequent transfer ("seeding") of a smaller number of collected (harvested) cells into a new cell culture vessel. In general, passaging cells allows the cells to continue to grow in a healthy cell culture environment. One of skill in the art will be familiar with the process and methods of cell culture passaging, which may, but not necessarily, involve the use of enzymatic or non-enzymatic methods that may be used to disaggregate cells that have clumped together during their growth expansion.

In some instances, a degree of cell death may occur in the cultured (suspended and adherent) cells immediately after passaging. In one embodiment, the differentiable cells can "recover" from passaging, by delaying the refreshing of the cell medium for more than 24 hours. Thereafter, the cell medium may be changed more frequently. In another embodiment, the cell culture medium can further comprise an inhibitor of cell death. For example, Wantanabe et al., recently disclosed the use of a Rho-associated kinase inhibitor, Y27632, to protect human ES cells after dissociation. See Wantanabe, K., et al., *Nat. Biotechnol.*, 25(6):681-686 (2007), which is incorporated by reference. In additional embodiments, the cell culture medium may comprise caspase inhibitors, growth factors or other trophic factors to prevent or attenuate cell death immediately after passaging. Specific examples of compounds that may be used include, but are not limited to, HA 1077, Dihydrochloride, Hydroxyfasudil, Rho Kinase Inhibitor, Rho-Kinase Inhibitor II, Rho Kinase Inhibitor III, Kinase Inhibitor IV and Y27632 all of which are commercially available. In still another embodiment, the compounds or factors used to prevent or attenuate cell death during or immediately after cell passaging may be removed from the cell culture medium after the cells have recovered from the passaging process. In an additional embodiment, undifferentiated ES cells aggregate effectively in standard base media and do not require Y27632 or other interventions to maintain viability during dissociation and aggregation.

In additional embodiments, the compositions and methods of the present invention may also comprise the presence or use of surfactants. In one particular embodiment, the compositions and methods comprise at least one surfactant in the context of a suspension culture. Surfactants are well-known in the art and, generally speaking, are amphiphilic in nature. In specific embodiments, the present invention comprises the use of at least one surfactant that is either anionic, cationic, non-ionic or zwitterionic. The concentration of the surfactant used in the compositions and methods of the present invention is a matter of routine screening and optimization. For example, Owen et al., reported the use of surfactants in cell culture techniques for HeLa cells and human amniotic cells. See Owen et al., *J. Cell. Sci.*, 32:363-376 (1978), which is incorporated by reference. Examples of surfactants that may be used include, but are not limited to, sodium dodecyl sulfate (SDS), ammonium lauryl sulfate, and other alkyl sulfate salts, sodium laureth sulfate (SLES), alkyl benzene sulfonate, soaps, or fatty acid salts, cetyl trimethylammonium bromide (CTAB) (hexadecyl trimethyl ammonium bromide), and other alkyltrimethylammonium salts, cetylpyridinium chloride (CPC), polyethoxylated tallow amine (POEA), benzalkonium chloride (BAC), benzethonium chloride (BZT), dodecyl betaine, dodecyl dimethylamine oxide, Cocamidopropyl betaine, coco ampho glycinate, alkyl poly(ethylene oxide), copolymers of poly (ethylene oxide) and poly(propylene oxide) such as Pluronic® F68, alkyl polyglucosides, such as, but not limited to, octyl glucoside, decyl maltoside, fatty alcohols, cetyl alcohol, oleyl alcohol, cocamide MEA, cocamide DEA and cocamide TEA and/or polyoxyethylene-sorbitane monolaurate (Tween®).

The embodiments described herein provide methods for large-scale manufacturing of proliferating and/or differentiating hES cells by maintaining a low shear environment thereby maintaining operating cell density in the system and minimizing fluid shear stresses. In particular, the present invention provides methods for maintaining a low shear environment in a eukaryotic cell manufacturing scale-up system by culturing a cell suspension in a 60 mm dish, 6-well plate, a rotating bottle, a bioreactor (e.g., large and spinner flasks), a vessel, closed loop systems and the like. Alternatively, continuous perfusion systems for culturing cells requires agitation or movement in the bioreactor or vessel to provide suspension of the cells, oxygenation and a supply of fresh nutrients, e.g., for growth and/or differentiation. To obtain cell suspension, bioreactor vessels typically use one or more movable mechanical agitation devices that are also a potential source of shear stress.

It is contemplated that the differentiable cells can be passaged using enzymatic, non-enzymatic, or manual dissociation methods prior to and/or after contact with the defined media of the invention. Manual passaging techniques have been well described in the art, such as in Schulz et al., 2004 Stem Cells, 22(7):1218-38. Although mechanical passaging does not involve any additional substances, it is not efficient for large-scale manufacturing of pluripotent cells or cells derived thereof. For example, in bioreactors or large flasks, use of enzymes is contemplated, using for example GMP-collagenase. Non-limiting examples of enzymatic dissociation methods include the use of proteases such as trypsin, collagenase, dispase, and ACCUTASE™ (Life Technologies, Carlsbad, Calif.). In one embodiment, ACCUTASE™ is used to passage the contacted cells. When enzymatic passaging methods are used, the resultant culture can comprise a mixture of singlets, doublets, triplets, and clumps of cells that vary in size depending on the enzyme used. A non-limiting example of a non-enzymatic dissociation method is a cell dispersal buffer. The choice of passaging method is influenced by the choice of extracellular matrix, if one is present, and is easily determined by one of ordinary skill in the art.

The disaggregation solution used in the methods of the present invention can be any disaggregation solution capable of breaking apart or disaggregating the cells into single cells, without causing extensive toxicity to the cells. Examples of disaggregation solutions include, but are not limited to, trypsin, ACCUTASE™, 0.25% Trypsin/EDTA, TrypLE, or VERSENE™ (EDTA) and trypsin. The methods of the present invention need not result in every cell of the confluent layer or suspension being disaggregated into single cells, provided that at least a few single cells are disaggregated and capable of being re-cultured.

Either at the beginning of culture, or after passaging, the differentiable cells can be seeded at any density, including a single cell in a culture chamber. The cell density of the seeded cells may be adjusted depending on a variety of factors, including but not limited to the use of adherent or suspension cultures, the specific recipe of the cell culture media used, the growth conditions and the contemplated use of the cultured cells. Examples of cell culture densities include, but are not limited to, $0.01\times10^5$ cells/ml, $0.05\times10^5$ cells/ml, $0.1\times10^5$ cells/ml, $0.5\times10^5$ cells/ml, $1.0\times10^5$ cells/ml, $1.2\times10^5$ cells/ml, $1.4\times10^5$ cells/ml, $1.6\times10^5$ cells/ml, $1.8\times10^5$ cells/ml, $2.0\times10^5$ cells/ml, $3.0\times10^5$ cells/ml, $4.0\times10^5$ cells/ml, $5.0\times10^5$ cells/ml, $6.0\times10^5$ cells/ml, $7.0\times10^5$ cells/ml, $8.0\times10^5$ cells/ml, $9.0\times10^5$ cells/ml, or $10.0\times10^5$ cells/ml, or more, e.g., up to $5\times10^7$ cells/mlml have been cultured with good cell survival, or any value in between.

In addition to the above, as used herein, the term "operating cell density" or "operational cell density" or equivalent expressions refers to that cell density at which a manufacturing process or system will be operated to obtain the production of a proliferating or differentiating hES cell culture. Such cell densities are those at which nutrients such as vitamins, minerals, amino acids or metabolites, as well as environmental conditions such as oxygen tension, that are supplied to the system are sufficient to maintain cellular viability. Alternatively, such cell densities are those at which waste products can be removed from the system at a rate sufficient to maintain cellular viability. Such cell densities can be readily determined by one of ordinary skill in the art.

Operating cell densities that may be maintained are those from at least about $0.5\times10^6$ cells/ml. In a typical scale-up system operating cell densities may be between about $0.5\times10^6$ cells/ml and about $25\times10^6$ cells/ml. Exemplary densities can be between about $2.5\times10^6$ cells/ml, $25\times10^6$ cells/ml and up to $5\times10^7$ cells/ml. In the method of the invention, cell viability is at least about 40%, 45%, 50%, 55%, 60%, 65%, 70%, 75%, 80%, 85%, 90%, 95% and up to about 100%. Other scale-up system operating cell densities and acceptable cell viability levels will be recognized by those skilled in the art and can be determined by techniques well known to those of skill in the art. For example, in batch, fed-batch and continuous feed configurations, cell densities may be between about $0.5\times10^6$ cells/ml and $15\times10^6$ cells/ml.

Furthermore, pluripotent cells can also be grown in 96-well culture devices that provide real-time measurements of impedance, which can be used to measure cell proliferation and viability using the RT-CES™ methods from ACEA Biosciences, Inc. (www(dot)Aceabio(dot)com). Such an approach would enable a label-free identification and quantification of subtle or immediate effects on differentiable cells, as well as measurements of proliferation, apoptosis and changes to morphology, in real time.

Additionally, freezing and cryo-storage and thawing processes are optimally of GMP standard. Both vitrification and conventional slow cooling/rapid warming have been employed to cryo-preserve pluripotent cells, at least hES cells. See Hunt C. J., et al., Methods Mol. Biol. (2007) 368:261-270. Richards et al. (2004) described a xeno-free cryopreservation protocol for hES cells involving vitrification in closed sealed straws and use of human serum albumin as opposed to fetal calf serum as the main protein source in the cryoprotectant. See Richards M., et al., Stem Cells (2004) 22:779-789. Instead of straws, Fujioka et al. (2004) cryopreserved primate ES cells by means of a vitrification using cryovials, with survival rates of 6.5% for monkey ES cells and 12.2% for human ES cells. See Fujioka T., et al., Int. J. Dev. Biol. (2004) 48:1149-1154. Accordingly, one embodiment of the present invention relates to properly freezing and cryo-preserving or cryo-storage of pluripotent cells.

Monitoring the Production of Multipotent or Differentiated Cells

The progression of pluripotent cells to multipotent cells to further multipotent cells or differentiated cells can be monitored by measuring and quantifying the level of expression of certain gene markers, such as detecting the presence or absence of a specific gene marker at different time points before and after addition of an exogenous agent, for example, a TGF-β signaling agent. Alternatively, the expression of certain markers can be determined by measuring the level at which the marker is present in the cells of the cell culture or cell population. For example, in certain processes, the expression of markers characteristic of pluripotent cells as well as the lack of significant expression of markers characteristic of multipotent or differentiated cells is determined.

As described in connection with monitoring the production of other less differentiated cell types of the definitive endoderm lineage, qualitative or semi-quantitative techniques, such as blot transfer methods and immunocytochemistry (ICC) or immunohistochemistry (IHC), can be used to measure marker expression. Alternatively, marker expression can be accurately quantitated through the use of technique such as Q-PCR. Additionally, it will be appreciated that at the polypeptide level, many of the markers of pancreatic islet hormone-expressing cells are secreted proteins. As such, techniques for measuring extracellular marker content, such as ELISA, may be utilized.

The developmental progression of the pluripotent cells described herein (e.g., cells produced as a result of Stages or Steps 1-5 as described in D'Amour et al. 2006, supra) can be monitored by determining the expression of markers characteristic of each pluripotent-derived cell type along the developmental pathway. For example, in some processes, the identification and characterization of a pluripotent-derived cell type is by expression of a certain marker or different expression levels and patterns of more than one marker. That is, the presence or absence, the high or low expression, of one or more of the marker(s) typifies and identifies a cell-type. Also, certain markers can have transient expression, whereby the marker is highly expressed during one stage of development and poorly expressed in another stage of development. The expression of certain markers can be determined by measuring the level at which the marker is present in the cells of the cell culture or cell population as compared to a standardized or normalized control marker. In such processes, the measurement of marker expression can be qualitative or quantitative. One method of quantifying the expression of markers that are produced by marker genes is through the use of quantitative PCR (Q-PCR). Methods of performing Q-PCR are well known in the art.

In still other embodiments, Q-PCR can be used in conjunction with immunohistochemical techniques or flow cytometry techniques to effectively and accurately characterize and identify cell types and determine both the amount and relative proportions of such markers in a subject cell type. In one embodiment, Q-PCR can quantify levels of RNA expression in a cell culture containing a mixed population of cells. However, Q-PCR cannot provide or qualify whether the subject markers or proteins are co-expressed on the same cell. In another embodiment, Q-PCR is used in conjunction with flow cytometry methods to characterize and identify cell types. Thus, by using a combination of the methods described herein, and such as those described above, complete characterization and identification of various cell types, including endoderm lineage type cells, can be accomplished and demonstrated.

Still, other methods which are known in the art can also be used to quantitate marker gene expression. For example, the expression of a marker gene product can be detected by using antibodies specific for the marker gene product of interest (e.g., e.g. Western blot, flow cytometry analysis, and the like). In certain processes, the expression of marker genes characteristic of pluripotent-derived cells as well as the lack of significant expression of marker genes characteristic of pluripotent-derived cells can be detected. Still further methods for characterizing and identifying pluripotent-derived cells types are described in related applications as indicated above, which are herein incorporated by reference in their entirety.

Amplification probe/primer combinations suitable for use in amplification assays include the following: Amplification probe/primer combinations suitable for use in amplification assays include the following: Insulin (INS) (GenBank NM_000207): primers AAGAGGCCATCAAGCAGATCA (SEQ ID NO: 1); CAGGAGGCGCATCCACA (SEQ ID NO: 2); Nkx6.1 (NM_006168): primers CTGGCCTGTAC-CCCTCATCA (SEQ ID NO: 3); CTTCCCGTCTTTGTC-CAACAA (SEQ ID NO: 4); Pdx1 (NM_000209): primers AAGTCTACCAAAGCTCACGCG (SEQ ID NO: 5); GTAGGCGCCGCCTGC (SEQ ID NO: 6); Ngn3 (NM_020999): primers GCTCATCGCTCTCTAT-TCTTTTGC (SEQ ID NO: 7); GGTTGAGGCGTCATC-CTTTCT (SEQ ID NO: 8); FOXA2 (HNF3B) (NM_021784): primers GGGAGCGGTGAAGATGGA (SEQ ID NO: 9); TCATGTTGCTCACGGAGGAGTA (SEQ ID NO: 10); Glucagon (GCG) (NM_002054): primers AAGCATTTACTTTGTGGCTGGATT (SEQ ID NO: 11); TGATCTGGATTTCTCCTCTGTGTCT (SEQ ID NO: 12); HNF6 (NM_030712): primers CGCTCCGCTTAGCAG-CAT (SEQ ID NO: 13); GTGTTGCCTCTATCCTTCCCAT (SEQ ID NO: 14); HNF4Alpha (NM_000457): primers GAAGAAGGAAGCCGTCCAGA (SEQ ID NO: 15); GACCTTCGAGTGCTGATCCG (SEQ ID NO: 16); Sox17 (NM_022454): primers GGCGCAGCAGAATCCAGA (SEQ ID NO: 17); HLxB9 (NM_005515): primers CAC-CGCGGGCATGATC (SEQ ID NO: 19); ACTTCCCCAG-GAGGTTCGA (SEQ ID NO: 20); Nkx2.2 (NM_002509): primers GGCCTTCAGTACTCCCTGCA (SEQ ID NO: 21); GGGACTTGGAGCTTGAGTCCT (SEQ ID NO: 22); PTF1a (NM_178161): primers GAAGGTCATCATCTGC-CATCG (SEQ ID NO: 23) GGCCATAATCAGGGTCGCT (SEQ ID NO: 24); SST (NM_001048): primers CCCCA-GACTCCGTCAGTTTC (SEQ ID NO: 25); TCCGTCTG-GTTGGGTTCAG (SEQ ID NO: 26); PAX6 (NM_000280): primers CCAGAAAGGATGCCTCATAAAGG (SEQ ID NO: 27); TCTGCGCGCCCCTAGTTA (SEQ ID NO: 28); Oct4 primers: TGGGCTCGAGAAGGATGTG (SEQ ID NO: 29) GCATAGTCGCTGCTTGATCG (SEQ ID NO: 30); MIXL1 primers CCGAGTCCAGGATCCAGGTA (SEQ ID NO: 31) CTCTGACGCCGAGACTTGG (SEQ ID NO: 32); GATA4 primers CCTCTTGCAATGCGGAAAG (SEQ ID NO: 33) CGGGAGGAAGGCTCTCACT (SEQ ID NO: 34); GSC primers GAGGAGAAAGTGGAGGTCTG-GTT (SEQ ID NO: 35) CTCTGATGAGGACCGCTTCTG (SEQ ID NO: 36); CER primers ACAGTGCCCTTCAGC-CAGACT (SEQ ID NO: 37) ACAACTACTTTTTCACA-GCCTTCGT (SEQ ID NO: 38); AFP primers GAGAAAC-CCACTGGAGATGAACA (SEQ ID NO: 39) CTCATGGCAAAGTTCTTCCAGAA (SEQ ID NO: 40); SOX1 primers ATGCACCGCTACGACATGG (SEQ ID NO: 41) CTCATGTAGCCCTGCGAGTTG (SEQ ID NO: 42); ZIC1 primers CTGGCTGTGGCAAGGTCTTC (SEQ ID NO: 43) CAGCCCTCAAACTCGCACTT (SEQ ID NO: 44); NFM primers ATCGAGGAGCGCCACAAC (SEQ ID NO: 45) TGCTGGATGGTGTCCTGGT (SEQ ID NO: 46). Other primers are available though ABI Taqman including FGF17 (Hs00182599_m1), VWF (Hs00169795_m1), CMKOR1 (Hs00604567_m1), CRIP1 (Hs00832816_g1), FOXQ1 (Hs00536425_s1), CALCR (Hs00156229_m1) and CHGA (Hs00154441_m1).

Screening Methods Employing Pluripotent Suspension Aggregation Cultures

In some embodiments screening methods are employed to obtain certain cell populations comprising pluripotent, multipotent and/or differentiated cells. The cell population is then provided with a candidate differentiation factor. At a first time point, which is prior to or at approximately the same time as providing the candidate differentiation factor, expression of a marker is determined. Alternatively, expression of the marker can be determined after providing the candidate differentiation factor. At a second time point, which is subsequent to the first time point and subsequent to the step of providing the candidate differentiation factor to the cell population, expression of the same marker is again determined. Whether the candidate differentiation factor is capable of promoting the differentiation of the pancreatic precursor cells is determined by comparing expression of the marker at the first time point with the expression of the marker at the second time point. If expression of the marker at the second time point is increased or decreased as compared to expression of the marker at the first time point, then the candidate differentiation factor is capable of promoting the differentiation of pancreatic progenitor cells.

In embodiments of the screening methods described herein, the cell population is contacted or otherwise provided with a candidate (test) differentiation factor. The candidate differentiation factor can comprise any molecule that may have the potential to promote the differentiation of any of the above-mentioned cells. In alternate embodiments, the candidate differentiation factor comprises a molecule that in not known to promote cell differentiation. In preferred embodiments, the candidate differentiation factor comprises a molecule that is not known to promote the differentiation of human pancreatic progenitor cells.

In some embodiments of the screening methods described herein, the candidate differentiation factor comprises a small molecule. "Small molecule" is used herein as it is in the art to refer to low molecular weight organic compounds, which are by definition not polymers. Small molecules can be naturally occurring (such as endogenous neurotransmitters) or can be prepared by synthetic organic chemistry methods known in the art. In certain embodiments, a small molecule is a molecule having a molecular mass of about 800 daltons or less.

In other embodiments described herein, the candidate differentiation factor comprises a large molecule, e.g., a polypeptide. The polypeptide can be any polypeptide including, but not limited to, a glycoprotein, a lipoprotein, an extracellular matrix protein, a cytokine, a chemokine, a peptide hormone, an interleukin or a growth factor. Preferred polypeptides include growth factors.

In some embodiments of the screening methods described herein, the candidate differentiation factors comprise one or more growth factors selected from the group consisting of Amphiregulin, B-lymphocyte stimulator, IL-16, Thymopoietin, TRAIL/Apo-2, Pre B cell colony enhancing factor, Endothelial differentiation-related factor 1 (EDF1), Endothelial monocyte activating polypeptide II, Macrophage migration inhibitory factor (MIF), Natural killer cell enhancing factor (NKEFA), Bone morphogenetic protein 2, Bone morphogenetic protein 8 (osteogeneic protein 2), Bone morphogenic protein 6, Bone morphogenic protein 7, Connective tissue growth factor (CTGF), CGI-149 protein (neuroendocrine differentiation factor), Cytokine A3 (macrophage inflammatory protein 1-alpha), Gliablastoma cell differentiation-related protein (GBDR1), Hepatoma-derived growth factor, Neuromedin U-25 precursor, Vascular endothelial growth factor (VEGF), Vascular endothelial growth factor B (VEGF-B), T-cell specific RANTES precursor, thymic dendritic cell-derived factor 1, Transferrin, Interleukin-1 (IL 1), Interleukin-2 (IL 2), Interleukin-3 (IL 3), Interleukin-4 (IL 4), Interleukin-5 (IL 5), Interleukin-6 (IL 6), Interleukin-7 (IL 7), Interleukin-8 (IL 8), Interleukin-9 (IL 9), Interleukin-10 (IL 10), Interleukin-11 (IL 11), Interleukin-12 (IL 12), Interleukin-13 (IL 13), Granulocyte-colony stimulating factor (G-CSF), Granulocyte macrophage colony stimulating factor (GM-CSF), Macrophage colony stimulating factor (M-CSF), Erythropoietin, Thrombopoietin, Vitamin D3, Epidermal growth factor (EGF), Brain-derived neurotrophic factor, Leukemia inhibitory factor, thyroid hormone, Basic fibroblast growth factor (bFGF), aFGF, FGF-4, FGF-6, FGF-7/Keratinocyte growth factor (KGF), Platelet-derived growth factor (PDGF), Platelet-derived growth factor-BB, beta nerve growth factor, Activin A, Transforming growth factor beta 1 (TGF-β1), Interferon-α, Interferon-β, Interferon-γ, Tumor necrosis factor-α, Tumor necrosis factor-β, Burst promoting activity (BPA), Erythroid promoting activity (EPA), PGE2, insulin growth factor-1 (IGF-1), IGF-II, Neutrophin growth factor (NGF), Neutrophin-3, Neutrophin 4/5, Ciliary neurotrophic factor, Glial-derived nexin, dexamethasone, β-mercaptoethanol, retinoic acid, butylated hydroxyanisole, 5-azacytidine, amphotericin B, ascorbic acid, ascrorbate, isobutylxanthine, indomethacin, β-glycerolphosphate, nicotinamide, DMSO, thiazolidinediones, TWS119, oxytocin, vasopressin, melanocyte-stimulating hormone, corticortropin, lipotropin, thyrotropin, growth hormone, prolactin, luteinizing hormone, human chorionic gonadotropin, follicle stimulating hormone, corticotropin-releasing factor, gonadotropin-releasing factor, prolactin-releasing factor, prolactin-inhibiting factor, growth-hormone releasing factor, somatostatin, thyrotropin-releasing factor, calcitonin gene-related peptide, parathyroid hormone, glucagon-like peptide 1, glucose-dependent insulinotropic polypeptide, gastrin, secretin, cholecystokinin, motilin, vasoactive intestinal peptide, substance P, pancreatic polypeptide, peptide tyrosine, neuropeptide tyrosine, insulin, glucagon, placental lactogen, relaxin, angiotensin II, calctriol, atrial natriuretic peptide, and melatonin. thyroxine, triiodothyronine, calcitonin, estradiol, estrone, progesterone, testosterone, cortisol, corticosterone, aldosterone, epinephrine, norepinepherine, androstiene, calcitriol, and collagenβ.

In some embodiments of the screening methods described herein, the candidate differentiation factor is provided to the cell population in one or more concentrations. In some embodiments, the candidate differentiation factor is provided to the cell population so that the concentration of the candidate differentiation factor in the medium surrounding the cells ranges from about 0.1 ng/ml to about 10 mg/ml. In some embodiments, the concentration of the candidate differentiation factor in the medium surrounding the cells ranges from about 1 ng/ml to about 1 mg/ml. In other embodiments, the concentration of the candidate differentiation factor in the medium surrounding the cells ranges from about 10 ng/ml to about 100 µg/ml. In still other embodiments, the concentration of the candidate differentiation factor in the medium surrounding the cells ranges from about 100 ng/ml to about 10 µg/ml. In preferred embodiments, the concentration of the candidate differentiation factor in the medium surrounding the cells is about 5 ng/ml to 1000 µg/ml.

In some embodiments, steps of the screening methods described herein comprise determining expression of at least one marker at a first time point and a second time point. In some of these embodiments, the first time point can be prior to or at approximately the same time as providing the cell population with the candidate differentiation factor. Alternatively, in some embodiments, the first time point is subsequent to providing the cell population with the candidate differentiation factor. In some embodiments, expression of a plurality of markers is determined at a first time point.

The aforementioned methods are equally applicable to screening for small molecule and other compounds that improve viability, stabilize differentiation state, increase growth and maintain pluripotency of hES cells. It will be well within the level of skill in the art to adapt the teachings described herein to such screening methods.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor. In certain embodiments, marker expression is determined by Q-PCR. In other embodiments, marker expression is determined by immunocytochemistry.

In some embodiments of the screening methods described herein, sufficient time is allowed to pass between providing the cell population with the candidate differentiation factor and determining marker expression at the second time point. Sufficient time between providing the cell population with the candidate differentiation factor and determining expression of the marker at the second time point can be as little as from about 1 hour to as much as about 10 days. In some embodiments, the expression of at least one marker is determined multiple times subsequent to providing the cell population with the candidate differentiation factor. In some embodiments, sufficient time is at least about 1 hour, at least about 6 hours, at least about 12 hours to several days to weeks.

In some embodiments of the methods described herein, it is further determined whether the expression of the marker at the second time point has increased or decreased as compared to the expression of this marker at the first time point. An increase or decrease in the expression of the at least one marker indicates that the candidate differentiation factor is capable of promoting the differentiation of the endocrine precursor cells. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

Throughout this application, various publications are referenced. The disclosures of all of these publications and those references cited within those publications in their entireties are hereby incorporated by reference into this application in their entirety in order to more fully describe the state of the art to which this invention pertains.

EXAMPLES

The simple defined media employed in the below Examples is termed DC-HAIF, consisting essential of DMEM/F12, non-essential amino acids, trace elements, ascorbic acid, β-mercaptoethanol, Penicillin/Streptomycin (optional), with the only proteins being caprylic acid extracted fatty acid-free BSA, transferrin, and recombinant Heregulin-1β (H), Activin A (A), LR3-IGF1 (I), and FGF2 (F). DC-HAIF supported long term maintenance of pluripotent hES cells, as well as single cell passaging and scaled expansion of hES cell using Accutase™. See Robins, A. & Schulz, T. "Media and Extra Cellular Matrix Requirement for Large-Scale ESC Growth" in *Emerging Technology Platforms for Stem Cells* (Lakshmipathy, et al., eds, John Wiley & Sons, Inc.) pp. 251-74, 2009. A batch-tested commercial formulation of DC-HAIF is available from Life Technologies, under the trade name StemPro® hESC SFM.

Throughout these background studies it became clear that FGF2 was not a required component of the defined medium. Only poor or moderate phosphorylation of FGF receptors was observed after growth factor stimulation, even at high concentrations, and FGF2 could be omitted from the defined medium without any measurable impact on the culture, in terms of proliferation, spontaneous differentiation or maintenance of pluripotency. See Robins, A. & Schulz, T. 2009, supra. Therefore, certain studies below were conducted in the absence of added FGF2, and as indicated in the text and figure legends. Furthermore, because some assays required varying combinations of growth factors, a growth factor-free batch of StemPro® hESC SFM was custom ordered & purchased from Life Technologies to provide such flexibility.

In order to highlight additional signaling pathways with critical functions in hES cell culture, a LOPAC library consisting essentially of a library of small molecule compounds with known bioactivities was employed to screen against low density hES cell cultures. The aim was to identify those small molecules that negatively impacted culture expansion and/or pluripotency. Inhibition of key pathways would be expected to result in slowed proliferation, cytotoxicity, apoptosis or differentiation. Importantly, these primary and secondary screens were performed in the background of the simple defined medium described above and herein, reducing variability typically introduced by undefined components such as serum or semi-fractionated albumin. To determine activity, alkaline phosphatase staining assay was performed and about 50 small molecule compounds demonstrated some measurable amount of activity with regard to their impact on hES cell including hES cell growth and survival. Of these compounds, numerous inhibitors of cell surface neurotransmitter receptors were identified, suggesting at least a signaling role for these receptors in self-renewal. Using naturally occurring ligands or pharmacologically related derivatives, several classes of small molecule neurotransmitters, which may also act as hormones, were identified and demonstrated support and/or expansion of hES cell growth and survival at low density. Such activities could be crucial for developing advanced technologies for commercial and clinical application of hES cells, such as reliable single cell cloning, efficient derivation of new hES cell lines in fully defined and GMP-compliant conditions, growth of hES cells in suspension and enhanced viability upon passaging.

It should also be understood that the foregoing relates to exemplary embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents expressions, which, after reading the description herein, may suggest themselves to those skilled in the art without departing from the spirit of the present invention and/or the scope of the appended claims.

Example 1

Identification of Critical Pathways in Pluriotent Stem Cells

During the development of the defined media DC-HAIF (sold as StemPro® hESC SFM, Life Technologies), it was demonstrated that cultures of hES cells in this defined medium and single cell passaging with Accutase™ enabled robust plating and growth in small scale culture formats. Applying this approach in 96- and 384-well plates, quantitative and statistically significant cell-counting data was generated confirming the effect of AG825, an inhibitor of ERBB2 signaling, on self-renewal. About $3 \times 10^4$ hES cells per well were plated on MATRIGEL™ in StemPro® hESC SFM in 96-well plates and cultured for about 24 hours. The media was then changed, with new media containing 10 μM of a compound from the LOPAC1280 library (partial list in Table 1), and the cultures incubated for an additional 48 hours. The cultures were then fixed and stained for endogenous alkaline phosphatase, a marker of undifferentiated hES cells, activity. The format of this assay showed a clear distinction between the affected (non-confluent growth) and unaffected wells (confluent growth).

The LOPAC1280 collection (Sigma Cat# L01280), a library of small organic molecules with well-characterized pharmacological activities, was screened using the above described alkaline phosphatase detection assay in 96-well plates (16 plates total). Each 96-well assay was performed with 80 compounds (1 compound per well) and 16 wells as DMSO carrier negative controls. Greater than about 50 compounds were identified in the primary screen as impacting hES cell growth & expansion, which was then further determined to be a group of 38 molecules (Table 1) after secondary screening, and when known generally cytotoxic molecules were excluded (for example, 5-Azacytidine).

Pathways that are likely to be impacted by these molecules, and therefore possibly important in hES cells, included those involving signalling by NFκB, eNOS, RAR(a), calcium channels, tachykinin signaling, guanylyl cyclase, Src and Jak2.

Secondary screening was performed using the same assay, but with a dilution series of 0.1-50 μM of a compound as compared to the 10 μM initially used. The minimal effective concentration for each compound is indicated (Table 1). Interestingly, 11 of the 38 candidate compounds (28%) were known agonists, antagonists, modulators or ligands of neurotransmitter receptors (Table 1, FIG. 1). While a role for GABA signaling in hES cell self-renewal has been highlighted previously (Ludwig et al., 2006), it has not been examined under other defined media conditions. Potential roles for other neurotransmitters in undifferentiated pluripotent stem cells have not been characterized.

TABLE 1

Compounds Negatively Impacting hES Cell Cultures

| Name | Action | Selectivity | Description | *[Concentration]* μM |
|---|---|---|---|---|
| Lercanidipine hydrochloride hemihydrate | Antagonist | Cav1.2b | L-type (Cav1.2b) vascular calcium channel antagonist | 10 |
| Brefeldin A from *Penicillium brefeldianum* | Inhibitor | Golgi apparatus | Fungal metabolite that disrupts the structure and function of the Golgi apparatus | <0.1 |
| Caffeic acid phenethyl ester | Inhibitor | NFkB | NFkB inhibitor | <0.1 |
| Calmidazolium chloride | Inhibitor | $Ca^{2+}$ATPase | Potent inhibitor of calmodulin activation of phosphodiesterase; strongly inhibits calmodulin-dependent $Ca^{2+}$-ATPase | 5 |
| 7-Chloro-4-hydroxy-2-phenyl-1,8-naphthyridine | Antagonist | A1 | A1 adenosine receptor antagonist | 5 |
| Calcimycin |  | $Ca^{2+}$ | $Ca^{2+}$ ionophore used to potentiate responses to NMDA, but not quisqualate glutamate receptors | 1 |
| Dequalinium chloride hydrate | Blocker |  | Selective blocker of apamin-sensitive $K^+$ channels | 5 |
| Dihydroouabain | Inhibitor | $Na^+/K^+$ Pump | Sodium-potassium pump inhibitor | 1 |
| Diphenyleneiodonium chloride | Inhibitor | eNOS | Endothelial nitric oxide synthase inhibitor | 0.1 |
| Capsazepine | Agonist |  | Synthetic analog of capsaicin that acts as a specific vanilloid receptor antagonist | 5 |
| Domperidone | Antagonist | D2 | Peripheral dopamine receptor antagonist that does not cross the blood-brain barrier; anti-emetic | 25 |
| AC-93253 iodide | Agonist | RAR(α) | Potent, cell permeable, subtype selective retinoic acid receptor (RARalpha) agonist. | 5 |
| Retinoic acid p-hydroxyanilide | Inhibitor |  | Vitamin A acid analog with antiproliferative activity in cultured human breast cancer cells | 1 |
| NNC 55-0396 | Inhibitor | T-type | Selective T-type calcium channel inhibitor. | 25 |
| IB-MECA | Agonist | A3 | Selective A3 adenosine receptor agonist | 50 |

TABLE 1-continued

Compounds Negatively Impacting hES Cell Cultures

| Name | Action | Selectivity | Description | *[Concentration]* μM |
|---|---|---|---|---|
| Ivermectin | Modulator | alpha7 nACh | Positive allosteric modulator of alpha7 neuronal nicotinic acetylcholine receptor; also modulates glutamate-GABA-activated chloride channels | 5 |
| beta-Lapachone | Activator | | Induces apoptosis in HL-60 cells; anticancer agent | 5 |
| 2-methoxyestradiol | Metabolite | Estrogen | Inhibitor of angiogenesis and endothelial cell proliferation | 10 |
| Mibefradil dihydrochloride | Blocker | T-type | T-type $Ca^{2+}$ channel blocker | 25 |
| L-703,606 oxalate | Antagonist | NK1 | Potent and selective non-peptide NK1 tachykinin receptor antagonist | 25 |
| MG 624 | Antagonist | Nicotinic | Nicotinic acetylcholine receptor antagonist; selectively inhibits alpha-bungarotoxin sensitive receptors that contain the alpha7 subunit | 0.1 |
| Nordihydroguaiaretic acid from *Larrea divaricata* (creosote bush) | Inhibitor | Lipoxygenase | Lipoxygenase inhibitor | 5 |
| Pentamidine isethionate | Antagonist | NMDA | NMDA glutamate receptor antagonist; neuroprotective agent | 1 |
| Podophyllotoxin | Inhibitor | | Antineoplastic glucoside; inhibitor of microtubule assembly | <0.1 |
| Ouabain | Inhibitor | $Na^+/K^+$ ATPase | Blocks movement of the H5 and H6 transmembrane domains of $Na^+$-$K^+$ ATPases | <0.1 |
| Quinacrine dihydrochloride | Inhibitor | MAO | Monoamine oxidase (MAO) inhibitor; antimalarial | 10 |
| Protoporphyrin IX disodium | Activator | Guanylyl cyclase | Activates soluble guanylyl cyclase | 10 |
| SU 6656 | Inhibitor | Src family kinase | Selective Src family kinase inhibitor. | 25 |
| Ammonium pyrrolidinedithiocarbamate | Modulator | NOS | Prevents induction of nitric oxide synthase (NOS) by inhibiting translation of NOS mRNA | 10 |
| N-Oleoyldopamine | Ligand | CB1 | Endogenous vanilloid; weak CB1 cannabinoid receptor ligand. | 5 |
| SKF 96365 | Inhibitor | | Selective inhibitor of receptor-mediated and voltage-gated Ca2+ entry | 25 |
| PAPP | Agonist | 5-HT1A | Selective 5-HT1A serotonin receptor agonist | 25 |
| Tyrphostin AG 490 | Inhibitor | JAK2 | Jak-2 protein tyrosine kinase (PTK) inhibitor | 25 |
| SB 224289 hydrochloride | Antagonist | 5-HT1B | Selective 5-HT1B serotonin receptor antagonist. | 25 |
| Terfenadine | Antagonist | H1 | Non-sedating H1 histamine receptor antagonist | 25 |

TABLE 1-continued

Compounds Negatively Impacting hES Cell Cultures

| Name | Action | Selectivity | Description | *[Concentration]* µM |
|---|---|---|---|---|
| Vinblastine sulfate salt | Inhibitor | Tubulin | Inhibitor of microtubule assembly | <0.1 |
| Thapsigargin | Releaser | | Potent, cell-permeable, IP3-independent intracellular calcium releaser | <0.1 |

*[Concentration] indicates minimal effective concentration observed within a range of 0.1-100 µM.

Example 2

Small Molecules that Support Pluripotent Cell Self-Renewal in Defined Medium at Low Cell Density Of the 11 candidate compounds in the primary LOPAC screen that are known to act via neurotransmitter receptors, 6 were antagonists (adenosine, dopamine, cholinergic, NMDA, serotonin and histamine receptors) and one a receptor modulator (cholinergic (nicotinic) receptor) (FIG. 1). Because blocking of these receptors appeared to inhibit proliferation or cause apoptosis, receptor signaling may be important for hES cell growth and survival. It therefore followed that ligand-driven receptor stimulation could effect self-renewal or other desirable activities in hES cells. A major limitation in current hES cell culture is the inability to culture cells robustly at low densities. Despite several reports of single cell cloning of hES cell, reliable conditions for low-density culture and cloning of individual hES cell in fully defined media have not been developed. See Amit et al., 2000 Dev Biol 227, 271-278; Pyle et al., 2006 Nat Biotechnol 24, 344-50; and Watanabe et al., 2007 Nat Biotechnol 25, 681-6. A small molecule that elicits such an activity would also be predicted to provide substantial improvements in high-density, scaled or suspension culture of hES cells, in supporting higher plating/survival, aggregation or anti-apoptotic activities. Neurotransmitter ligands corresponding to the receptors identified above, as well as a range of other neurotransmitter ligands were therefore tested for support of cell survival and proliferation when hES cell were cultured at low densities.

Colony Forming Assay

About $10^4$ hES cells/well were plated in 6-well trays in StemPro® hESC SFM, in the presence of different compounds and cultured for about 7 days. The cultures were then fixed, stained for alkaline phosphatase activity and colonies were counted (FIG. 2). Fewer than 50 colonies were observed in defined media, StemPro® hESC SFM, alone, after 7 days, demonstrating that hES cell did not survive and/or proliferate effectively under a critical density threshold in StemPro® hESC SFM. Previous experiments indicated that a minimum of ~$10^5$ cells are required for expansion and serial passaging in 6-well trays. The ROCK inhibitor, Y27632, was included as a control due to reported effects on hES cells grown at low density of MEFs (Watanabe et al., supra), but did not support colony survival/expansion in defined medium (0 colonies). The neurotransmitters histamine, nicotine, and NMDA also failed to support enhanced colony formation. However, adenosine, acetylcholine (ACh) and norepinephrine ((−)-Norepinephrine, or (±)-Norepinephrine (+)-bitartrate) all supported elevated colony formation (FIG. 2). All three molecules bind and activate cell surface receptors, suggesting newly recognized signaling pathways that are important for self-renewal or anti-apoptotic signals in hES cells. The (±)-Norepinephrine (+)-bitartrate salt was used for all subsequent experiments involving norepinephrine (NE) unless specifically described otherwise.

Figure 3:
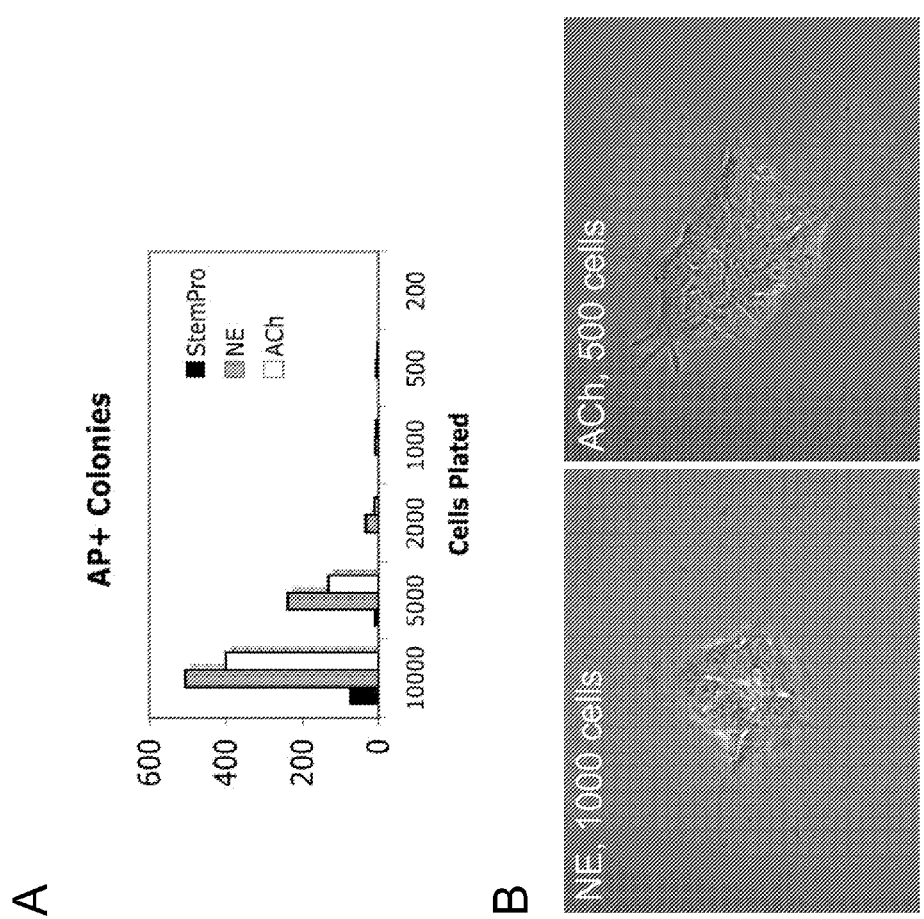
FIG. 3. Low density plating assay of hES cells. (A) 200-10000 cells/well were plated in 6-well trays in StemPro® hESC SFM medium, or StemPro® hESC SFM+50 µM NE, or +50 µM ACh, and stained with alkaline phosphatase (AP+) after 8 days. Comparative colony counts are shown. ACh (acetylcholine), NE ((±)-Norepinephrine (+)-bitartrate). (B) Undifferentiated morphology of hES cell colonies derived from plating at low cell densities and supported by NE or ACh (at day 5).

A similar colony counting experiment was performed using a range of cell densities (FIG. 3). More than four times as many colonies were detected in the presence of NE or ACh, compared to StemPro® hESC SFM medium alone, with colonies observed in wells with as few as 1000 and 500 plated cells, respectively. The frequency of colony formation was relatively consistent with different starting densities, on the order of 2.5-3.5% of the plated cells. At higher cell densities, cell migration leads to the formation of microcolonies over the first ~24 hours of culture. See Robins and Schulz 2009, supra. The consistent rate of colony formation observed in these low-density assays suggests that many colonies could be derived from single cells rather than migration and clustering. Imaging of colonies derived at low cell density indicated that they could exhibit tight, prototypical, hES cell morphology (FIG. 3). However, a low frequency of colonies exhibited a looser, more stellate arrangement of cells, which could indicate partial differentiation or poor cell-cell contact within colonies (not shown).

Real-Time Cell Index Monitoring

To examine more closely the potency of individual neurotransmitters and determine if synergies exist between different factors, low-density assays were performed in real time using an impedance reader. The ACEA biosciences RT-CES system uses 96-well trays that contain embedded microsensors to monitor changes in electrical impedance, which is translated into a measure of cell index. Any overt alteration within a cell culture can be detected, including but not limited to cell proliferation, migration, cell spreading, apoptosis, differentiation and the like. Previous experiments have indicated that hES cells attach and expand effectively in RT-CES trays, with a progressively increasing cell index signifying proliferation of undifferentiated cells (confirmed by Q-PCR). Once an undifferentiated culture becomes confluent the cell index remains high, but tends to go down and up (scallop) between daily feedings. Conversely, differentiation is typically indicated by the appearance of distinctive patterns, such as peaks and troughs in the cell index, likely indicative of an epithelial-to-mesenchymal transition, flattening, cell migration, apoptosis or similar differentiation and growth related changes.

Titration of Effective Neurotransmitter Concentrations

Figure 4:
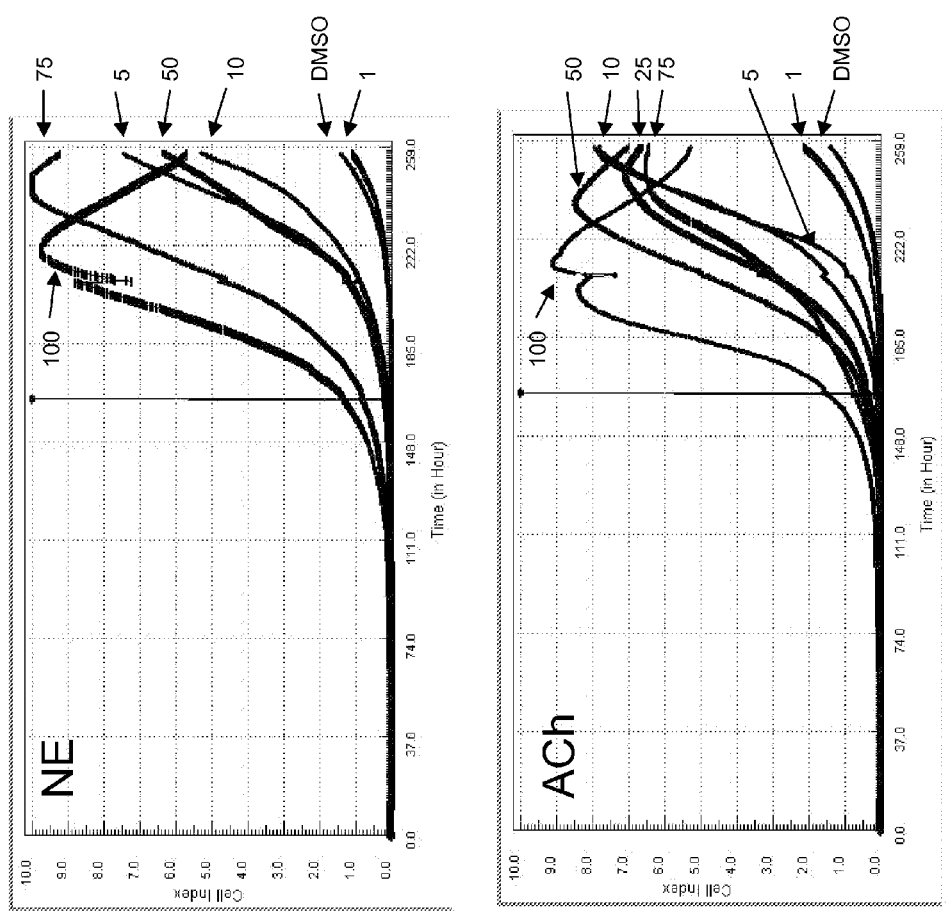
FIG. 4. Titration of NE and ACh using the RT-CES impedance reader. 1000 hES cells cells/well were plated in StemPro® hESC SFM containing the indicated concentrations of small molecules (in µM). In such an assay, the timing of when the cell index rises is associated with the proportion of cells that survive and expand at low density. Increasing concentrations of NE and ACh generally caused earlier rises in cell index. The spike in impedance at hr ~160 is an artifact and an error.

The RT-CES system was used to examine the concentration range at which NE and ACh were effective. Human ES cells were plated at low density, 1000 cells/well, in RT-CES trays and cultured for 10 days (FIG. 4). Cells were plated directly in StemPro® hESC SFM containing carrier control (DMSO), NE, or ACh. As expected, cells did not survive or proliferate effectively in DMSO alone, with a rise in cell index only observed after 9 days. 1 µM NE did not appear to affect low-density survival/proliferation, but increases in cell index were first detected with 5, 10 and 50 µM NE after ~6.5 days. Both 70 µM and 100 µM NE exhibited progressively earlier rises in cell index, and were apparently confluent after ~9 and ~10 days respectively. The titration of ACh resulted in a similar pattern, with 5 µM also being the lowest concentration that elicited an effect. These data suggested an increasing dose response for both NE and ACh, consistent with a receptor-mediated mechanism. Both NE and ACh were subsequently used at 50 µM, which represented an intermediate concentration for each neurotransmitter.

Neurotransmitter Combinations

Figure 5:
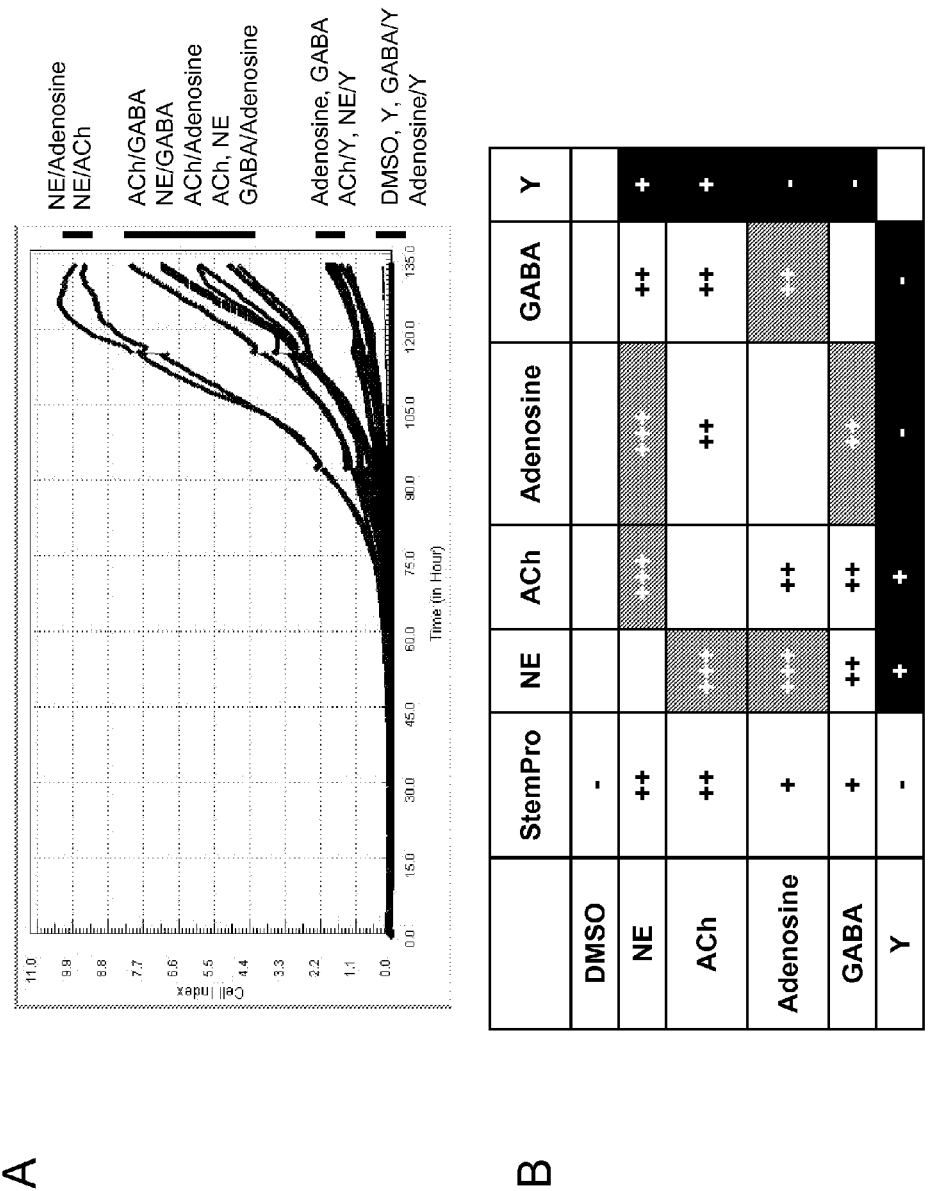
FIG. 5. Combined effects of small molecules compound combinations in low cell density assays. (A) 1000 hES cells/well were plated in StemPro® hESC SFM containing small molecules at 50 µM (NE, ACh, Adenosine, GABA) or 10 µM (Y27632). The assay was carried out over 5 days using the RT-CES system. Four groups of traces were observed: the most effective compound/combinations were NE/adenosine, and NE/ACh; an intermediate group contained NE and ACh as individual factors, and some other combinations; a low level group contained Adenosine and GABA alone, and several factors/combinations that were not effective. (B) Summary of the activities observed. Relative grading (− to +++) indicates effectiveness at supporting low-density growth, synergies are indicated by grey fill, and antagonism is indicated by black fill.

To examine potential additive effects of small molecule neurotransmitters, hES cells were plated in StemPro® hESC SFM containing carrier control (DMSO) or NE, ACh, adenosine, GABA, Y27632, or each combination of two of these factors (FIG. 5). Cells did not survive or proliferate in DMSO alone, nor in the presence of Y27632. Three patterns of cell expansion were detected. Addition of 50 µM NE or ACh as single factors enabled effective survival and expansion, with the cell index rising above background after about 3 days. Expansion within a second group, containing 50 µM adenosine or GABA was less effective, but detectable at ~4.5 days after plating. The group exhibiting the most pronounced expansion, also detectable after 3 days, consisted of cultures containing NE+Adenosine, and NE+ACh, suggesting synergy between these hormones/neurotransmitters. The only other combination that suggested synergy was GABA+adenosine, which was found in the middle group. Interestingly, the presence of Y27632 reduced the effects of NE, ACh, Adenosine and GABA, clearly demonstrating undesirable effects of inhibiting the ROCK pathway in the context of StemPro® hESC SFM media and these neurotransmitters. A summary chart of the interactions between these factors is presented in FIG. 5.

Example 3

Agonists that Support Low-Density Survival/Expansion of Pluripotent Stem Cells

Because a total of six different classes of neurotransmitter receptors were implicated in the original LOPAC screen, the next aim was to examine a wide array of similar ligands to determine the breadth of impact on low-density survival and/or expansion of hES cells. A sub-library of 88 neurotransmitter agonists was generated from the LOPAC collection, representing agonists of adenosine, adrenergic, benzodiazepine, cannabinoid and cholinergic receptors. Human ES cells were plated at 1000 cells/well directly into StemPro® hESC SFM containing DMSO or individual agonists (10 µM) and cultured for about 9 days in the RT-CES system. Additional agonists were identified that mimicked the effects of (±)-Norepinephrine (+)-bitartrate (FIG. 6A), which were agonists of adenosine and adrenergic receptors (FIG. 6B). Several additional neurotransmitters were also tested in a low-density impedance assay, including dopamine, serotonin and homovanillic acid (HVA), a catecholamine metabolite. These compounds also showed enhanced survival/proliferation compared to DMSO controls (FIG. 6C). These studies confirmed that a range of neurotransmitter receptors or signaling pathways could support low-density plating and expansion, and that each pathway was likely to be able to be activated by multiple ligands or agonists. Importantly, not all neurotransmitter pathways were likely to be involved in hES cell growth and pluripotency, as evidenced by the lack of robust activity shown by NMDA, histamine and GABA, and the 83 compounds in the agonist sub-library that were not effective at the 10 µM concentration tested.

Example 4

Effects of Neurotransmitter and Growth Factor Combinations in Defined Medium with Low-Density Pluripotent Stem Cell Cultures The above studies suggested that the signaling provided by the identified neurotransmitters could potentially complement or replace some of the growth factor proteins contained in DC-HAIF or StemPro® hESC SFM, thus making such media more cost-effective by substituting inexpensive small molecules for expensive recombinant proteins. In particular, about half of the cost of the defined medium is due to activin, which is difficult to produce and is manufactured using CHO cells. Yet, at least at low-density RT-CES assays indicated that the candidate neurotransmitters were not likely to be able to substitute entirely for the growth factors provided in StemPro® hESC SFM. However, for normal (high) cell densities these small molecules are potentially suitable substitutes.

Figure 7:
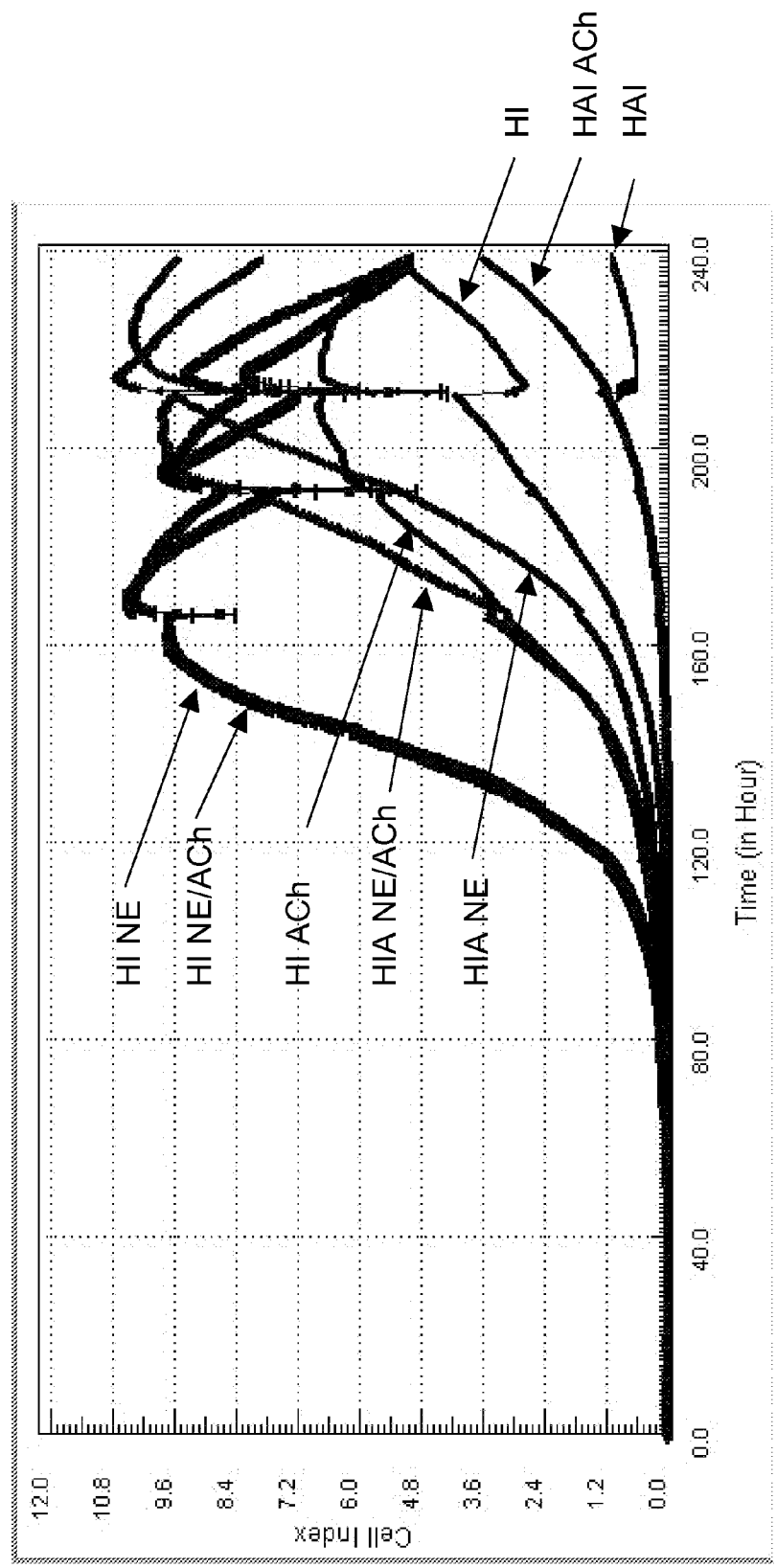
FIG. 7. Improved low cell density survival in the absence of activin. 1000 hES cells/well were plated in StemPro® hESC SFM containing the indicated combinations of growth factors and small molecules. Heregulin (H), LR3-IGF1 (I), Activin (A).

Additional assays were therefore performed to examine the effects of using simplified combinations of heregulin (H), LR3-IGF1 (I) and activin (A), with or without neurotransmitters (FIG. 7). In wells containing only StemPro® hESC SFM and HAI (heregulin, activin and LR3-IGF1), cells were not detected above background until ~day 9 as expected. However, StemPro® hESC SFM HI (heregulin and LR3-IGF1) unexpectedly supported much more robust survival/expansion, with growth being first detected at ~day 5.5. Activin had originally been included in DC-HAIF medium because it appeared to suppress spontaneous differentiation in hES cell cultures, presumably by competing with undesirable BMP-driven differentiation signals, and because inhibition of activin receptors caused increased differentiation. While the role of activin had not been previously tested at low cell density, these and subsequent experiments demonstrated that it played a major negative role in plating, survival and/or expansion of cells under these conditions. The addition of NE, ACh or NE/ACh supported substantially improved survival/expansion in either the HAI (heregulin, activin & IFG1) or HI (heregulin & IGF1) background. Interestingly, while the synergy between NE and ACh was observed in the background of HAI (as observed previously), it was not evident when activin was omitted. Therefore maximal survival/expansion was observed in StemPro® hESC SFM HI (heregulin & IGF1) with NE, to which the addition of ACh did not provide further improvement.

Colony Counting Assay

Figure 8:
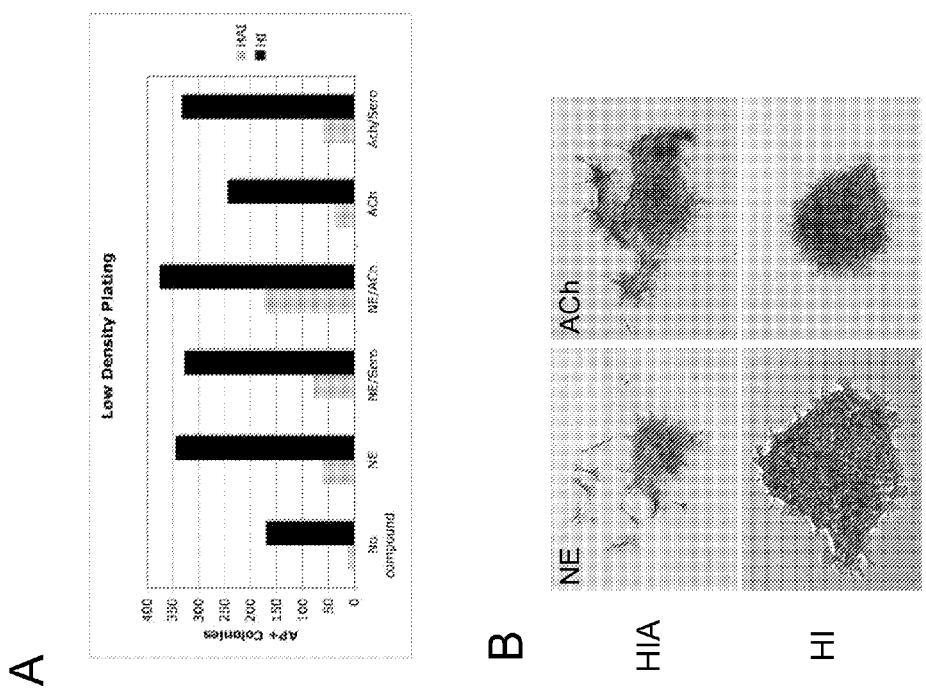
FIG. 8. Colony counting assay of the effect of activin on low-density survival/colony formation. (A) 10000 hES cells were plated in StemPro® hESC SFM containing the indicated combinations of growth factors and small molecules, and stained for alkaline phosphatase activity after 7 days. AP+ colonies were counted, clearly demonstrating the negative effects that activin has on low-density culture. (B) Photomicrographs of +NE and +ACh conditions in each growth factor background. In the absence of activin the colonies were much tighter and prototypical of undifferentiated cells.

In order to qualify these observations using a different approach, a low-density colony counting assay was performed (FIG. 8). About $10^4$ hES cell were plated in 6-well trays in StemPro® hESC SFM with HAI (heregulin, activin & IFG1) or HI (heregulin & IGF1), alone or in combination with neurotransmitter candidates and combinations from previous experiments (NE, NE/serotonin, NE/ACh, ACh, or ACh/serotonin). Counting of $AP^+$ colonies clearly confirmed the negative impact that activin had on colony formation at low cell density, with >200 colonies observed in the HI no neurotransmitter control (FIG. 8A). These colonies were small and had not proliferated extensively, but were clearly present compared to the negative control. Addition of any of the neurotransmitter ligands caused a marked improvement in colony formation, and consistent with the RT-CES assays, HI conditions with NE were not improved by addition of the other factors tested. Imaging of stained colonies revealed that in the presence of activin, surviving colonies were primarily non-uniform, with dispersed cells observed around small colony cores, and in general, exhibited a more stellate morphology (FIG. 8B). These features suggest that at low cell density activin may induce partial differentiation of the culture, or increased migration of cells such that compact colonies are not formed. It is highly likely that these or other effects impact cell survival. Conversely, in the absence of activin and presence of neurotransmitters, tight compact colonies were typically formed, which are prototypical of undifferentiated hES cells that can be expanded stably.

Figure 9:
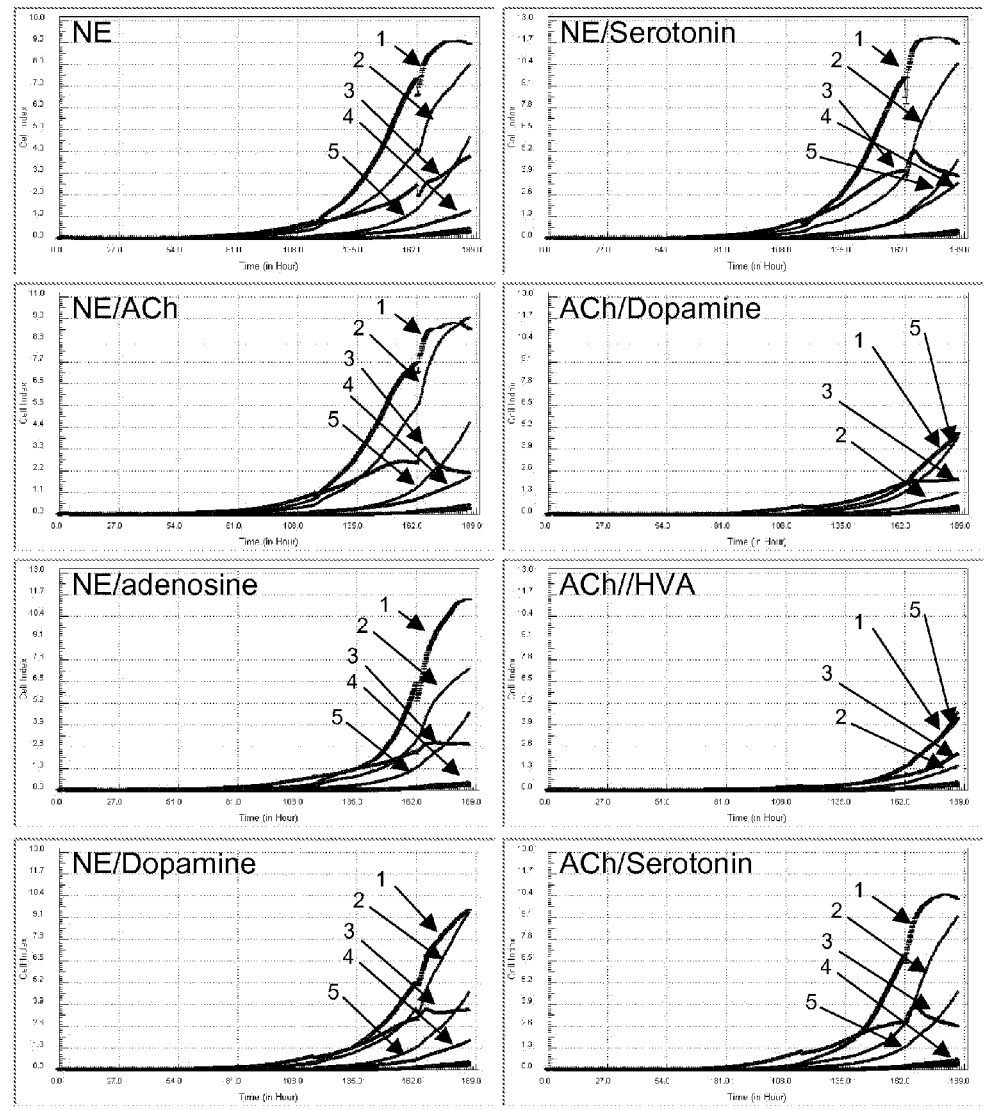
FIG. 9. Low-density RT-CES assays of combinations of growth factors and neurotransmitters. 1000 hES cells/well were plated in StemPro® hESC SFM containing the indicated combinations of growth factors and small molecules. Heregulin (H), LR3-IGF1 (I), Activin (A). Small molecules were tested at 50 µM.

Similar experiments were performed to determine if the signaling provided by neurotransmitters could substitute for IGF1 or Heregulin. Low-density plating assays were performed in the RT-CES reader using StemPro® hESC SFM with different combinations of activin (A), heregulin (H), LR3-IGF1 (I), and candidate neurotransmitters (FIG. 9). Consistent with previous assays, rises in impedance were detected much earlier in the absence of activin, and in the presence of neurotransmitters NE, NE/ACh, NE/adenosine, NE/dopamine, NE/serotonin and ACh/Serotonin The combinations of ACh/Dopamine, or ACh/HVA did not appear to promote substantial survival/expansion of hES cell. While medium containing heregulin alone did not support low cell density survival, addition of the same neurotransmitters as above caused a marked improvement. However, in the absence of heregulin (IGF alone), cultures did not expand in either the presence or absence of neurotransmitters. Therefore, while Activin and IGF1 appeared to be dispensable in these short-term assays, the activities provided by neurotransmitters did not appear to substitute for heregulin signaling at low cell densities.

Example 5

Neurotransmitters Enhance Suspension Culture of Pluripotent Cells

Small molecule ligands that support survival or self-renewal at low cell densities could also be expected to have beneficial effects in other culture formats. Applicants have previously developed a suspension culture system for hES cells that enables serial propagation of cells and effective expansion of cultures. Human ES cells, at least BG02 and CyT49 cells, have been maintained in suspension for greater than 10 passages without differentiation. The basis of the technique is to dissociate cultures to single cells with reagents that preserve high viability, such as Accutase™, TrypLE or cell dispersal buffer, then aggregate defined concentrations of cells in defined medium in rotational culture. These methods are described in more detail in International Application PCT/US2008/082356, entitled STEM CELL AGGREGATE SUSPENSION COMPOSITIONS AND METHODS OF DIFFERENTIATION THEREOF, filed Nov. 4, 2008; and International Application PCT/US2007/062755, entitled COMPOSITIONS AND METHODS FOR CULTURING DIFFERENTIAL CELLS, filed Feb. 23, 2007, which are herein incorporated by reference in their entireties. Self-aggregation of hES cells occurs in the absence of added extracellular matrix (ECM) or ECM-like proteins and is presumed to be driven in part by homotypic interaction of E-cadherin. The aggregates that are formed expand over 3-4 days and are kept apart from each other by the shear forces generated by rotational culture. Cells are blocked from differentiating by the self-renewal signaling provided by the defined medium and retain their pluripotent characteristics: marker expression, normal karyotype, and differentiation potential in vitro and in teratomas. To maximize the expansion of cultures at each passage it is desirable to generate the largest number of uniform aggregates of the minimal viable size.

Figure 10:
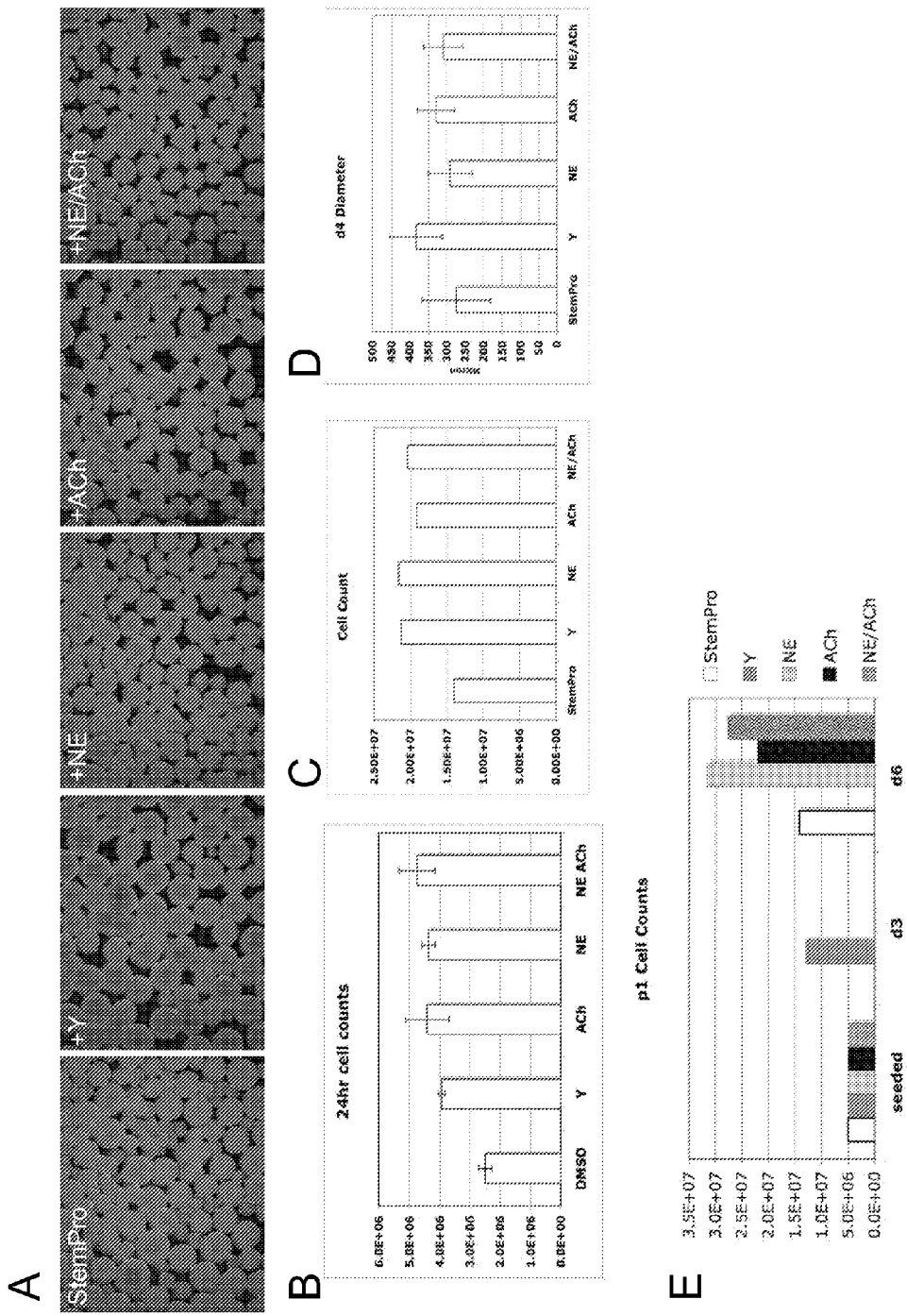
FIG. 10. Effects of NE and ACh in suspension culture of hES cell. (A) $5 \times 10^6$ CyT49 cells were seeded in 5 ml StemPro® hESC SFM containing heregulin, LR3-IGF1, Activin and the indicated neurotransmitters at 50 µM in low-attachment 6-well trays and placed at 100 rpm. Undifferentiated suspension aggregates were imaged on day 4. (B) 24 hours after seeding, two wells from each condition were harvested and counted to determine the number of viable cells. (C) Cell counts of each condition when the cultures were split on day 4. (D) The images in (A) were used to determine aggregate diameters using the ImagePro software measurement tool. Average diameters and standard deviations from 50-100 aggregates from each condition are shown. (E) Passage 1 cell counting data. $5 \times 10^6$ CyT49 hES cells from p0 cells in (A) were seeded into the same conditions. The aggregates in the condition containing Y27632 were larger and had to be passaged 3 days after seeding, before the centers of the largest aggregates became necrotic. Conversely, the other conditions could be cultured for 6 days before passaging, resulting in higher cell counts.

Human ES cells were aggregated in suspension in 5 ml StemPro® hESC SFM containing heregulin (H), IGF1 (I) and activin (A) in low attachment 6-well trays at $10^6$ cells/ml, and placed at 100 rpm. Experimental variables included the addition of either Y27632, NE, ACh or NE/ACh (FIG. 10A). All conditions aggregated successfully and duplicate wells were harvested after 24 hours, disaggregated and counted to determine short-term cell survival. Only about 50% of cells survived the first 24 hours in StemPro® hESC SFM alone, but all other treatments showed ~$4 \times 10^6$ or more cells (FIG. 10B). The positive effect of Y27632 upon cell survival at high cell density in StemPro® hESC SFM was consistent with previous observations in adherent culture, and was matched by similar effects with NE, ACh and NE/ACh. All conditions could be expanded over 4 days of rotational culture, and the increase in cell number elicited by treatment with small molecules was confirmed by cell counting (FIG. 10C). In addition, measurement of the diameters of aggregates on day 4 confirmed observations made during the culture period (FIG. 10D). In StemPro® hESC SFM alone, aggregate size was highly variable, whereas addition of Y27632 had caused enhanced aggregation of cells such that fewer numbers of larger aggregates were found. In contrast, the addition of NE, ACh or NE/ACh permitted smaller aggregates to form than those formed in Y27632, which were of a more consistent and uniform size than that in StemPro® hESC SFM alone. These data indicated that neurotransmitters offered several advantages for (normal) higher-density suspension culture of hES cells. Firstly, they promoted cell survival during the aggregation phase, equal to or better that that observed with Y27632. Secondly, they promoted smaller and more consistently uniformly sized aggregates to form, potentially providing much more control over aggregate size and lengthening of time between splitting, thereby maximizing the expansion possible at each passage.

Chromosome Stability

Figure 11:
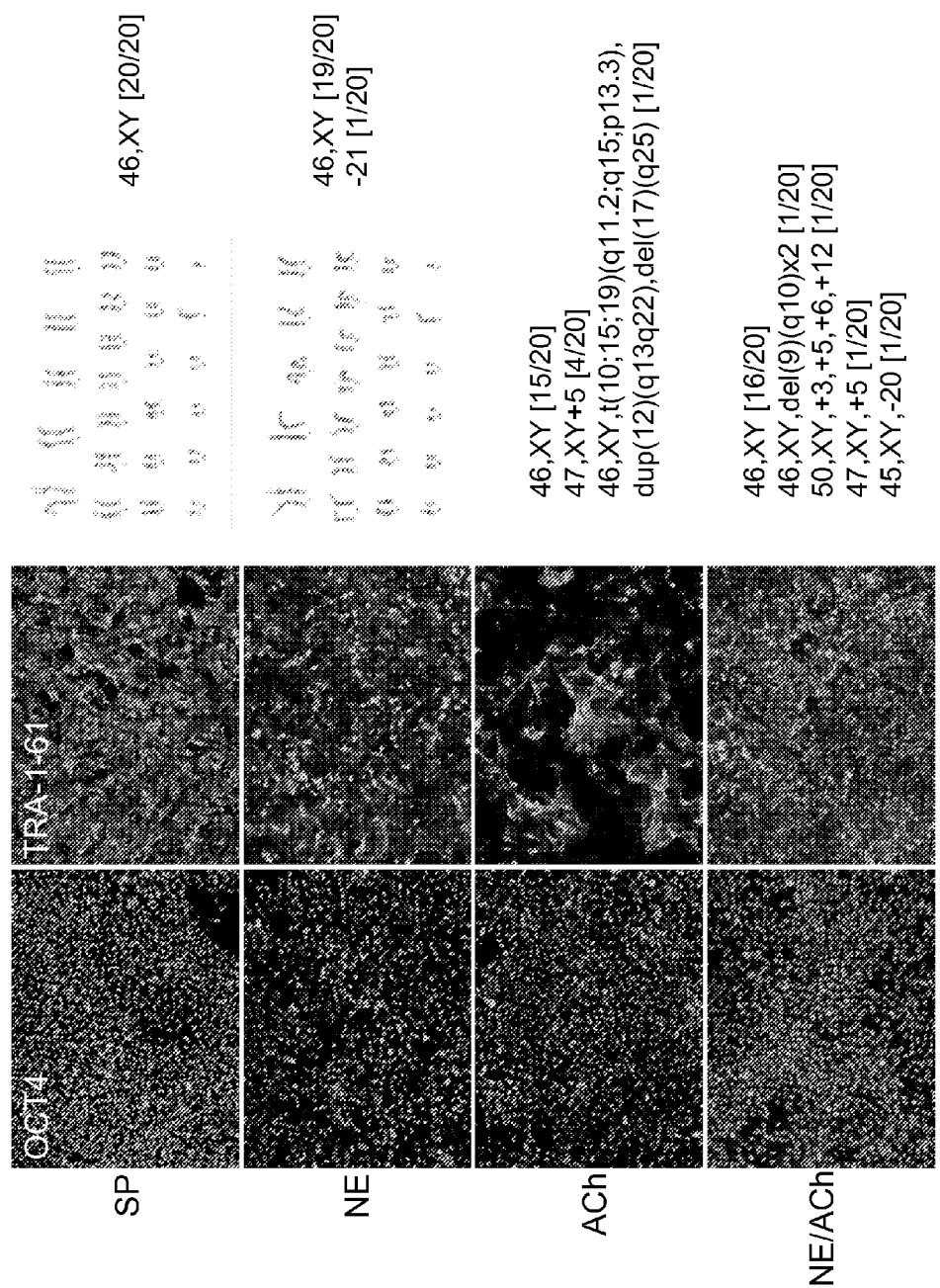
FIG. 11. Suspension hES cell cultured with NE, NE/ACh or NE/ACh remain undifferentiated. CyT49 cells were grown as suspension aggregates in the presence of NE, NE/ACh or NE/ACh for 16 passages without differentiating morphologically. After p10, some cells were re-plated to adherent culture and examined by karyotyping and immunofluorescent staining for OCT4 and Tra-1-61. All cultures remained undifferentiated and expressed these pluripotency markers uniformly. (SP) StemPro® SFM HIA, NE (+NE at 50 µM), ACh (+ACh at 50 µM), NE/ACh (+NE/ACh at 50 µM). Karyotype data is shown to the right. SP and SP+NE cultures were karyotypically normal. Cultures containing ACh were aneuploid.

To examine these possibilities, these cultures were serially passaged to p1 (FIG. 10E). Because Y27632 treated aggregates were of a larger size, they required passaging after only 3 days, and only generated about $1.2 \times 10^7$ cells during that period. In contrast, the cultures containing NE, ACh or NE/ACh were cultured for 6 days and generated greater than $2 \times 10^7$ cells per well. Suspension cultures containing NE, ACh or NE/ACh were maintained for 12 serial passages, in parallel with a HAIF control culture, and all conditions maintained an undifferentiated morphology throughout. Suspension aggregates were dissociated to single cells after 10 passages and replated to adherent culture for analyses. Expression of Oct4 and Tra-1-60 (FIG. 11) and other pluripotency markers was maintained uniformly, demonstrating that the cultures were undifferentiated. Replated cultures were also G-banded to determine their karyotype. Both the HAIF control and HAIF/NE cultures were euploid or normal, whereas the cultures containing ACh were aneuploid or abnormal, exhibiting trisomy of chromosome 5 and other alterations. This experiment suggested that genomic stability could be maintained during long-term culture of hES cell in the presence of NE, and that subpopulations of aneuploid cells with growth advantages were not generated or enriched. However, because this data suggests that ACh may affect genomic integrity, it is clear that not all factors that support low-density survival/growth of hES cell have utility at higher density cell growth conditions.

Example 6

Figure 12:
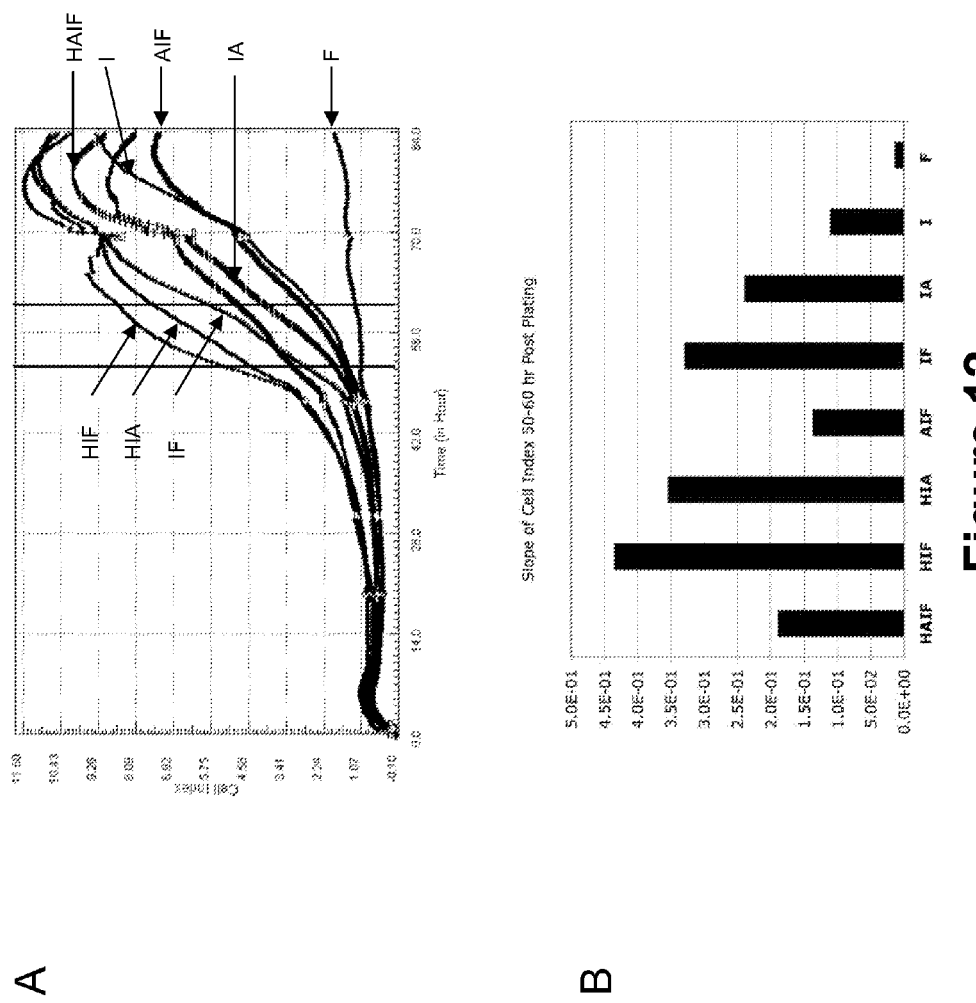
FIG. 12. NE and Growth factor combinations that support hES cells (e.g. BG02) in short term impedance assays at standard density. (A) $10^4$ BG02 cells/well were plated in StemPro® hESC SFM containing 50 µM NE and the indicated combinations of growth factors. Heregulin (H), LR3-IGF1 (I), Activin (A), FGF2 (F). As opposed to the outcome at low cell density, NE could support the expansion of cultures in the absence of heregulin in some conditions. Such supportive combinations included NE/AIF, NE/IF, NE/IA, and NE/I. (B) Measurement of the slope of the cell index from 50-60 hours (lines in A) post plating is shown. Compared to a condition showing only minimal proliferation (NE/F), other conditions exhibited effective increase in cell index, indicative of expansion of the population.

Growth Factor Combinations that Support Expansion of Pluripotent Cells at Standard Density in the Presence of Norepinephrine Norepinephrine did not appear to be able to substitute for heregulin signaling when cells were grown at low density, suggesting that these factors may impact different signaling pathways. However, the context of cell-cell contact and signaling is quite different at standard seeding densities, where cells migrate to form micro-colonies over the first 24 hours of culture. See Robins and Schulz, 2009, supra. Therefore, substantial differences in the growth factors required to support hES cell may be observed at low and high densities. Short-term growth assays at standard densities were therefore conducted with hES cells using the impedance reader. About $10^4$ hES cells/well were plated in StemPro® hESC SFM containing 50 µM NE and differing combinations of heregulin (H), LR3-IGF1 (I), Activin (A), or FGF2 (F) and monitored over 3.5 days. As opposed to the outcome at low cell density, NE could support the expansion of cultures in the absence of heregulin in certain higher density conditions (FIG. 12A). Supportive combinations included NE/AIF, NE/IF, NE/IA, and NE/I. Measurement of the slope of the cell index during log phase growth is shown (FIG. 12B). These data indicate that it is possible to expand undifferentiated hES cells in the presence of NE, with a simplified combination of recombinant growth factors. Such a simplified medium could have substantial advantages, particularly in relation to cost-of-goods during large-scale manufacturing of hES cells for therapeutic applications.

Example 7

Figure 13:
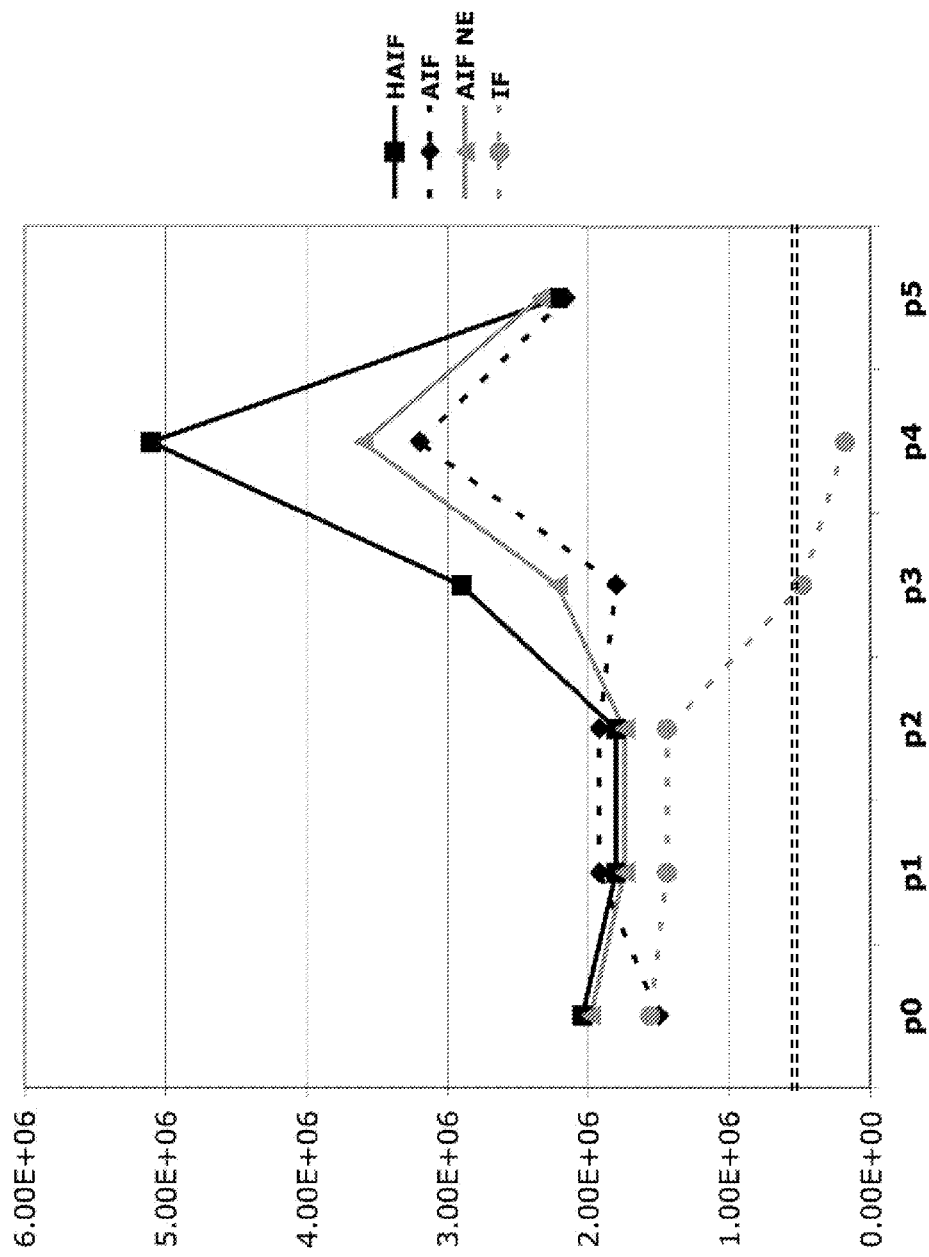
FIG. 13. Norepinephrine and growth factor combinations that support serial passaging of hES cells (e.g., BG01 cells) at standard density. Relative expansion of hES cells during serial culture. $5 \times 10^5$ hES cells were plated/well in 6-well trays at each passage in StemPro® hESC SFM containing combinations of 50 µM NE and the indicated growth factors. Heregulin (H), LR3-IGF1 (I), Activin (A), FGF2 (F). Cell counts at the end of each passage for conditions that supported expansion are plotted. The dashed double line represents the number of cells that were plated at each passage. Compared to the HAIF control culture, the absence of heregulin (AIF) led to reduced growth over multiple passages. Colony growth was observed in the densely packed outer ring of the wells, but not across the whole dish. A culture exposed to only IF could not be maintained effectively after 2 passages, confirming a requirement for activin/nodal signaling for this cell line. The presence of NE had a substantial positive impact on proliferation in AIF conditions, enabling even culture growth and a morphology similar to HAIF conditions. NE could not substitute for the activin/nodal requirement, as the IF/NE condition differentiated over several passages.
Figure 14:
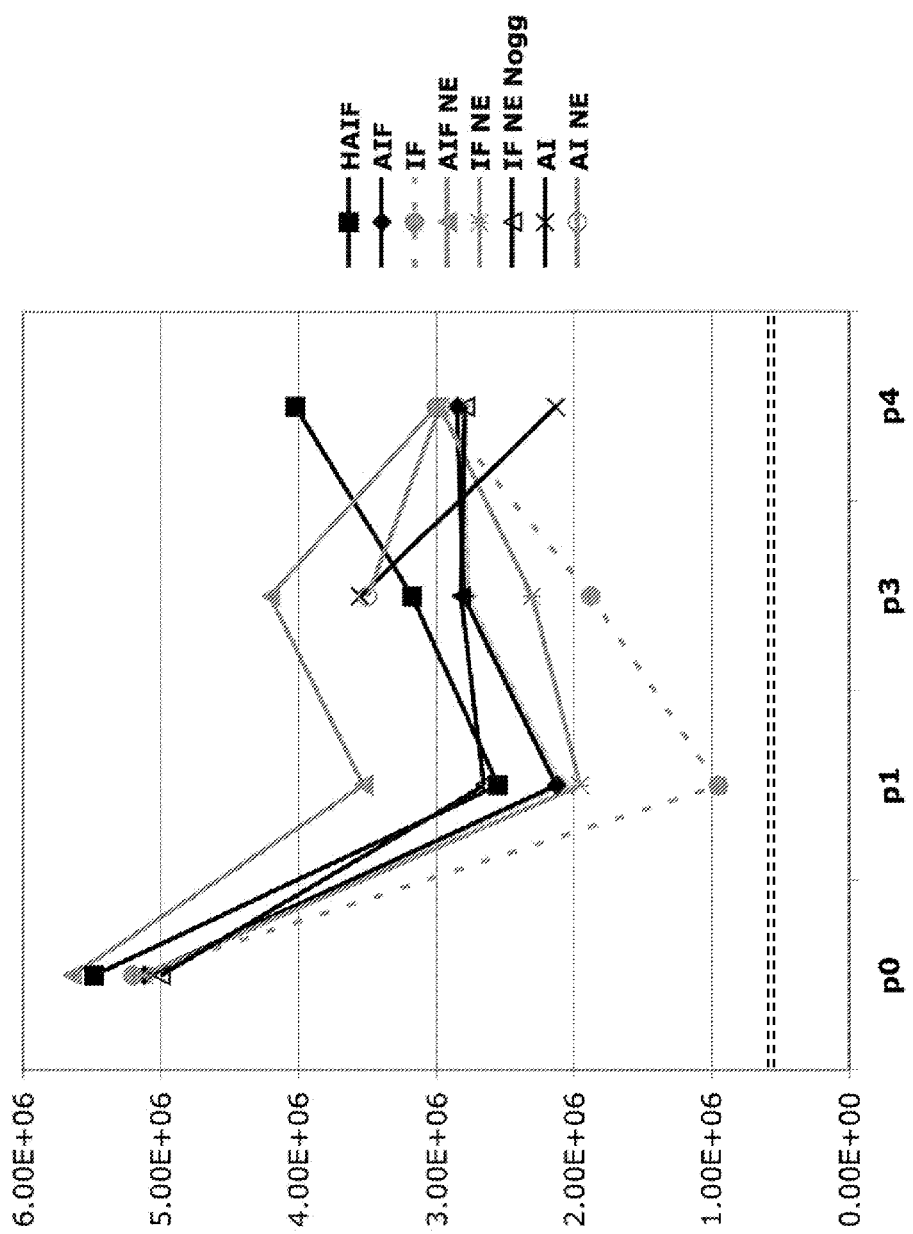
FIG. 14. Norepinephrine and growth factor combinations that support serial passaging of hES cells at standard density. Relative expansion of hES cells during serial culture. 5×105 hES cells were plated/well in 6-well trays at each passage in StemPro® hESC SFM containing combinations of 50 µM NE and the indicated growth factors. Cell counts at the end of each passage were plotted. The dashed double line represents the number of cells that were plated at each passage. Heregulin (H), LR3-IGF1 (I), Activin (A), FGF2 (F). At passage 2, the AIF culture was also used to set up extra wells of AI, or AI/NE. Compared to the HAIF control culture, the absence of heregulin (AIF) led to a morphological alteration. While the cells retained characteristics of undifferentiated cells, they were flatter and larger in appearance, with more gaps between cells. Similar morphology was observed in all cultures containing Activin (in the absence of heregulin). Colonies in IF packed very tightly and were domed, which was more similar to the morphology of standard mouse ES cells cultures. Cultures in IF/NE, and IF/NE/Noggin exhibited exceptional morphology, with tight epithelial colonies and no obvious differentiation.

Growth Factor Requirements for Serial Passaging of Pluripotent Cells in the Presence of Norepinephrine The effects of serial passaging of hES cells in NE-containing media and candidate simplified combinations of growth factors were tested with at least BG01 (FIG. 13) and BG02 (FIG. 14) cells. Test conditions were compared to cells maintained in StemPro® hESC SFM with 10 ng/ml heregulin (H), 200 ng/ml LR3-IGF1 (I), 10 ng/ml Activin (A), and 8 ng/ml FGF2 (F). Certain hES cell cultures could not be maintained effectively in the absence of heregulin (i.e. AIF), for example, cultures had generally poor proliferation, although in densely packed areas, such as that at the outer rim of wells, proliferation was normal. Cultures where activin was omitted (IF) also proliferated poorly, and were lost by the fourth passage. Yet, when NE was included, effective hES cell proliferation and even hES cell colony growth across the well was observed in the absence of heregulin (AIF NE). Still, NE does not appear to substitute for the requirement of Activin at standard cell density, as IF NE cultures differentiated over several passages. HAIF, AIF and AIF NE conditions have been maintained for at least 5 passages, with AIF NE favored over AIF alone because the latter continued to exhibit uneven growth.

Figure 15:
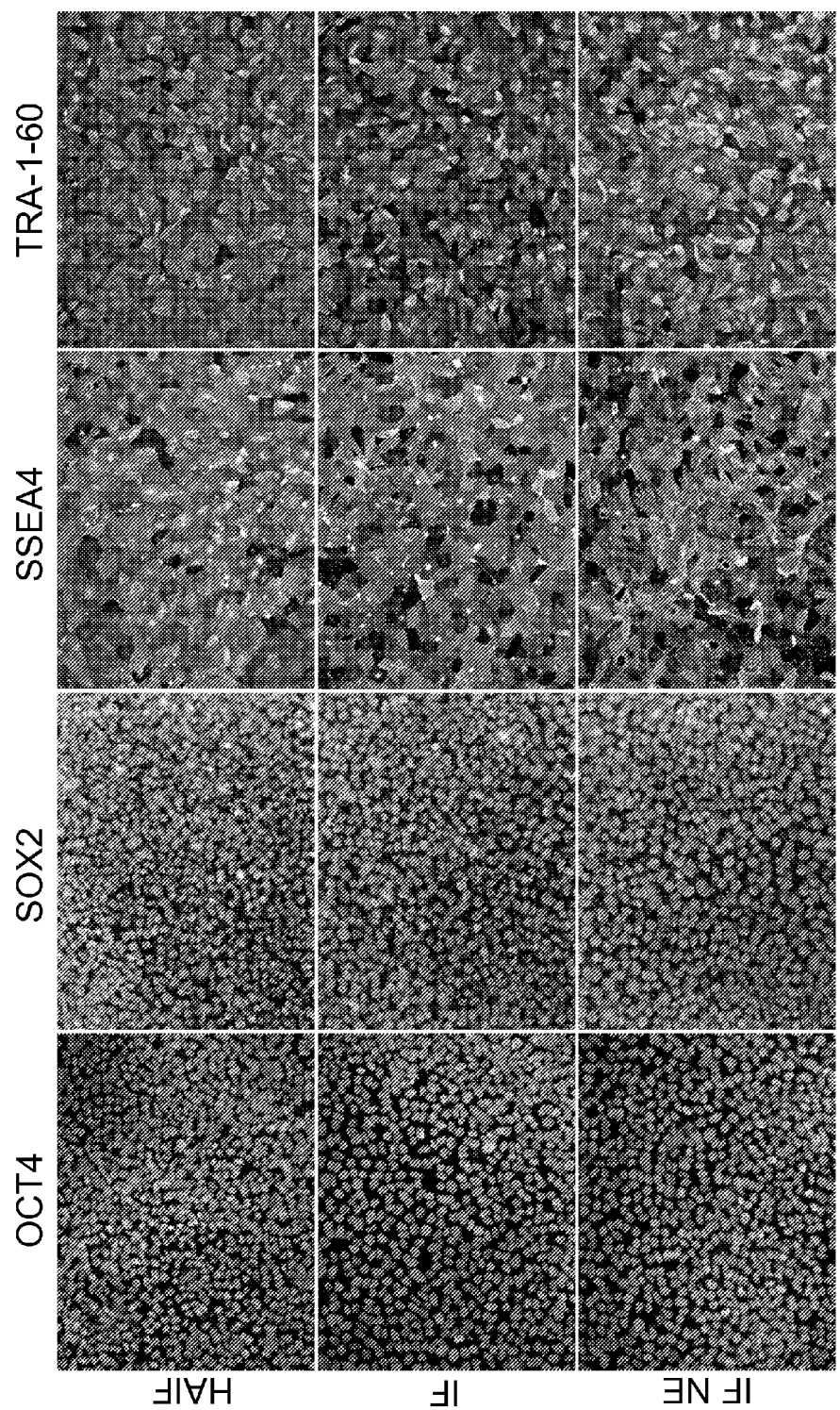
FIG. 15. Expression of pluripotency markers in hES cells serially passaged in defined media containing NE and simplified combinations of growth factors. Human ES cells cultured for four passages as described (FIG. 14) were plated onto slides, expanded and immuno-stained for the indicated markers. Cultures expanded in IF, and IF/NE (as well as AIF and AIF/NE, not shown), retained the expected profile of expression of markers of pluripotency, including OCT4, SOX2, SSEA4 and TRA-1-60.

Certain hES cells also exhibited a morphological response to the loss of heregulin (AIF), with the cells becoming flatter, more spread out and colonies not displaying tight epithelial packing. A similar morphology was observed in all cell cultures containing activin (in the absence of heregulin). These cell cultures otherwise continued to display undifferentiated characteristics and did not appear to be differentiating overtly. Colonies in the absence of both heregulin and activin (IF) were packed very tightly and domed, which was more similar to the morphology of typical mouse ES cell cultures. Cultures in IF/NE, and IF/NE/Noggin exhibited exceptional ES morphology, with tight epithelial colonies and no obvious differentiation. While multiple conditions could therefore support the continued expansion of hES cells over numerous passages, only IF NE and IF NE Noggin combinations promoted the maintenance of expected epithelial characteristics. The maintenance of pluripotency in these serially passaged hES cells was demonstrated by immunofluorescence for the markers Oct4, SSEA4, Tra-1-60 and Sox2 (FIG. 15). These experiments demonstrated and confirmed that a simplified combination of growth factors supports the serial propagation of pluripotent cells and especially when norepinephrine (NE) is included in the culture medium.

Example 8

Expression and Function of Adrenoceptors in Pluripotent Cells

Figure 16:
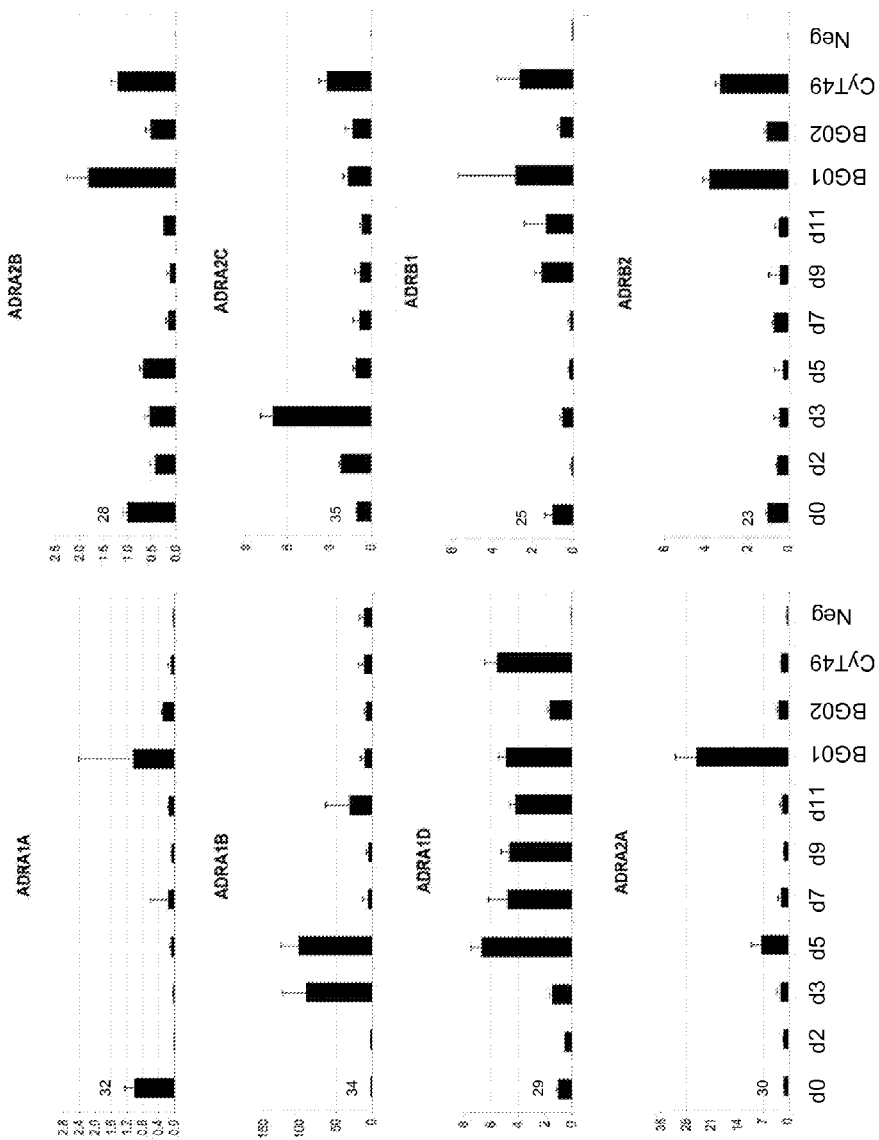
FIG. 16. qPCR analyses of adrenoceptor expression in hES cell and during differentiation to pancreatic endoderm. Gene names are used for identifiers (for example, ADRA1A indicates alpha1A-adrenoceptor). The hES cell samples for pancreatic differentiation are indicated by day of differentiation: d0, Undifferentiated hES cells; d2/3, Definitive Endoderm; d5/7, Primitive Gut Tube; d7/9 Posterior Foregut; d11, Pancreatic Endoderm. Charts are relative to fold-expression of the d0 hES cell sample, and the threshold crossing point for this sample is shown to suggest relative expression level between different adrenoceptors. Additional samples of hES cells including BG01, BG02 and CyT49 cells are shown. ADRB1, ADRB2, ADRA2B and ADRA1D appeared to be the most consistent and highest expressed adrenoceptors in undifferentiated hES cell. ADRA2C appeared to be expressed consistently in the hES cell samples, but at a lower level, while ADRA1A and ADRA1B were only at low levels, or were only detected inconsistently in undifferentiated cells.

To examine their potential role in pluripotent stem cell proliferation, expression of adrenoceptors was examined using Q-PCR and inhibitors of adrenoceptor function were tested for effects on cell growth. Uniform and relatively high expression of several adrenoceptors was detected in hES cell lines (FIG. 16), including ADRB1, ADRB2, ADRA2B and ADRA1D. ADRA2C appeared to be expressed consistently in the hES cell samples, but at a lower level, while ADRA1A and ADRA1B were only at low levels, or were only detected inconsistently in undifferentiated cells. Forty different inhibitors of adrenoceptors were then tested for effects upon hES cell expansion at low cell density in the presence of 50 µM NE. By comparison to the untreated HAIF+NE controls, seven α-adrenoceptor antagonists, 5β-adrenoceptor antagonists, and 2β-adrenoceptor blockers were identified that impacted hES cell survival and/or expansion at low cell density (FIG. 17). These studies indicated that hES cells expressed a range of both α- and β-adrenoceptors and that inhibiting receptor function impacted the expansion of hES cell, both of which confirm the importance of NE signaling in hES cell.

The methods, compositions, and devices described herein are presently representative of preferred embodiments and are exemplary and are not intended as limitations on the scope of the invention. For example, certain hES cell lines were employed, however the present invention contemplates use with any pluripotent stem cell lines including human iPS cell lines and other not mentioned hES and iPS cell lines such as those in Table 2 and 3 below, respectively (adapted from the National Institute of Health's Stem Cell Registry on the world wide web at stemcells(dot)nih.gov(forward slash) research(forward slash) registry, as well as the Human Embryonic Stem Cell Registry and the International Stem Cell Registry located at the University of Massachusetts Medical School, Worcester, Mass., USA. These databases are periodically updated as cell lines become available and registration obtained. Some of which cell lines are not available for shipment from the NSCB Stem Cell Registry. Regardless, at least the below hES cell lines can be made commercially available as of the date of this present invention.

TABLE 2

Human ES cell lines

| Institution (Country) | Name |
|---|---|
| U.S.A. | |
| BresaGen, Inc., Athens, Georgia (USA) | BG01, BG02, BG03; BG04; BG01v |
| Invitrogen (USA) | BG01v/hOG |
| CyThera, Inc., San Diego, California (USA) | CyT49, CyT203, CyT25 |
| Geron Corporation, Menlo Park, California (USA) | GE01, GE07, GE09, GE13, GE14, GE91, GE92 (H1, H7, H9, H13, H14, H9.1, H9.2) |
| University of California, San Francisco, California (USA) | UC01, UC06 (HSF-1, HSF-6); UCSFB1, UCSFB2, UCSFB3, UCSFB4, UCSFB5, UCSFB6, UCSFB7, UCSFB8, UCSFB9 & UCSFB10 |
| Wisconsin Alumni Research Foundation, Madison, Wisconsin (USA) | WA01, WA07, WA09, WA13, WA14 (H1, H7, H9, H13, H14) |
| Children's Hospital Corporation (USA) | CHB-1, CHB-2 CHB-3 CHB-4, CHB-5, CHB-6, CHB-8, CHB-9, CHB-10, CHB-11 & CHB-12 |
| The Rockefeller University (USA) | RUES1, RUES2 & RUES3 |
| Harvard University (USA) | HUES1, HUES2, HUES3, HUES4, HUES5, HUES6, HUES7, HUES8, HUES9, HUES10, HUES11, HUES12, HUES13, HUES14, HUES15, HUES16, HUES17, HUES18, HUES19, HUES20, HUES21, HUES22, HUES23, HUES24, HUES25, HUES26, HUES27; HUES28; HUES48; HUES49; HUES53; HUES55 & HUES 56 |
| Mt Sinai Hosp-Samuel Lunenfeld Research Institute (USA) | CA1 & CA2 |
| Children's Memorial Hospital (USA) | CM-1, CM-2, CM-5, CM-6, CM-7, CM-8, CM-11, CM-12, CM-13, CM-14, CM-16 |
| The University of Texas Health Science Center at Houston (USA) | CR1 & CR2 |
| California Stem Cell, Inc. (USA) | CSC14 |
| University of Connecticut School of Medicine/Dentistry (USA) | CSC14, CT1, CT2, CT3, & CT4 |
| The Third Affiliated Hospital of Guangzhou Medical College (USA) | FY-3PN; FY-hES-1; FY-hES-3; FY-hES-5; FY-hES-7 & FY-hES-8 |
| Advanced Cell Technology, Inc. (USA) | MA 01; MA 09; MA 42; MA 50; MA135; NED 1; NED 2; NED 3 & NED 4 |
| Stanford University (USA) | MFS5 |
| New York University School of Medicine (USA) | NYUES1; NYUES2; NYUES3; NYUES4; NYUES5; NYUES6 & NYUES7 |
| Reprogenetics, LLC (USA) | RNJ7 |
| University of California, Los Angeles (USA) | UCLA1; UCLA2 & UCLA3 |
| Eastern Virginia Medical School (USA) | ES-76; ES-78-1; ES-78-2 |
| Reproductive Genetics Institute (USA) | RG-222; RG-230; RG-249; RG-308; RG-313; RG-148; DYSTROPHIA MYOTONICA 1 (DM1), affected, 46, XY; RG-153; DYSTROPHIA MYOTONICA 1 (DM1), affected, 46, XX; RG-170; MUSCULAR DYSTROPHY, BECKER TYPE (BMD), affected, 46, XY; RG-186; HUNTINGTON DISEASE (HD), affected, 46, XX; RG-194; HUNTINGTON DISEASE (HD), affected, 46, XY; RG-233; HEMOGLOBIN BETA LOCUS (HBB), affected (HbS/HbS - sickle cell anemia), 46, XX; RG-245; EMERY-DREIFUSS MUSCULAR DYSTROPHY, X-LINKED (EDMD), carrier, 47, XXY; RG-246; EMERY-DREIFUSS MUSCULAR DYSTROPHY, X-LINKED (EDMD), affected, 46, XY; RG-271; TORSION DYSTONIA 1 (DYT1), AUTOSOMAL DOMINANT, affected (N/GAG del), 46, XY; RG-283; MUSCULAR DYSTROPHY, DUCHENNE TYPE (DMD), affected, 46, XY; RG-288; CYSTIC FIBROSIS (CF), affected (deltaF508/deltaF508), 46, XY; RG-289; CYSTIC FIBROSIS (CF), affected (deltaF508/deltaF508), 46, XX; |

TABLE 2-continued

Human ES cell lines

| Institution (Country) | Name |
|---|---|
| | RG-301; MUSCULAR DYSTROPHY, DUCHENNE TYPE (DMD) affected, 46, XY; |
| | RG-302; MUSCULAR DYSTROPHY, DUCHENNE TYPE (DMD), carrier, 46, XX; |
| | RG-315; NEUROFIBROMATOSIS, TYPE I (NF1), affected (R1947X/N), 46, XY; |
| | RG-316; TUBEROUS SCLEROSIS, TYPE 1(TSC1), affected (N/IVS7 + 1 G-A); |
| | RG-316; TUBEROUS SCLEROSIS, TYPE 1(TSC1), affected (N/IVS7 + 1 G-A); |
| | RG-320; TUBEROUS SCLEROSIS, TYPE 1(TSC1), affected (N/IVS7 + 1 G-A); |
| | RG-326; POPLITEAL PTERYGIUM SYNDROME (PPS), affected (R84H/N), 46, XY; |
| | RG-328; FACIOSCAPULOHUMERAL MUSCULAR DYSTROPHY 1A(FSHD), affected, 46, XY; |
| | RG-330; FACIOSCAPULOHUMERAL MUSCULAR DYSTROPHY 1A (FSHD), affected, 46, XY; |
| | RG-333; FACIOSCAPULOHUMERAL MUSCULAR DYSTROPHY 1A (FSHD), affected, 46, XX; |
| | RG-356; HEMOGLOBIN ALPHA LOCUS (HBA), affected (-alpha/—), 46, XX; |
| | RG-357; EMERY-DREIFUSS MUSCULAR DYSTROPHY, X-LINKED (EDMD), affected, 46, XY; |
| | RG-358; EMERY-DREIFUSS MUSCULAR DYSTROPHY, X-LINKED (EDMD), affected, 46, XY; |
| | RG-399; FACIOSCAPULOHUMERAL MUSCULAR DYSTROPHY 1A (FSHD), affected, 46, XX; |
| | RG-401; FACIOSCAPULOHUMERAL MUSCULAR DYSTROPHY 1A (FSHD), affected, 46, XX; |
| | RG-402; FACIOSCAPULOHUMERAL MUSCULAR DYSTROPHY 1A (FSHD), affected, 46, XX; |
| | RG-403; FACIOSCAPULOHUMERAL MUSCULAR DYSTROPHY 1A (FSHD), affected; |
| | RG-404; SPINAL MUSCULAR ATROPHY, TYPE I (SMA1), affected, 46, XY; |
| | RG-406; TORSION DYSTONIA 1, AUTOSOMAL DOMINANT (DYT1), affected (N/GAG del); |
| | RG-413; BREAST CANCER, FAMILIAL (BRCA2), affected (N/IVS7 GT del) & MULTIPLE ENDOCRINE NEOPLASIA, TYPE I (MEN1), affected (N/3036 4bp del); |
| | RG-414; MULTIPLE ENDOCRINE NEOPLASIA, TYPE I (MEN1), affected (N/3036 4bp del); |
| | RG-415; HUNTINGTON DISEASE (HD), affected; |
| | RG-416; CYSTIC FIBROSIS (CF), affected (deltaF508/1717-1 G-A); |
| | RG-417; CYSTIC FIBROSIS (CF), affected (deltaF508/1717-1 G-A); |
| | RG-418; HEMOGLOBIN BETA LOCUS (HBB), affected (cd8 + G/619del); |
| | RG-420; HEMOGLOBIN BETA LOCUS (HBB), affected (cd8 + G/619del); |
| | RG-422; CYSTIC FIBROSIS (CF), affected (N1303K/deltaF508); |
| | RG-423; CYSTIC FIBROSIS (CF), carrier (N/deltaF508); |
| | RG-424; MULTIPLE ENDOCRINE NEOPLASIA, TYPE 2 (MEN2B), affected (M918T/N); |
| | RG-426; PELIZAEUS-MERZBACHER DISEASE (PMLD), affected; |
| | RG-428; TUBEROUS SCLEROSIS, TYPE 1 (TSC1), affected (N/IVS7 + 1 G-A) |
| South American | |
| Instituto de Biociências, São Paulo (Brazil) | BR-1 |
| Middle East | |
| Technion-Israel Institute of Technology, Haifa (Israel) | TE03, TE04, TE06 (I3, I4, I6) |
| Hadassah University Hospital (Israel) | HAD 1; HAD 2; HAD 3; HAD 4; HAD 5; HAD 6 |
| Hebrew University of Jerusalem | HEFX1 |
| Technion - Israel Institute of Technology | I3; I3.2; I3.3; 14; 16; 16.2; J3; J3.2 |
| Royan Institute (Iran) | ARMD.1.H.iPSC.2; BOM.1.H.iPSC.1; CNS.1.H.iPSC.10; CNS.2.H.iPSC.7; FHC.1.H.iPSC.3; GSD.1.H.iPSC.7; HER.1.H.iPSC.1; LCA.1.H.iPSC.1; LHON.1.H.iPSC.5; |

TABLE 2-continued

Human ES cell lines

| Institution (Country) | Name |
|---|---|
| | R.1.H.iPSC.1; R.1.H.iPSC.4; R.1.H.iPSC.9; Royan H1; Royan H10; Royan H2; Royan H3; Royan H4; Royan H5; Royan H6; Royan H7; Royan H8; Royan H9; RP.1.H.iPSC.2; RP2.H.iPSC.3; TYR.1.H.iPSC.1; USH.1.H.iPSC.6 |

Europe

| Institution (Country) | Name |
|---|---|
| Cellartis AB, Gotenberg (Sweden) | SA001, SA002 (Sahlgrenska 1, Sahlgrenska 2); SA002.2; SA003; AS034.1; AS034.1.1; AS034.2; AS038; AS046; FC018; ASo85; AS094; SA111; SA121; SA142; SA167; SA181; SA191; SA196; SA202; SA203; SA211; SA218; SA240; SA279; SA348; SA352; SA399; SA461; SA502; SA506; SA521; SA540; SA611 |
| Karolinska Institutet (Sweden) | HS181; HS207; HS235; HS237; HS293; HS306; HS346; HS351; HS356; HS360; HS361; HS362; HS363; HS364; HS366; HS368; HD380; HS382; HS400; HS401; HS402; HS415; HS420; HS422; HS426; HS429; HS429A; HS429B; HS429C; HS429D; HS475; HS480; HS481; HS539 |
| Göteborg University, Göteborg (Sweden) | SA04-SA19 (Sahlgrenska 4-Sahlgrenska 19) |
| Karolinska Institute, Stockholm (Sweden) | KA08, KA09, KA40, KA41, KA42, KA43 (hICM8, hICM9, hICM40, hICM41, hICM42, hICM43) |
| Geneva University (Switzerland) | CH-ES1 |
| University of Basel (Switzerland) | CH-ES3; CH-ES3; CH-ES5 |
| Roslin Cells Ltd (UK) | RC2; RC3; RC4; RC5 |
| University of Newcastle upon Tyne (UK) | NCL-1; NCL-2; NCL-3; NCL-4; NCL-5; NCL-6; NCL-7; NCL-8; NCL-9 |
| Roslin Institute (Edinburgh) & Geron Corporation (UK) | RH1; RH2; RH3; RH4; RH5; RH6; RH7; RH9; |
| University of Manchester (UK) | Man 2 |
| King's College London (UK) | KCL-001 (formerly WT3) |
| The University of Sheffield, Sheffield (UK) | SHEF-1; SHEF-2; SHEF-3; SHEF-4; SHEF-5; SHEF-6; SHEF-7; SHEF-8 |
| Universities of Edinburgh & Oxford; University of Cambridge (UK) | Edi-1; Edi-2; Edi-3; Edi-4 |
| Roslin Cells Ltd, Roslin Institute, Universities of Edinburgh & Manchester, Central Manchester & Manchester Children's University Hospitals NHS Trust (UK) | RCM-1; RC-1; RC-2; RC-3; RC-4; RC-5; RC-6; RC-7; RC-8; RC-9; RC-10 |
| King's College London & Guy's Hospital Trust/Charitable Foundation of Guy's & St Thomas (UK) | KCL-003-CF1 (formerly CF1); KCL-005-HD1; KCL008-HD-2; KCL009-trans-1; KCL-001 (WT-3); KCL-001 (WT-4) |
| Stem Cell Sciences Ltd, Australia (SCS) & Australian Stem Cell Centre (ASCC) | MEL-1; MEL-2; MEL-3; MEL-4 |
| University of Edinburgh (UK) | CB660 |
| Axordia Ltd. (UK) | Shef-1; Shef-2; Shef-3; Shef-4; Shef-5; Shef-6; Shef-7 |
| University of Nottingham (UK) | Nott-1; Nott-2 |
| Centre of Regenerative Medicine in Barcelona (Spain) | ES-2; ES-3; ES-4; ES-5; ES-6; ES-7; ES-8; ES-9; ES-10; ES-11EM; cFA404-KiPS4F-1; cFA404-KiPS4F-3; KiPS3F-7; KiPS4F-1; KiPS4F-8 |
| Principe Felipe Centro de Investigacion (Spain) | VAL-3; VAL-4; VAL-5; VAL-6M; VAL-7; VAL-8; VAL-9; VAL-10B |
| Université Libre de Bruxelles (Belgium) | ERA-1; ERA2; ERA-3; ERAMUC-1; ERAMUC-1 |
| Vrije Universiteit Brussel (Belgium) | VUB01; VUB02; VUB06; VUB07; VUB03_DM1; VUB04_CF; VUB05_HD; VUB08_MFS; VUB09_FSHD; VUB10_SCA7; VUB11_FXS; VUB13_FXS; VUB14; VUB19_DM1; VUB20_CMT1A; VUB22_CF; VUB23_OI; VUB24_DM1; VUB26; VUB27; VUB28_HD_MFS |
| Central Manchester and Manchester Children's University Hospitals NHS (UK) | Man 1; Man 2 |
| Université Paris-Sud 11 (France) | CL01; CL02; CL03; PB04; PB05; PB05-1; PB06; PB06-1; PB07; PB08; PB09; PB10 |
| INSERM (France) | OSCAR; STR-I-155-HD; STR-I-171-GLA; STR-I-189-FRAXA; STR-I-203-CFTR; STR-I-209-MEN2a; STR-I-211-MEN2a; STR-I-221-Sca2; STR-I-229-MTMX; STR-I-231-MTMX; STR-I-233-FRAXA; STR-I-251-CFTR; STR-I-301-MFS; STR-I-305-APC; STR-I-315-CMT1a; STR-I-347-FRAXA; STR-I-355-APC; STR-I-359-APC |

TABLE 2-continued

Human ES cell lines

| Institution (Country) | Name |
|---|---|
| Masaryk University (Czech Republic) | CCTL 6; CCTL 8; CCTL 9; CCTL 10; CCTL 12; CCTL 13; CCRL 14 |
| Aalborg University (Denmark) | CLS1; CLS2; CLS3; CLS4 |
| University of Copenhagen (Denmark) | LRB001; LRB002; LRB003; LRB004; LRB005; LRB006; LRB007; LRB008; LRB009; LRB010; LRB011; LRB013; LRB014; LRB016; LRB017; LRB018; |
| University of Southern Denmark | KMEB1; KMEB2; KMEB3; KMEB4; KMEB |
| University of Helsinki (Finland) | FES21; FES22; FES29; FES30; FES61; FES75 |
| University of Tampere (Finland) | Regea 06/015; Regea 06/040; Regea 07/027; Regea 07/046; Regea 08/013; Regea 08/017; Regea 08/023; Regea 08/056 |
| Leiden University Medical Center (Netherlands) | HESC-NL1; HESC-NL2; HESC-NL3; HESC-NL4 |
| Russian Academy of Sciences (Russia) | ESM01; ESM02; ESM03; |
| Instanbul Memorial Hospital (Turkey) | MINE: NS-2; NS-3; NS-4; NS-5; NS-6; NS-7; NS-8; NS-9; NS-10; OZ-1; OZ-2; OZ-3; OZ-4; OZ-5; OZ-6; OZ-7; OZ-8 |

Australia

| Institution (Country) | Name |
|---|---|
| Monash University (Australia) | Envy |
| Prince of Wales Hospital, Sydney (Australia) | E1C1; E1C2; E1C3; E1C4; Endeavour 1; Endeavour 2; hES3.1; hES3.2; hES3.3 |
| Sydney IVF Limited (Australia) | SIVF01; SIVF03; SIVF05; SIVF06; SIVF07; SIVF08; SIVF09; SIVF10; SIVF11; SIVF12; SIVF13 |

Asia

| Institution (Country) | Name |
|---|---|
| Kyoto University (Japan) | 201B1; 201B2; 201B3; 201B6; 201B7; 243H1; 243H7; 246G1; 246G3; 246G4; 246G5; 246G6; khES-1; khES-2; khES-3; |
| Singapore Stem Cell Consortium | ESI-013; ESI-014; ESI-017; ESI-027; ESI-035; ESI-049; ESI-051; ESI-053 |
| ES Cell International Pte Ld (Singapore) | ES01, ES02, ES03, ES04, ES05, ES06 (HES-1, HES-2, HES-3, HES-4, HES-5, HES-6 |
| Maria Biotech Co. Ltd. - Maria Infertility Hospital Medical Institute, Seoul (Korea) | MB01, MB02, MB03; MB04; MB05; MB06; MB07; MB08; MB09 |
| MizMedi Hospital-Seoul National University, Seoul (Korea) | MI01 (Miz-hES1); Miz-hES2; Miz-hES3; Miz-hES4; Miz-hES5; Miz-hES6; Miz-hES7; Miz-hES8; Miz-hES9; Miz-hES10; Miz-hES11; Miz-hES12; Miz-hES13; Miz-hES14; Miz-hES15; |
| Pochon CHA University College of Medicine (Korea) | CHA-hES3; CHA-hES4 |
| Seoul National University (Korea) | SNUhES1; SNUhES2; SNUhES3; SNUhES4; SNUhES11; SNUhES16 |
| National Centre for Biological Sciences/Tata Institute of Fundamental Research, Bangalore (India) | NC01, NC02, NC03 (FCNCBS1, FCNCBS2, FCNCBS3); BJN-hem19; BJN-hem20 |
| Reliance Life Sciences, Mumbai (India) | RL05, RL07, RL10, RL13, RL15, RL20, RL21 (RLS ES 05, RLS ES 07, RLS ES 10 |
| National Institute for Research in Reproductive Health (India) | KIND-1; KIND-2 |
| Tata Institute of Fundamental Research (India) | FCNCBS1; FCNCBS2; FCNCBS3 |
| Kaohsiung Medical University (Taiwan) | T1; T2; T3; T4; T5 |
| Central South University (China) | chESC-3 (H3); chESC-8; chESC-20; chESC-22; EBNA1 + H9 |
| Graduate University of Chinese Academy of Sciences (China) | hPES-1; hPES-2 |
| Huazhong University of Science and Technology (China) | hES-8; hES18 |
| Peking University Third Hospital (China) | B4; B7; PKU1; PKU2 |
| Shanghai Jiao Tong University School of Medicine (China) | SHhES1 |
| Shanghei Second Medical University (China) | SH1; SH2; SH4; SH7; SH28; SH35; SH35a; SH38; SH39; SH42 |
| Sun Yat-sen University (China) | CHES-1; SYSU-1; SYSU-2 |
| Sun Yat-sen University Second Affiliated Hospital (China) | CHE-1; CHE-2; CHE-3 |
| The Third Affiliated Hospital of Guangzhou Medical College (China) | FY-hES-5; FY-hES-9; FY-hES-10;; FY-hES-11 |

TABLE 3

Listing of human induced pluripontent stem (hIPS) cell lines

| | |
|---|---|
| University of Wisconsin - Madison (USA) | 1. IPS(FORESKIN)-1 (Normal; 46XY; Yu, J., et al. [Thomson] Science. 2007 Induced pluripotent stem cell lines derived from human somatic cells 318(5858): 1917-20.)<br>2. IPS(FORESKIN)-2 (Normal; 46XY; Yu, J., et al. [Thomson] Science. 2007 Induced pluripotent stem cell lines derived from human somatic cells 318(5858): 1917-20.)<br>3. IPS(FORESKIN)-3 (Normal; 46XY; Yu, J., et al. [Thomson] Science. 2007 Induced pluripotent stem cell lines derived from human somatic cells 318(5858): 1917-20.)<br>4. IPS(FORESKIN)-4 (Normal; 46XY; Yu, J., et al. [Thomson] Science. 2007 Induced pluripotent stem cell lines derived from human somatic cells 318(5858): 1917-20.)<br>5. IPS(IMR90)-1 (Normal; 46XX; Yu, J., et al. [Thomson] Science. 2007 Induced pluripotent stem cell lines derived from human somatic cells 318(5858): 1917-20.)<br>6. IPS(IMR90)-2 (Normal; 46XX; Yu, J., et al. [Thomson] Science. 2007 Induced pluripotent stem cell lines derived from human somatic cells 318(5858): 1917-20.)<br>7. IPS(IMR90)-3 (Normal; 46XX; Yu, J., et al. [Thomson] Science. 2007 Induced pluripotent stem cell lines derived from human somatic cells 318(5858): 1917-20.)<br>8. IPS(IMR90)-4 (Normal; 46XX; Yu, J., et al. [Thomson] Science. 2007 Induced pluripotent stem cell lines derived from human somatic cells 318(5858): 1917-20.)<br>9. IPS-SMA-3.5 (Normal; 46XY; Type 1 Spinal Muscular Atrophy; Ebert, A. D., et al. 2009. Induced pluripotent stem cells from a spinal muscular atrophy patient Nature. 457: 277-80)<br>10. IPS-SMA-3.6 (Normal; 46XY; Type 1 Spinal Muscular Atrophy; Ebert, A. D., et al. 2009. Induced pluripotent stem cells from a spinal muscular atrophy patient Nature. 457: 277-80)<br>11. IPS-WT (Normal; 46XX; Type 1 Spinal Muscular Atrophy; Ebert, A. D., et al. 2009. Induced pluripotent stem cells from a spinal muscular atrophy patient Nature. 457: 277-80) |
| University of California, Los Angeles (USA) | 1. IPS-1 (Karumbayaram, S. et al. 2009. Directed Differentiation of Human-Induced Pluripotent Stem Cells Generates Active Motor NeuronsStem Cells. 27: 806-811; Lowry, W. E., et al.. 2008. Generation of human induced pluripotent stem cells from dermal fibroblasts. Proc Natl Acad Sci USA. 105: 2883-8)<br>2. IPS-2 (Karumbayaram, S. et al. 2009. Directed Differentiation of Human-Induced Pluripotent Stem Cells Generates Active Motor NeuronsStem Cells. 27: 806-811; Lowry, W. E., et al.. 2008. Generation of human induced pluripotent stem cells from dermal fibroblasts. Proc Natl Acad Sci USA. 105: 2883-8)<br>3. IPS-5 (Lowry, W. E., et al.. 2008. Generation of human induced pluripotent stem cells from dermal fibroblastsProc Natl Acad Sci USA. 105: 2883-8)<br>4. IPS-7 (Lowry, W. E., et al.. 2008. Generation of human induced pluripotent stem cells from dermal fibroblasts. Proc Natl Acad Sci USA. 105: 2883-8)<br>5. IPS-18 (Karumbayaram, S. et al. 2009. Directed Differentiation of Human-Induced Pluripotent Stem Cells Generates Active Motor NeuronsStem Cells. 27: 806-811; Lowry, W. E., et al.. 2008. Generation of human induced pluripotent stem cells from dermal fibroblasts. Proc Natl Acad Sci USA. 105: 2883-8)<br>6. IPS-24 (Lowry, W. E., et al.. 2008. Generation of human induced pluripotent stem cells from dermal fibroblasts. Proc Natl Acad Sci USA. 105: 2883-8)<br>7. IPS-29 (Lowry, W. E., et al.. 2008. Generation of human induced pluripotent stem cells from dermal fibroblasts. Proc Natl Acad Sci USA. 105: 2883-8) |
| Mt. Sinai Hospital (Samuel Lunenfeld Research Institute; USA) | 1. (Woltjen, K. et al. 2009. PiggyBac transposition reprograms fibroblasts to induced pluripotent stem cells Nature. 458(7239): 766-70)<br>2. 61 (Woltjen, K. et al. 2009. PiggyBac transposition reprograms fibroblasts to induced pluripotent stem cells Nature. 458(7239): 766-70)<br>3. 66 (Woltjen, K. et al. 2009. PiggyBac transposition reprograms fibroblasts to induced pluripotent stem cells Nature. 458(7239): 766-70)<br>4. 67 (Woltjen, K. et al. 2009. PiggyBac transposition reprograms fibroblasts to induced pluripotent stem cells Nature. 458(7239): 766-70)<br>5. HIPSC117 (Kaji K, et al. 2009 Virus-free induction of pluripotency and subsequent excision of reprogramming factors Nature458(7239): 771-5)<br>6. HIPSC121 (Kaji K, et al. 2009 Virus-free induction of pluripotency and subsequent excision of reprogramming factors Nature458(7239): 771-5)<br>7. HIPSC122 (Kaji K, et al. 2009 Virus-free induction of pluripotency and subsequent excision of reprogramming factors Nature458(7239): 771-5) |

TABLE 3-continued

Listing of human induced pluripontent stem (hIPS) cell lines

| | |
|---|---|
| Children's Hospital -Boston (USA) | 1. 551-IPS8 (Park IH, et al. 2008. Reprogramming of human somatic cells to pluripotency with defined factors. Nature 451: 141-6).<br>2. ADA-IPS2 ((ADA-SCID) Adenosine Deaminase Deficiency-related Severe Combined Immunodeficiency (GGG > AGG, exon 7, ADA gene); Park, I. H. et al. 2008. Disease-Specific Induced Pluripotent Stem Cells Cell134(5): 877-86)<br>3. ADA-IPS3 ((ADA-SCID) Adenosine Deaminase Deficiency-related Severe Combined Immunodeficiency (GGG > AGG, exon 7, ADA gene); Park, I. H. et al. 2008. Disease-Specific Induced Pluripotent Stem Cells Cell134(5): 877-86)<br>4. BJ1-IPS1 (Park, I. H. et al. 2008. Disease-Specific Induced Pluripotent Stem Cells Cell134(5): 877-86)<br>5. BMD-IPS1 (Male; (BMD) Becker Muscular Dystrophy (Unidentified mutation in dystrophin); Park, I. H. et al. 2008. Disease-Specific Induced Pluripotent Stem Cells Cell134(5): 877-86)<br>6. BMD-IPS4 (Normal; 46XY; (BMD) Becker Muscular Dystrophy (Unidentified mutation in dystrophin); Park, I. H. et al. 2008. Disease-Specific Induced Pluripotent Stem Cells Cell134(5): 877-86)<br>7. DH1CF16-IPS1 (Normal; 46XY; Park, I. H. et al. 2008. Disease-Specific Induced Pluripotent Stem Cells Cell134(5): 877-86)<br>8. DH1CF32-IPS2 (Male; Park, I. H. et al. 2008. Disease-Specific Induced Pluripotent Stem Cells Cell134(5): 877-86)<br>9. DH1F-IPS3-3(Normal; 46XY; Park, I. H. et al. 2008. Disease-Specific Induced Pluripotent Stem Cells Cell134(5): 877-86)<br>10. DMD-IPS1 ((Normal; 46XY; DMD) Duchenne Muscular Dystrophy (Deletion of exon 45-52, dystrophin gene; Park, I. H. et al. 2008. Disease-Specific Induced Pluripotent Stem Cells Cell134(5): 877-86)<br>11. DMD-IPS2 (Male; (DMD) Duchenne Muscular Dystrophy (Deletion of exon 45-52, dystrophin gene; Park, I. H. et al. 2008. Disease-Specific Induced Pluripotent Stem Cells Cell134(5): 877-86)<br>12. DS1-IPS4 (Male; Down syndrome (Trisomy 21); Park, I. H. et al. 2008. Disease-Specific Induced Pluripotent Stem Cells Cell134(5): 877-86)<br>13. DS2-IPS1 (Male; Down syndrome (Trisomy 21); Park, I. H. et al. 2008. Disease-Specific Induced Pluripotent Stem Cells Cell134(5): 877-86)<br>14. DS2-IPS10 (Male; Down syndrome (Trisomy 21); Park, I. H. et al. 2008. Disease-Specific Induced Pluripotent Stem Cells Cell134(5): 877-86)<br>15. GD-IPS1(Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell134(5): 877-86)<br>16. GD-IPS3 (Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell134(5): 877-86)<br>17. HFIB2-IPS2 (Park, I. H., et al. 2008. Generation of human-induced pluripotent stem cells Nat Protoc. 3: 1180-6; Park, I. H. et al. 2008. Reprogramming of human somatic cells to pluripotency with defined factors. Nature. 451: 141-6)<br>18. HFIB2-IPS4 (Park, I. H., et al. 2008. Generation of human-induced pluripotent stem cells Nat Protoc. 3: 1180-6; Park, I. H. et al. 2008. Reprogramming of human somatic cells to pluripotency with defined factors. Nature. 451: 141-6)<br>19. HFIB2-IPS5 (Park, I. H., et al. 2008. Generation of human-induced pluripotent stem cells Nat Protoc. 3: 1180-6; Park, I. H. et al. 2008. Reprogramming of human somatic cells to pluripotency with defined factors. Nature. 451: 141-6)<br>20. JDM-IPS1 (Normal, 46XX; Juvenile diabetes mellitus (multifactorial); Park, I. H. et al. 2008. Disease-Specific Induced Pluripotent Stem Cells Cell134(5): 877-86)<br>21. JDM-IPS1 (Normal, 46XX; Juvenile diabetes mellitus (multifactorial); Park, I. H. et al. 2008. Disease-Specific Induced Pluripotent Stem Cells Cell134(5): 877-86)<br>22. JDM-IPS2 (Female; Juvenile diabetes mellitus (multifactorial); Park, I. H. et al. 2008. Disease-Specific Induced Pluripotent Stem Cells Cell134(5): 877-86)<br>23. JDM-IPS3 (Female; Juvenile diabetes mellitus (multifactorial); Park, I. H. et al. 2008. Disease-Specific Induced Pluripotent Stem Cells Cell134(5): 877-86)<br>24. LNSC-IPS2 (Female; Lesch-Nyhan syndrome (carrier, heterozygosity of HPRT1; Park, I. H. et al. 2008. Disease-Specific Induced Pluripotent Stem Cells Cell134(5): 877-86)<br>25. MRC5-IPS7 (Male; Park, I. H. et al. 2008. Disease-Specific Induced Pluripotent Stem Cells Cell134(5): 877-86)<br>26. MRC5-IPS12 (Normal; 46XY; Park, I. H. et al. 2008. Disease-Specific Induced Pluripotent Stem Cells Cell134(5): 877-86)<br>27. MRC5-IPS1 (Male; Park, I. H. et al. 2008. Disease-Specific Induced Pluripotent Stem Cells Cell134(5): 877-86)<br>28. PD-IPS1 (Male; Parkinson disease (multifactorial); Park, I. H. et al. 2008. Disease-Specific Induced Pluripotent Stem Cells Cell134(5): 877-86) |

TABLE 3-continued

Listing of human induced pluripotent stem (hIPS) cell lines

| | |
|---|---|
| | 29. SBDS-IPS1 (Male; Swachman-Bodian-Diamond syndrome (IV2 + 2T > C and IV3 − 1G > A, SBDS gene; Park, I. H. et al. 2008. Disease-Specific Induced Pluripotent Stem Cells Cell134(5): 877-86)<br>30. SBDS-IPS2<br>31. SBDS-IPS3 (Normal; 46XY; Swachman-Bodian-Diamond syndrome (IV2 + 2T > C and IV3 − 1G > A, SBDS gene; Park, I. H. et al. 2008. Disease-Specific Induced Pluripotent Stem Cells Cell134(5): 877-86) |
| Harvard University (USA) | 1. A29a (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neuronsScience. 321: 1218-21)<br>2. A29b (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neuronsScience. 321: 1218-21)<br>3. A29c (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neuronsScience. 321: 1218-21) |
| Salk Institute (USA) | 1. HAIR-IPS1 (Aasen, T., et al [Belmonte, J. C.] 2008. Efficient and rapid generation of induced pluripotent stem cells from human keratinocytesNat Biotechnol. 26: 1276-84)<br>2. HAIR-IPS2 (Aasen, T., et al [Belmonte, J. C.] 2008. Efficient and rapid generation of induced pluripotent stem cells from human keratinocytesNat Biotechnol. 26: 1276-84) |
| Royan Institute (Iran) | 1. R.1.H.iPSC.1(OCT4, Sox2, KLF4, c-Myc; Human fibroblasts)<br>2. BOM.1.H.iPSC.1 (OCT4, Sox2, KLF4, c-Myc; Human fibroblasts)<br>3. FHC.1.H.iPSC.3 (OCT4, Sox2, KLF4, c-Myc; Human fibroblasts)<br>4. GSD.1.H.iPSC.7 (OCT4, Sox2, KLF4, c-Myc; Human fibroblasts)<br>5. TYR.1.H.iPSC.1 (OCT4, Sox2, KLF4, c-Myc; Human fibroblasts)<br>6. HER.1.H.iPSC.1 (OCT4, Sox2, KLF4, c-Myc; Human fibroblasts)<br>7. R.1.H.iPSC.4 (OCT4, Sox2, KLF4, c-Myc; Human fibroblasts)<br>8. R.1.H.iPSC.9 (OCT4, Sox2, KLF4, c-Myc; Human fibroblasts)<br>9. RP2.H.iPSC.3 (OCT4, Sox2, KLF4, c-Myc; iPS cells)<br>10. LCA.1.H.iPSC.1 (OCT4, Sox2, KLF4, c-Myc; iPS cells)<br>11. USH.1.H.iPSC.6 (OCT4, Sox2, KLF4, c-Myc; Human fibroblasts)<br>12. RP.1.H.iPSC.2 (OCT4, Sox2, KLF4, c-Myc; Human fibroblasts)<br>13. ARMD.1.H.iPSC.2 (OCT4, Sox2, KLF4, c-Myc; Human fibroblasts)<br>14. LHON.1.H.iPSC.5 (OCT4, Sox2, KLF4, c-Myc; iPS cells)<br>15. CNS.1.H.iPSC.10 (OCT4, Sox2, KLF4, c-Myc; iPS cells)<br>16. CNS.2.H.iPSC.7 (OCT4, Sox2, KLF4, c-Myc; iPS cells) |
| Centre of Regenerative Medicine in Barcelona (Spain) | 1. KiPS4F-1 (OCT4, Sox2, KLF4, c-Myc; human foreskin keratinocytes; 46XY)<br>2. KiPS3F-7 (OCT4, Sox2, KLF4); human foreskin keratinocytes)<br>3. KiPS4F-8 (OCT4, Sox2, KLF4, c-Myc human foreskin keratinocytes; 46XY)<br>4. cFA404-KiPS4F-1 (OCT4, Sox2, KLF4, c-Myc; Epidermal keratinocytes; 46XY)<br>5. cFA404-KiPS4F-3 (OCT4, Sox2, KLF4, c-Myc; Epidermal keratinocytes; 46XY) |
| Université Paris-Sud 11 (France) | 1. PB03 (Oct4, Sox2, Lin28, Nanog; Primary Amniocytes; 46XX; Lentivirus)<br>2. PB04 (Oct4, Sox2, Lin28, Nanog; Primary Amniocytes; Beta-Thalassemia affected; 46XY; Lentivirus)<br>3. PB05-1 (Oct4, Sox2, Lin28, Nanog; Primary Amniocytes; Beta-Thalassemia affected; 46XY; Lentivirus)<br>4. PB05 (Oct4, Sox2, Lin28, Nanog; Primary Amniocytes; Beta-Thalassemia affected; 46XY; Lentivirus)<br>5. PB06 (Oct4, Sox2, Lin28, Nanog; Primary Amniocytes; Down Syndrome; 47XY, +21; Lentivirus)<br>6. PB06-1 (Oct4, Sox2, Lin28, Nanog; Primary Amniocytes; Down Syndrome; 47XY, +21; Lentivirus)<br>7. PB07 (OCT4, Sox2, KLF4, c-Myc; Primary Amniocytes; 46XY; Retrotivirus)<br>8. PB08 (OCT4, Sox2, KLF4, c-Myc; Primary Amniocytes; 46XY; Retrotivirus)<br>9. PB09 (Oct4, Sox2, Lin28, Nanog; Primary Amniocytes; 46XY; Lentivirus)<br>10. PB10 (Oct4, Sox2; Primary Amniocytes46XY, Lentivirus) |
| Kyoto University (Japan) | 1. 201B1 (human fibroblast; 46XX)<br>2. 201B2 (human fibroblast; 46XX)<br>3. 201B3 (human fibroblast; 46XX)<br>4. 201B6 (human fibroblast; 46XX)<br>5. 201B7 (human fibroblast; 46XX)<br>6. 243H1 (human fibroblast)<br>7. 243H7 (human fibroblast)<br>8. 246B1 (Normal, 46XX)<br>9. 246B2 (Normal, 46XX)<br>10. 246B3 (Normal, 46XX)<br>11. 246B4 (Normal, 46XX)<br>12. 246B5 (Normal, 46XX) |

TABLE 3-continued

Listing of human induced pluripotent stem (hIPS) cell lines

| | |
|---|---|
| | 13. 246B6 (Normal, 46XX)<br>14. 246G1 (human fibroblast; Takahashi, K., et al. 2007. Induction of pluripotent stem cells from adult human fibroblasts by defined factors Cell. 131: 861-72)<br>15. 246G3 (human fibroblast; Takahashi, K., et al. 2007. Induction of pluripotent stem cells from adult human fibroblasts by defined factors Cell. 131: 861-72)<br>16. 246G4 (human fibroblast; Takahashi, K., et al. 2007. Induction of pluripotent stem cells from adult human fibroblasts by defined factors Cell. 131: 861-72)<br>17. 246G5 (human fibroblast; Takahashi, K., et al. 2007. Induction of pluripotent stem cells from adult human fibroblasts by defined factors Cell. 131: 861-72)<br>18. 246G6 (human fibroblast; Takahashi, K., et al. 2007. Induction of pluripotent stem cells from adult human fibroblasts by defined factors Cell. 131: 861-72)<br>19. 253F1 (Normal, 46XX; Takahashi, K., et al. 2007. Induction of pluripotent stem cells from adult human fibroblasts by defined factors Cell. 131: 861-72)<br>20. 253F2 (Normal, 46XX; Takahashi, K., et al. 2007. Induction of pluripotent stem cells from adult human fibroblasts by defined factors Cell. 131: 861-72)<br>21. 253F3 (Normal, 46XX; Takahashi, K., et al. 2007. Induction of pluripotent stem cells from adult human fibroblasts by defined factors Cell. 131: 861-72)<br>22. 253F4 (Normal, 46XX; Takahashi, K., et al. 2007. Induction of pluripotent stem cells from adult human fibroblasts by defined factors Cell. 131: 861-72)<br>23. 253F5 (Normal, 46XX; Takahashi, K., et al. 2007. Induction of pluripotent stem cells from adult human fibroblasts by defined factors Cell. 131: 861-72) |
| Shanghai Institutes for Biological Sciences (China) | 1. HAFDC-IPS-6 (Li C., et al. 2009 Pluripotency can be rapidly and efficiently induced in human amniotic fluid-derived cells Hum Mol Genet. 2009 Nov 15; 18(22): 4340-9)<br>2. IPS-S (Liao, J., et al. 2008. Enhanced efficiency of generating induced pluripotent stem (iPS) cells from human somatic cells by a combination of six transcription factors Cell Res. 18: 600-3) |

Still the media compositions described herein can be employed with other pluripotent cell lines such as iPS cell lines.for example, at least iPS (Foreskin), and clones of iPS (IMR90), as well as clones of iPS—DF19-9, which is a vector-free iPS cell line. and other cell lines from Kyoto University's Center for iPS Cell Research and Application (CiRA; Shinya Yamanaka) and University of Wisconsin (James Thomson); and some of which are available from WiCell.

Changes thereof and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

What is claimed is:

1. An in vitro composition comprising single human pluripotent cells whereby said pluripotent cells are plated as single cells at a low cell density in a medium comprising an effective amount of a neurotransmitter or a structural analog, derivative or physiologically acceptable salt thereof sufficient to achieve low density survival and expansion of the pluripotent cells.

2. The composition of claim 1, wherein the neurotransmitter is a neurotransmitter receptor agonist.

3. The composition of claim 2, wherein the neurotransmitter is norepinephrine.

4. The composition of claim 1, wherein the human pluripotent cells can expand in the absence of differentiation.

5. The composition of claim 1, further comprising at least one growth factor.

6. The composition of claim 5, wherein the at least one growth factor is selected from the group consisting of: an ErbB3 ligand or a functional fragment thereof; a TGF-β family member or a functional fragment thereof; an activator of insulin-like growth factor receptor (IGF-1R) or a functional fragment thereof; and an activator of a fibroblast growth factor (FGF) receptor or a functional fragment thereof.

7. The composition of claim 6, wherein the ErbB3 ligand is heregulin.

8. The composition of claim 1, wherein the pluripotent cells are plated at about 1000 cells per ml of the medium.

9. The composition of claim 1, wherein the pluripotent cells can be passaged at least 2 times.

10. The composition of claim 9, wherein the pluripotent cells retain expression of pluripotency markers upon passaging.

11. The composition of claim 1, wherein the composition is serum free.

12. The composition of claim 1, wherein the composition is Activin A free.

13. The composition of claim 1, further comprising at least one growth factor.

14. An in vitro suspension culture comprising single human pluripotent cells whereby said pluripotent cells are in suspension as single cells and an effective amount of a neurotransmitter or a structural analog, derivative or physiologically acceptable salt thereof.

15. The composition of claim 14, wherein the composition is Activin A free.

16. A method of expanding human pluripotent cells in vitro comprising:
   a. obtaining single human pluripotent cells; and
   b. plating said single human pluripotent cells as single cells at low cell density in a medium comprising an effective amount of a neurotransmitter or a structural analog, derivative or physiologically acceptable salt thereof sufficient to achieve low density survival and expansion of the pluripotent cells.

17. The method of claim 16, wherein the neurotransmitter is a neurotransmitter receptor agonist.

18. The method of claim 17, wherein the neurotransmitter receptor agonist is norepinepherine.

19. The method of claim 16, wherein the medium does not comprise Activin A.

20. The composition of claim 1, said composition being essentially free of serum and serum replacement.

21. The composition of claim 1, wherein the composition is free of a feeder cell layer.

22. The composition of claim 1, wherein the effective amount of the neurotransmitter or the structural analog, derivative or physiologically acceptable salt thereof is sufficient to achieve improved survival and expansion of the pluripotent cells as compared to a control composition without the neurotransmitter or the structural analog, derivative or physiologically acceptable salt thereof.

23. The composition of claim 14, wherein the neurotransmitter is norepinephrine.

* * * * *